(12) United States Patent
Clamer et al.

(10) Patent No.: US 10,183,955 B2
(45) Date of Patent: Jan. 22, 2019

(54) MOLECULES FOR ISOLATION OF POLYRIBOSOMES, RIBOSOMES, USES AND KITS THEREOF

(71) Applicant: Immagina Biotechnology S.r.l., Trento (IT)

(72) Inventors: Massimiliano Clamer, Trento (IT); Gabriella Viero, Trento (IT); Graziano Guella, Trento (IT); Alessandro Quattrone, Trento (IT)

(73) Assignee: Immagina Biotechnology S.r.l., Trento (IT)

( * ) Notice: Subject to any disclaimer, the term of this patent is extended or adjusted under 35 U.S.C. 154(b) by 0 days.

(21) Appl. No.: 15/744,976

(22) PCT Filed: Jul. 14, 2016

(86) PCT No.: PCT/IB2016/054210
§ 371 (c)(1),
(2) Date: Jan. 15, 2018

(87) PCT Pub. No.: WO2017/013547
PCT Pub. Date: Jan. 26, 2017

(65) Prior Publication Data
US 2018/0201625 A1    Jul. 19, 2018

(30) Foreign Application Priority Data

Jul. 21, 2015   (IT) .......................... 102015000036631

(51) Int. Cl.

| C07D 519/00 | (2006.01) |
|---|---|
| C07D 473/34 | (2006.01) |
| C12N 15/00 | (2006.01) |
| A61K 31/52 | (2006.01) |
| C12N 15/10 | (2006.01) |
| C07D 487/04 | (2006.01) |

(52) U.S. Cl.
CPC ............ *C07D 519/00* (2013.01); *A61K 31/52* (2013.01); *C07D 473/34* (2013.01); *C07D 487/04* (2013.01); *C12N 15/1003* (2013.01); *C12N 15/1041* (2013.01)

(58) Field of Classification Search
None
See application file for complete search history.

(56) References Cited

U.S. PATENT DOCUMENTS

| 2012/0059018 A1* | 3/2012 | Park | ................... | A61K 41/0071 |
| | | | | 514/262.1 |
| 2013/0122535 A1* | 5/2013 | Salic | ....................... | C12Q 1/02 |
| | | | | 435/29 |

OTHER PUBLICATIONS

Starck et al (Chem. and Biol. 11:999-1008, 2004) (Year: 2004)*
Database Registry; Chemical Abstracts [online], Database accession No. 1032658-94-8 (2008).
PCT Search Report and Written Opinion for PCT/IB2016/054210, dated Sep. 28, 2016.
Roth, et al., "Extraction of ribosomal proteins by displacement with protamine," FEBS Letters, 1(1):16-20 (1968).
Yarmolinsky et al., "Inhibition by puromycin of amino acid incorporation into protein," PNAS, 45(12): 1721-1729 (1959).

* cited by examiner

*Primary Examiner* — Richard A Schnizer
(74) *Attorney, Agent, or Firm* — Vivicar Law, PLLC

(57) ABSTRACT

Molecules of general Formula (I): able to bind to native polyribosomes engaged in active protein synthesis. The disclosure relates also to the use of the molecules of general Formula (I) for isolating at least one active ribosome from a biological sample, and for ribosome profiling, as well as kits for isolating at least one active ribosome from a biological sample.

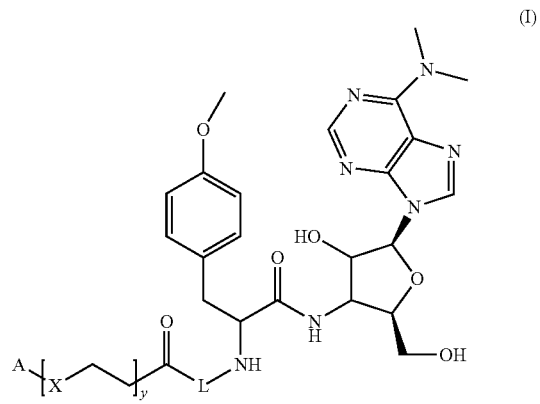

13 Claims, 33 Drawing Sheets
Specification includes a Sequence Listing.

MOLECULES FOR ISOLATION OF POLYRIBOSOMES, RIBOSOMES, USES AND KITS THEREOF

FIELD OF THE INVENTION

The present invention concerns new molecules for the tag-free isolation of native polyribosomes and ribosomes engaged in active protein synthesis, uses and kits thereof.

BACKGROUND OF THE INVENTION

Ribosomes are large molecular machines that catalyze the synthesis of new proteins. When multiple ribosomes recruit a mRNA, they form a polyribosome[1,2]. Only recently, scientists have tried to unravel the supramolecular structural and functional complexity of this 'ensemble'[3-9] (i.e. the assembly of nucleic acids and proteins). The crucial role of polyribosomes in the regulation of gene expression is highlighted by the discovery of many cancer-related mutations affecting ribosomal proteins, initiation factors as well as elongation factors interacting with polyribosomes[10]. Many components of the translation machinery are nowadays considered strategic target for the treatment of cancer and other pathologies (ribosomopathies)[11]. On top of that, recent discoveries have shown that stress conditions[12] and drug treatment[13] can specifically alter mRNAs associated within polyribosomes. All these evidences are underlining the pivotal role of polyribosomes in the process of protein synthesis and disease conditions. Additionally, the increasing number of gene expression studies on plants[14], yeasts[15] and mammalian cells[16] concerning the recruitment of RNAs on polyribosomes (translatome) are emphasizing the importance of polyribosomes in gene expression regulation.

Unfortunately, existing tools and methods to investigate translation still need to be upgraded, and innovative methods to isolate and investigate the translatome and the complexity of polyribosomes are needed. Current protocols are expensive, laborious and not enough accurate (i.e. not able to capture only native, active polyribosomes) to dissect the post-transcriptional and translational processes between transcription and protein variation. A possible approach to gain information on translation is represented by the expression of affinity-tagged ribosomal proteins whose expression is controlled by tissues specific promoters. Tagged ribosomes (and the associated mRNAs) can be purified by affinity purification (RAP or translating RAP, TRAP)[17]. This method requires a specific mouse model and/or specific gene constructs; a long path that ends up in poorly versatile systems. The advance in sequencing and proteomics technology inspired the development of high-resolution (single nucleotide or single peptide) 'omic' techniques to profile translation, including the deep sequencing of ribosome protected fragments (ribosome-profiling)[18], the global and quantitative profiling of initiating ribosomes (GTI-seq, QTI-seq)[19,20] or the genome wide quantification of the newly synthetized proteome (Punch-P and pSILAC)[21,22]. Ribosome-profiling has been also used in combination to TRAP (translating ribosome affinity purification using genetically engineered organisms) to map the translatome under oxygen deprivation[23], while Punch-P and pSILAC are complementary technologies to study gene expression regulation at the protein level. Besides different biological questions covered by these various approaches, all these techniques usually require the semi-quantitative analysis of mRNAs and proteins associated to (or produced by) polyribosomes[24].

The isolation of polyribosome by ultracentrifugation in linear sucrose gradients, a technique in use from the 1960s, is the current 'gold standard' for gene expression translational studies. Messenger RNAs associated to polyribosomes are separated from the unbound-RNAs, the small (40S), the large (60S) ribosomal subunits and the 80S monosomes. RNA and proteins can be extracted from the gradient and analyzed by RT-qPCR, RNA-seq or by immunoblotting and mass spectrometry. Although this protocol is relatively cheap (~70 € per sample) and paved the way for translatome studies[25,26], it has some drawbacks. First, the technique requires expensive equipment, handling experience and is time consuming (~6 hours). Second, sensitivity: large samples amounts (>10$^5$ cells) are required for a detectable signal profile during fractions' collection. Third, contaminations: although the presence of inactive polyribosomes is still under debate, it is known that at least in neurons polyribosomal fractions can contain non-translating (i.e. not active in protein synthesis) polyribosomes[27,28]. Furthermore, sucrose fractions could be marginally contaminated by other high molecular weight complexes[4].

Therefore, a simple, fast, more accurate and cheap technique would have a strong impact on all gene expression studies.

Innovative approaches in this direction cannot disregard to include a detailed understanding of the ribosome structure and function. Eukaryotic ribosomes are ~40% heavier than their bacterial counterparts and comprise two subunits (60s and 40S), four ribosomal RNAs and 79 ribosomal proteins, for a total mass of 4.5 MDa[29]. Ribosomes contain three active sites located in the large subunit, designated as A, P and E sites. The A site hosts an aminoacyl-tRNA (aatRNA), the P site a peptidyl-tRNA and the E site allows the free tRNA to exit the ribosome. The substrates of the reaction catalyzed by the large subunit are the incoming aminoacyl-tRNA in the A-site and the peptidyl-tRNA in the P-site. The reaction occurs in the peptidyl transferase centre (PTC). The α-amino group of the aa-tRNA attacks the carbon of the carbonyl, acylating the 3'-hydroxyl group of the peptidyl-tRNA; this resolves to yield a peptide extended by one amino acid esterified to the A site-bound tRNA and a deacylated tRNA in the P-site. Then, the ribosome translocates one codon forward.

The eukaryotic ribosome is the target of many small molecule acting as translation inhibitors. A large fraction of these molecules preferentially target the PTC[30]. This region is the catalytic core of the ribozyme (i.e. a catalytic active ribosome)[31]; and shares high-structural phylogenetic conservation with respect to the surrounding ribosomal areas[32,33]. Moreover, it is formed by RNA structural elements essential for peptide bound formation. Among small-molecular inhibitors, puromycin (an aminonucleoside antibiotic[34]) is an analogue of the 3'-end tyrosylated-tRNA, and is able to inhibit the ribosomal catalytic activity[35] in both the prokaryotic and the eukaryotic ribosomes, binding the symmetrical V-shaped cavity that forms the PTC centre[31,36] by entering into the A site. This drug played a central role in biochemical experiments aimed at understanding the mechanism of peptide-bond formation[36-40]. More recently, because of its ability to bind ribosomes and to be efficiently incorporated in the polypeptide nascent chain, puromycin has been extensively used as a tool to assay protein synthesis functions by means of radioactive puromycin[41] or antipuromycin antibodies[42]. Additionally, puromycin has also been used to chemically link an mRNA to its coded protein[43,44]. These methods are based on the irreversible reaction of the α-amino group of puromycin with the carbon on the carbonyl, acylating the 3' hydroxyl group of the peptydil-tRNA. This reaction resolves to yield a terminal puromycilated peptide, because the puromycin's amide cannot be cleaved. After that, protein synthesis stops. Given its mechanism of action, puromycin is incorporated in the nascent chain after reaction of its α-amino group.

OBJECT AND SUMMARY OF THE INVENTION

The object of the present invention is to provide new molecules (and kits thereof) able to capture native polyribosomes and ribosomes in active protein synthesis.

According to the invention, the above object is achieved thanks to the method specified in the ensuing claims, which are understood as forming an integral part of the present description.

In an embodiment, the instant disclosure discloses a molecule of general formula (I):

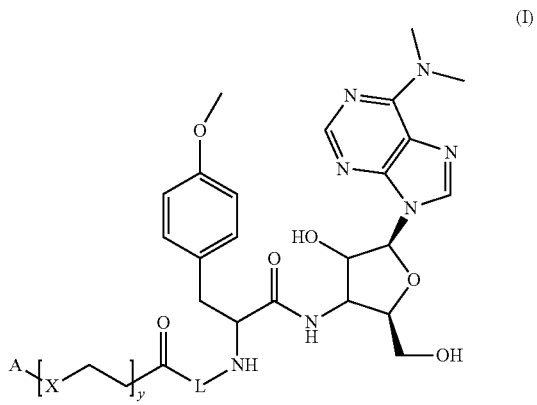

(I)

wherein

A is selected from a receptor or a ligand of a receptor-ligand system;

X is selected from an oxygen atom (O) or a carbon atom (C);

y is an integer number from 0 to 10;

L is a molecule of general formula (VI):

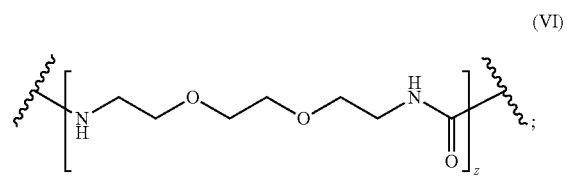

(VI)

Z is an integer number comprised in the range 2 to 10; and enantiomers thereof.

According to a further embodiment, the instant description discloses the use of the molecule of general formula (I) for isolating at least one active ribosome from a biological sample.

According to a still further embodiment, the present description concerns a kit for isolating at least one active ribosome from a biological sample including:

i) a first reagent comprising at least one molecule of general formula (I); and ii) a solid phase, wherein the solid phase is functionalized with the other of the receptor or the ligand of a receptor-ligand system, so that the solid phase binds to the first reagent.

BRIEF DESCRIPTION OF THE DRAWINGS

The invention will now be described, by way of example only, with reference to the enclosed figures of drawing, wherein.

Scatter plots from top to bottom: 'pval<0.05' DEGs data set (n=488, box I); 'pval<0.05' and '++' data set (n=112, box II); 'pval<0.05', '++' and 'FC (Log 2)>0' gene data sets (n=70, box III); 'pval<0.05', '++' and FC(Log 2)<0 gene data sets (n=42, box IV). EP, polysomal RNA from EGF-treated cells; ET, total RNA from EGF-treated cells; EB, 3P-beads RNA from EGF-treated cells; SP, polysomal RNA from serum-starved cells; ST, total RNA from serum-starved cells; SB, 3P-beads from RNA serum-starved cells. Sperman's correlation is reported for each graph. Ellipse represents a confidence level of 95%. $R^2$, Adjusted coefficient of determination.

Figure 28:
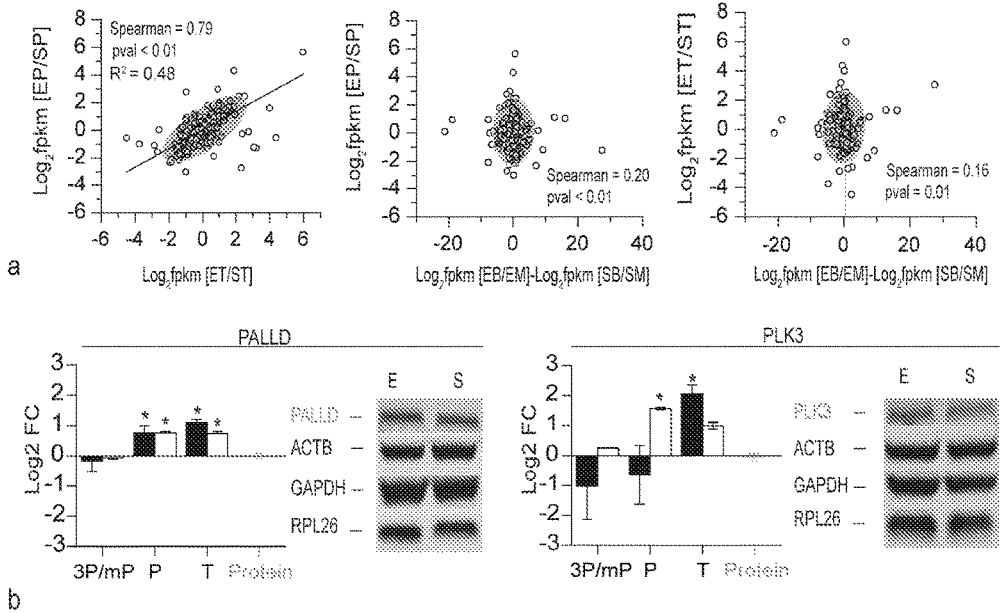

FIG. 28. RNA extracted from 3P-beads is a better proxy respect to total and polysomal RNA to predict variation in total protein abundance. (a) Scatter plots of the scaled Log 2 FC upon EGF stimulation on total (ET/ST), sucrose-gradient polyribosomal fractions (EP/SP) and 3P-to-mP ratio (Log 2 (EB/SB)–Log 2 (EM/SM)). From left to right: EP/SP (sucrose-gradient polyribosomal RNA) compared to ET/ST (total RNA); EP/SP (sucrose-gradient polyribosomal RNA) compared to the 3P-to-mP ratio; ET/ST (total RNA) compared to the 3P-to-mP ratio. EP, polyribosomal RNA from EGF-treated cells. EP, polyribosomal RNA from EGF-treated cells; ET, total RNA from EGF-treated cells; EB, 3P-beads RNA from EGF-treated cells; SP, polyribosomal PNA from serum-starved cells; ST, total RNA from serum-starved cells; SB, 3P-beads from RNA serum-starved cells. Correlation's values and p-values are reported for each plot. Ellipse represents a confidence level of 95%. (b) Protein and RNA fold changes. Black bars, RT-qPCR fold change; white bars, RNA-seq fold change; light gray bars, protein fold change. The quantitative analysis of the protein band intensity is referred to the western blots on the right of each plot (n=3). PALLD is a cytoskeletal protein required for organization of normal actin cytoskeleton and is involved in cell morphology, motility, cell adhesion and cell-extracellular matrix interactions. PLK3 (polo-like kinase) is a serine/threonine-protein kinase involved in cell cycle regulation and stress response. Housekeeping proteins: ACTB, GAPDH, RPL26. ACTB, beta actin; RPL26, ribosomal protein L26. t-test (*)=p-val<0.05. E, EGF treated; S, serum-starvation. $R^2$, Adjusted coefficient of determination.

Figure 29:
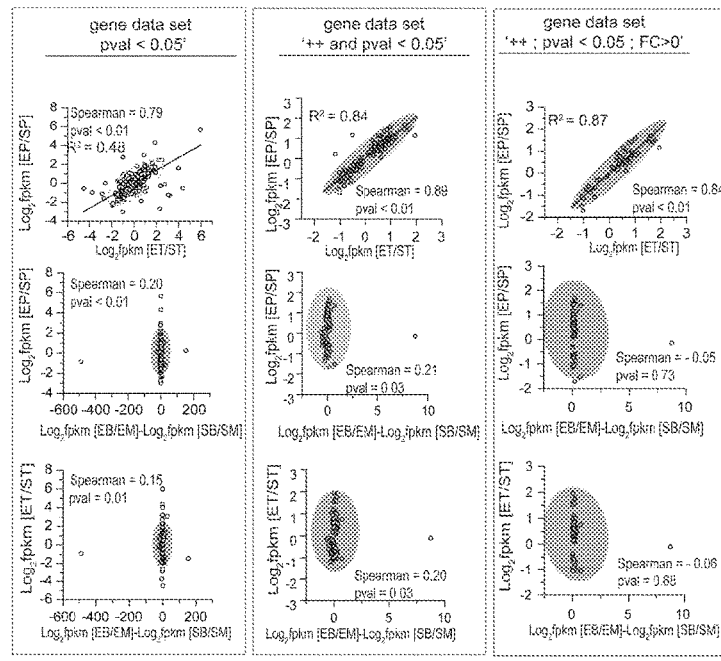

FIG. 29. Correlations of fold changes. The second and third plot in each column are including a subtraction of the background (control beads fold change) from the 3P fold change signal. From left to right: scatter plots of 'pval<0.05' gene data set (n=436, left box) including outliers that were not reported in FIG. 26; scatter plots of 'pval<0.05' and '++' data set (n=108, middle box); scatter plots of 'pval<0.05', '++' and FC>0 gene data sets (n=59, right box). EP, polysomal RNA from EGF-treated cells; ET, total RNA from EGF-treated cells; EB, 3P-beads RNA from EGF-treated cells; SP, polysomal RNA from serum-starved cells; ST, total RNA from serum-starved cells; SB, 3P-beads RNA from serum-starved cells. $R^2$, Adjusted coefficient of determination.

Figure 30:
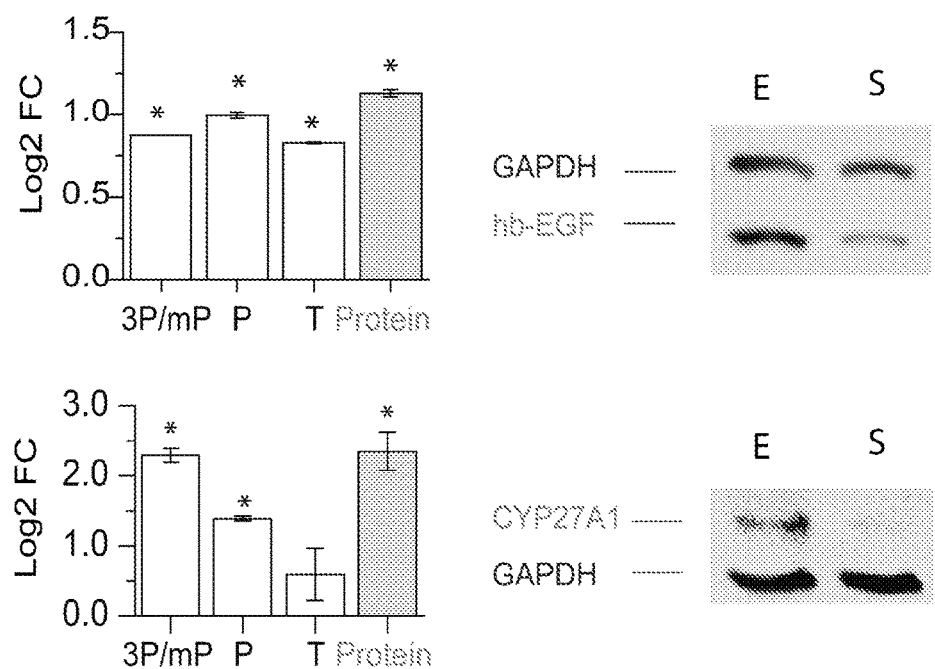

FIG. 30. RNA and protein fold changes upon EGF stimulation. Quantitative analysis of the protein band intensity referred to the western blot on the right (n=3). Housekeeping protein: GAPDH; t-test (*)=p-val<0.05. E: EGF treated; S: serum-starved. White histograms, RNA-seq fold changes; light gray, protein fold change. hb-EGF, heparin-binding EGF-like growth factor (up); CYP27A1, cytochrome P450 family 27 subfamily A member 1 (bottom)

Figure 31:
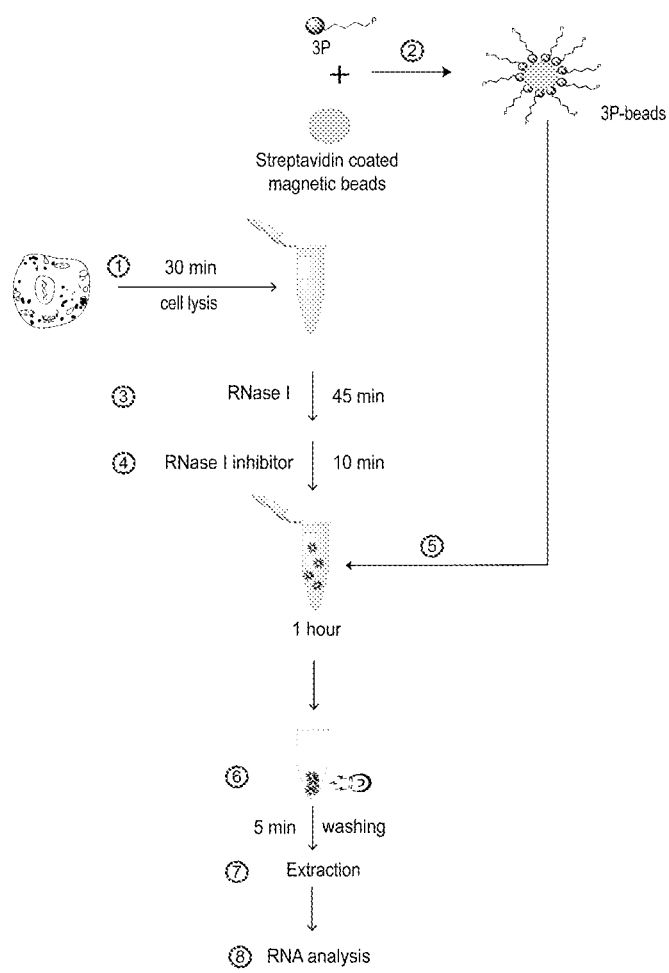

FIG. 31. Ribosome profiling with RIboLace. Sketch of steps 1-7 described in the main text 'An additional application for 3P: ribosome-profiling'.

Figure 32:
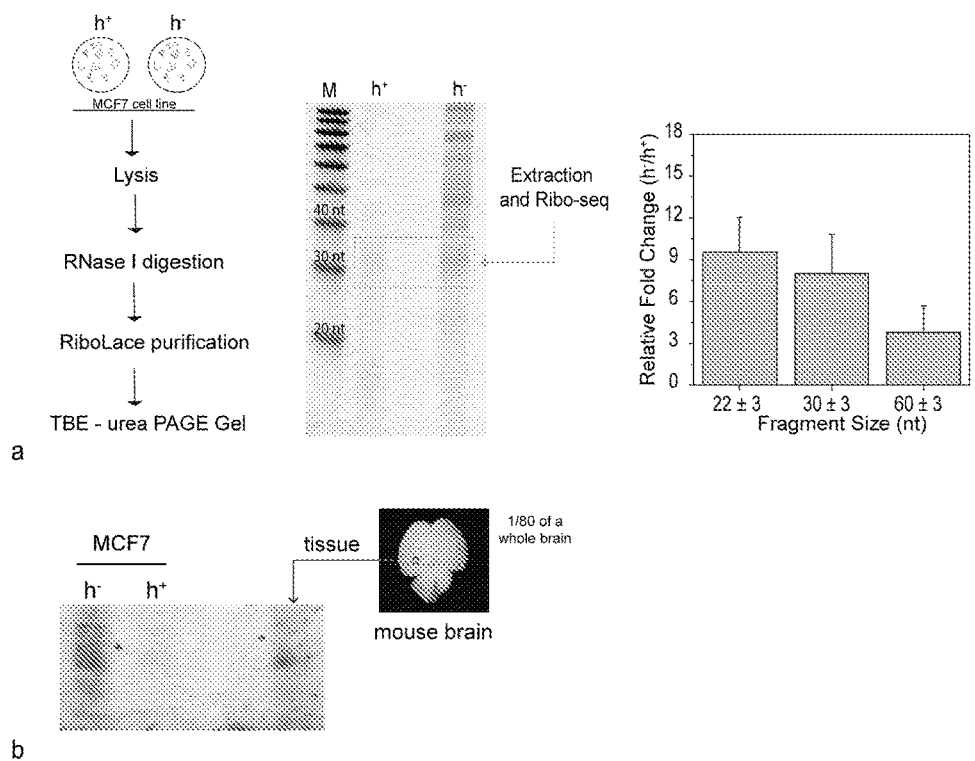

FIG. 32. Enrichment of ribosome protected fragments on 3P-beads RNA. (a, left) MCF7 cells treated (h+) or not treated (h−) with harringtonine (2 μg/mL) for 2 hours is processed as described in the scheme: (i) lysis, (ii) digestion with RNaseI, (iii) purification with 3P-dynabeads beads, (iv) RNA isolation on a TBE 1% Agarose gel. (a, middle) TBE-Urea gel (15%) reporting the isolated Ribosome Protected Fragments (RPFs). The gray box identifies the bands of interest for Ribo-seq analysis, corresponding to fragments of ~30 nucleotides in length. (a, right) Relative fold change ($h^-/h^+$) of RPFs captured with 3P-beads based on bioanalyzer. (b) Comparison between RPFs obtained from MCF7 cell lysates and mouse brain (TBE-Urea gel 15%). Beads used: Dynabeads, Life Technologies, #65001

Figure 33:
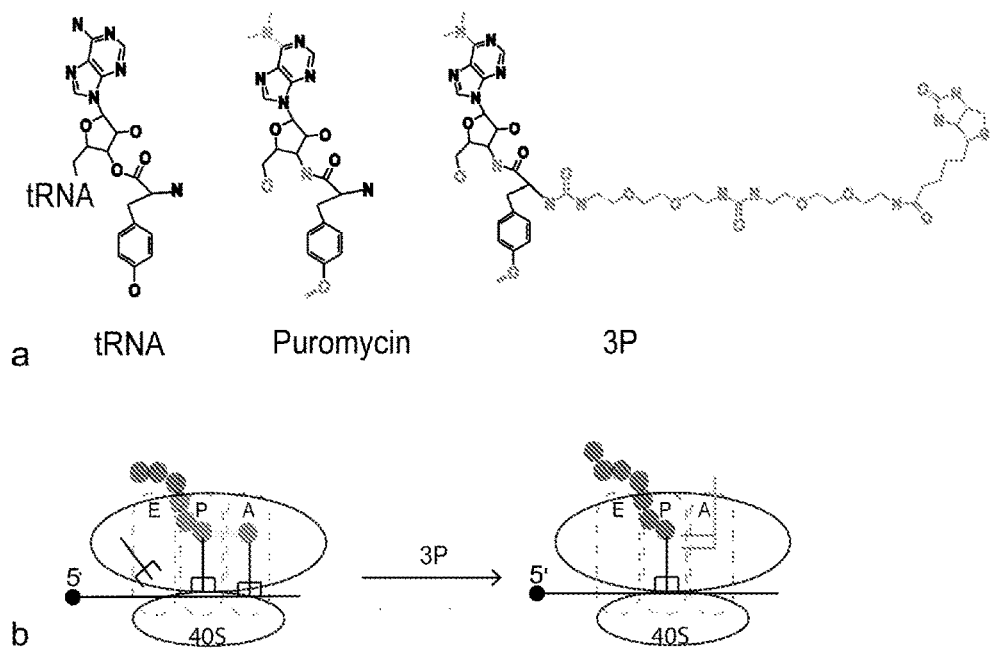

FIG. 33. Proposed mechanism for 3P activity. A tRNA molecule (top, left), puromycin (top, middle) and 3P (top, right). Differences among a tRNA, puromycin and 3P are drawn in gray. The proposed mechanism of action of 3P on ribosomes (bottom): the 3P (light gray fork) binds to the acceptor site (A) close to the PTC center of ribosomes in active translation. Black forks, tRNA; gray dots, amino acid chains; RNA, black line; 5'-end, black dots; 60S and 40S ribosomal subunits, ovals; E, exit site; P, peptidyl transference site; A, acceptor site.

Figure 34:
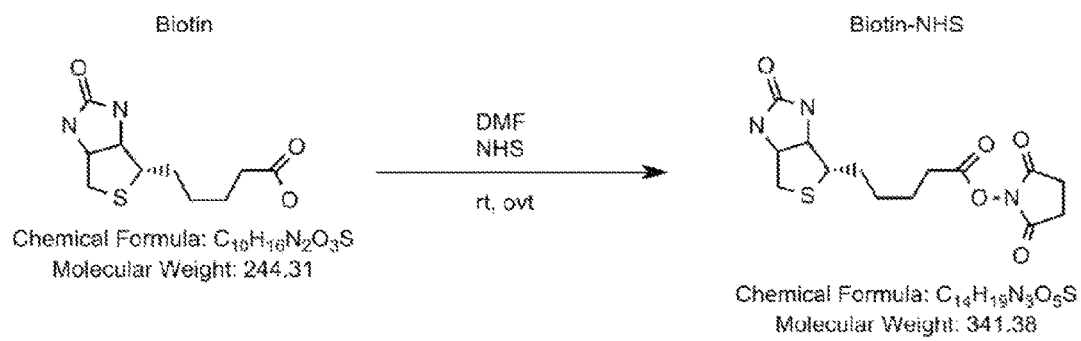

FIG. 34. Scheme I. Synthesis of Biotinyl-N-hydroxysuccinimide.

Figure 35:
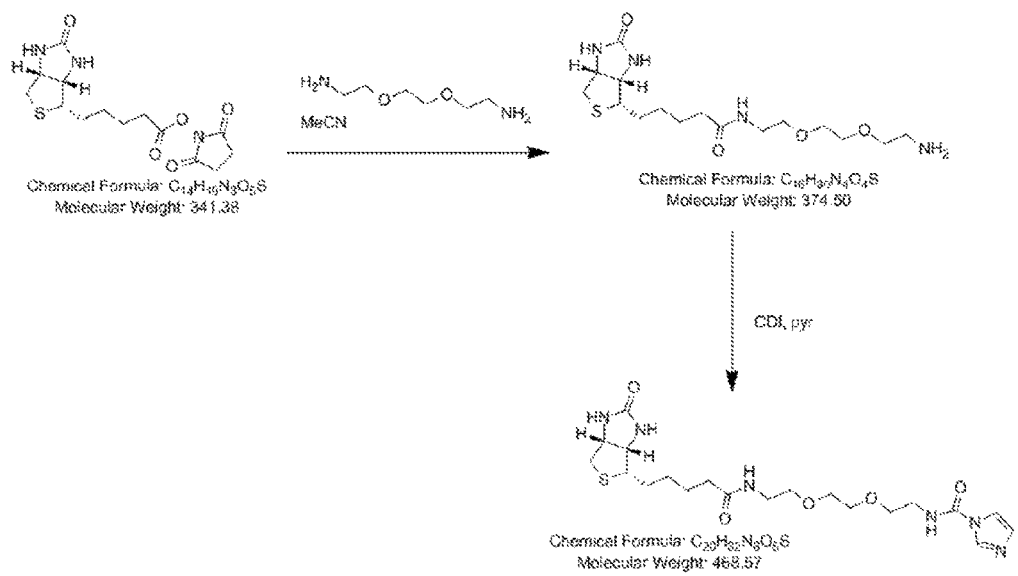

FIG. 35. Scheme II. Synthesis of Biotin-Jeffamine intermediate.

Figure 36:
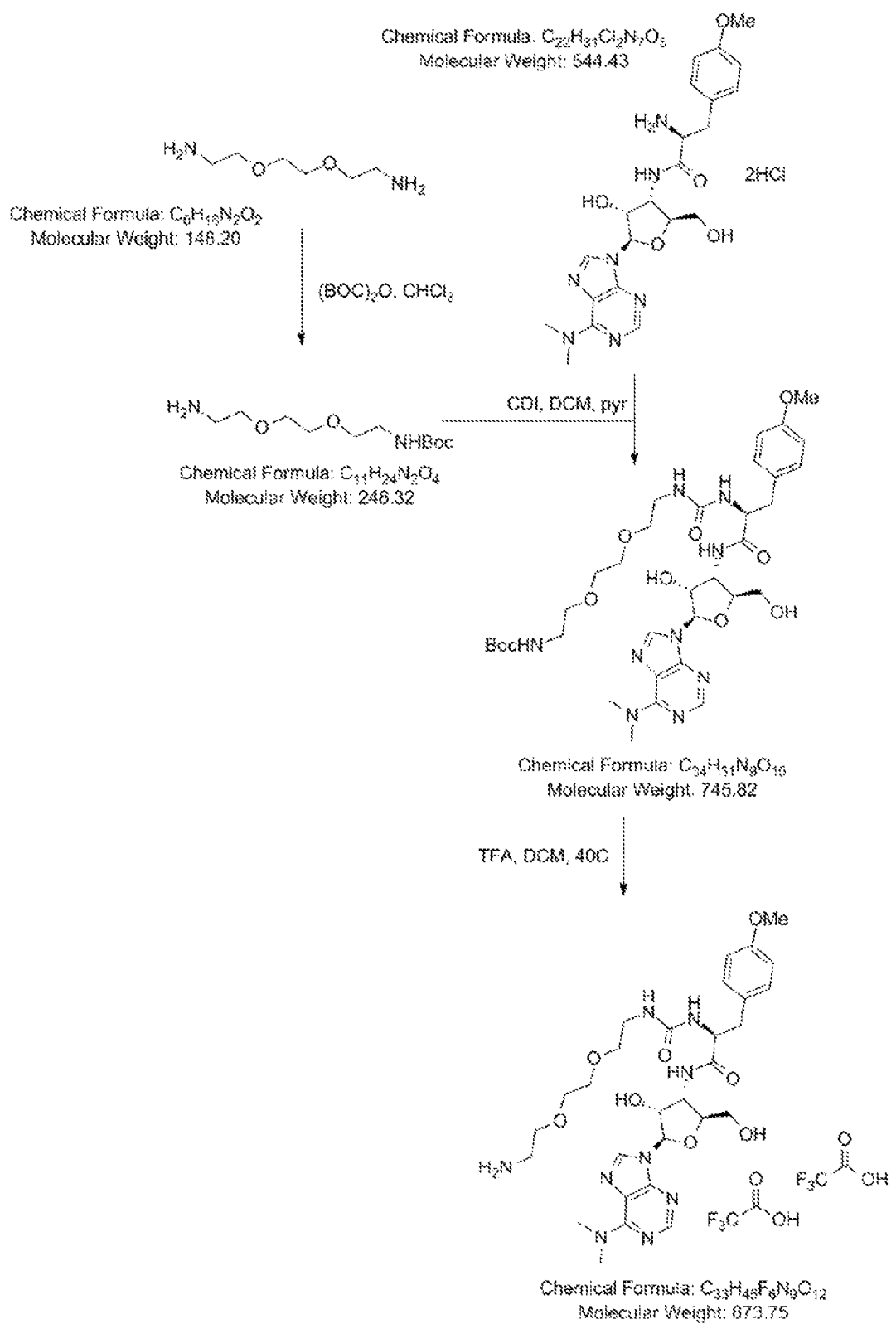

FIG. 36. Scheme III. Synthesis of puromycin-jeffamine intermediate.

Figure 37:
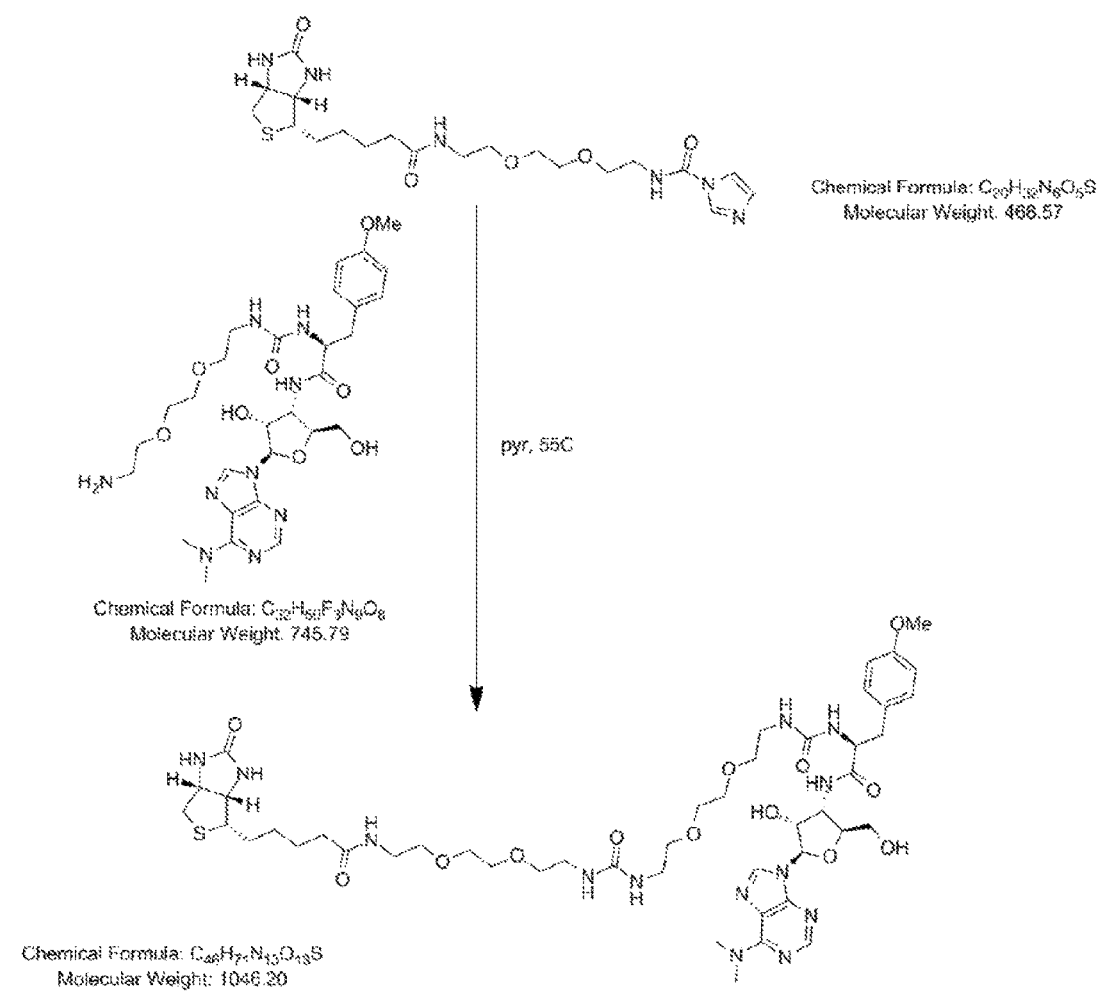

FIG. 37. Scheme IV. Final synthesis of 3P.

Figure 38:
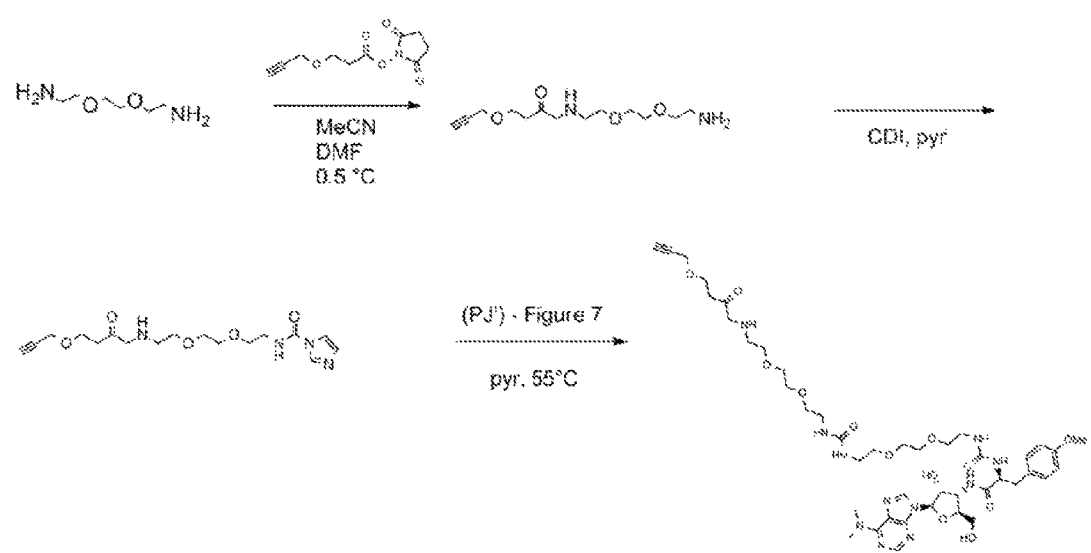

FIG. 38. Scheme V. Synthesis of the alkyne-3P molecule, called 3PP.

Figure 39:
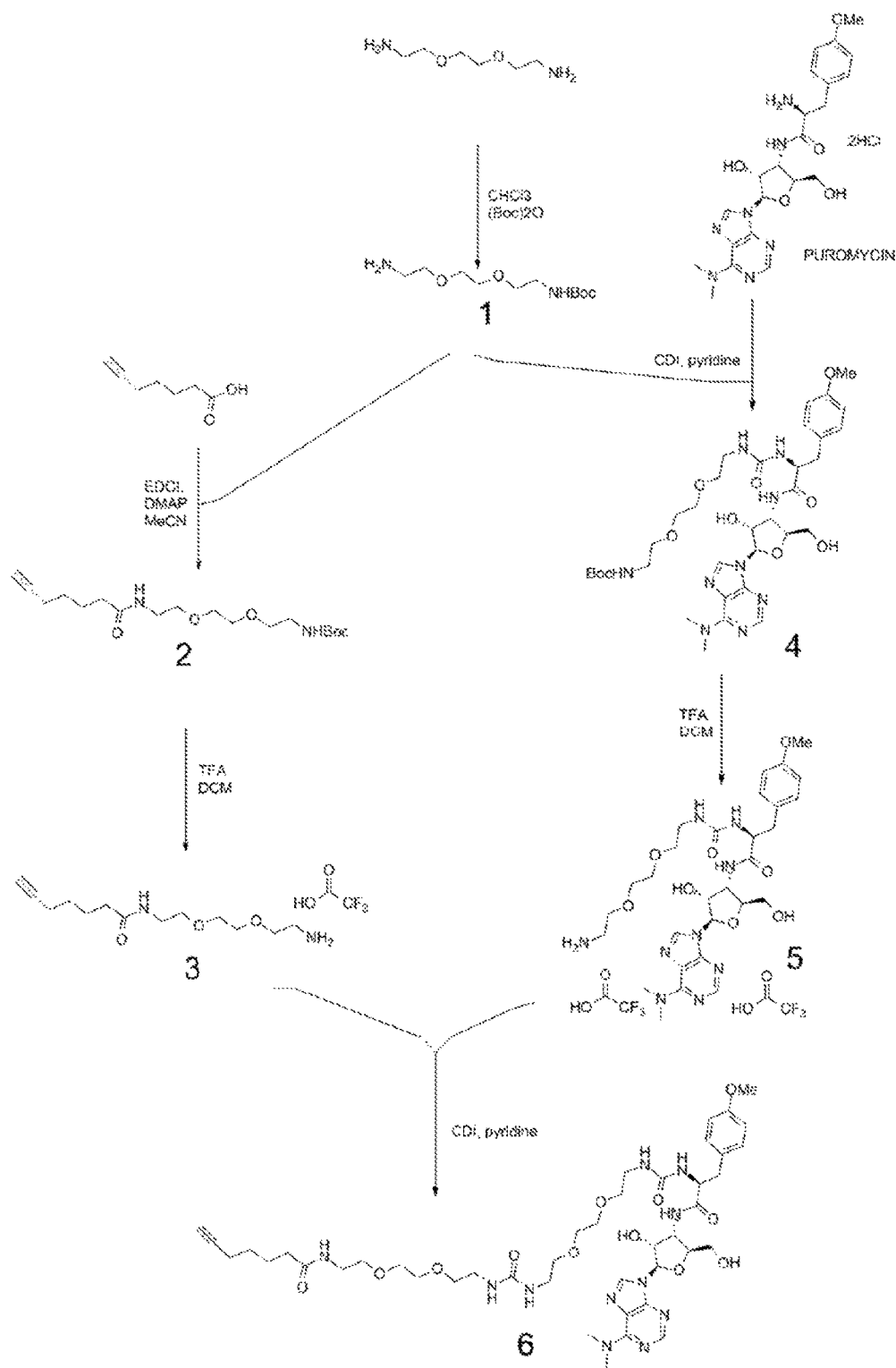

FIG. 39. Scheme Va. An additional synthetic route of 3PP.

Figure 40:
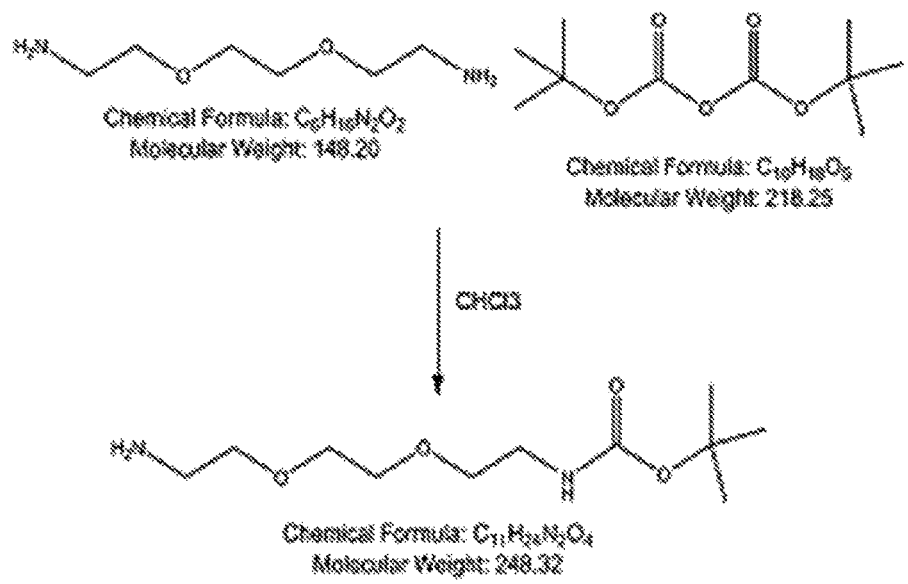

FIG. 40. Scheme A. Synthesis of $C_{11}H_{24}N_2O_4$. The 2-[2-(2-aminoethoxy)ethoxy]ethanamine react with Boc anhydride to generate the desired mono-Boc protected amine $C_{11}H_{24}N_2O_4$.

Figure 41:
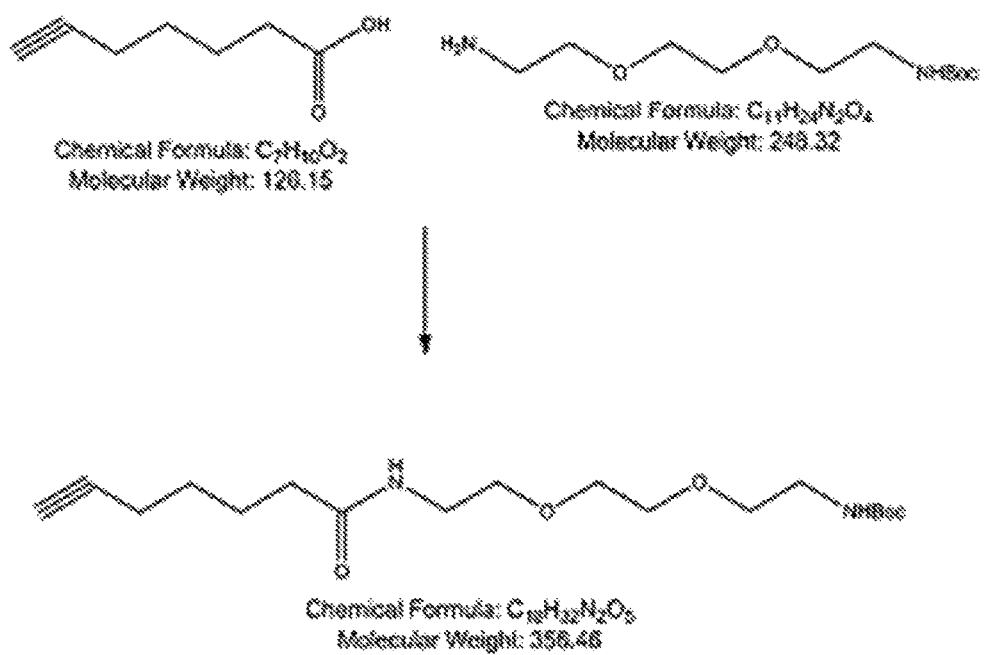

FIG. 41. Scheme B. Synthesis of $C_{18}H_{32}N_2O_5$. The mono-Boc protected amine $C_{11}H_{24}N_2O_4$ is coupled with the hept-6-ynoic acid to form the desired amide $C_{18}H_{32}N_2O_5$.

Figure 42:
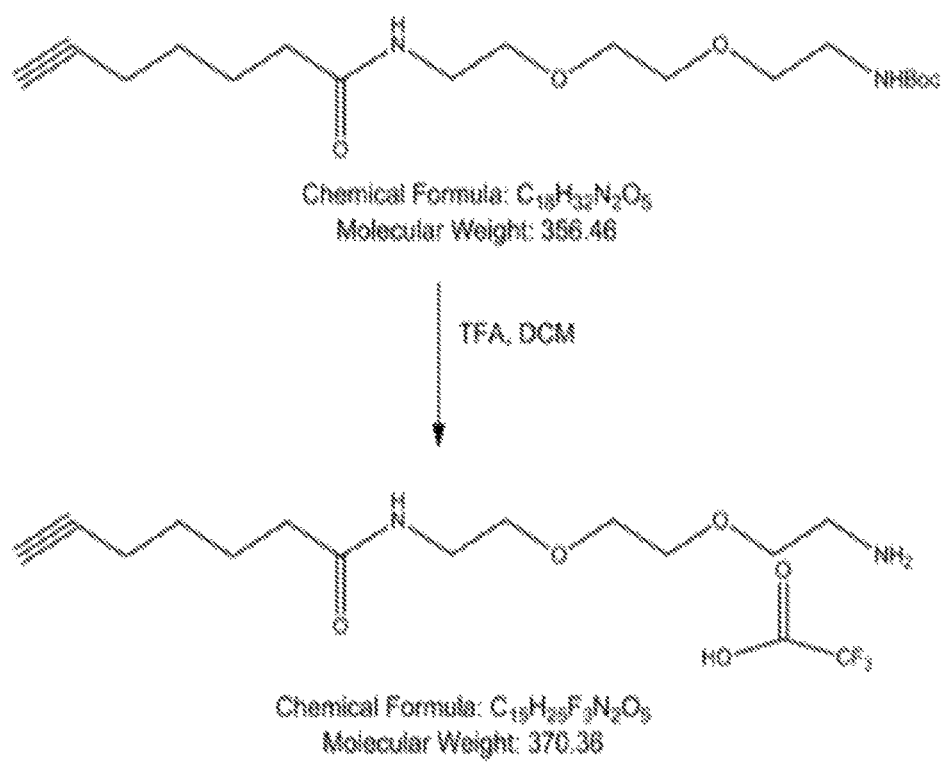

FIG. 42. Scheme C. Synthesis of $C_{15}H_{25}N_2O_5$. Release of the protective group to generate the the amine TFA salt.

Figure 43:
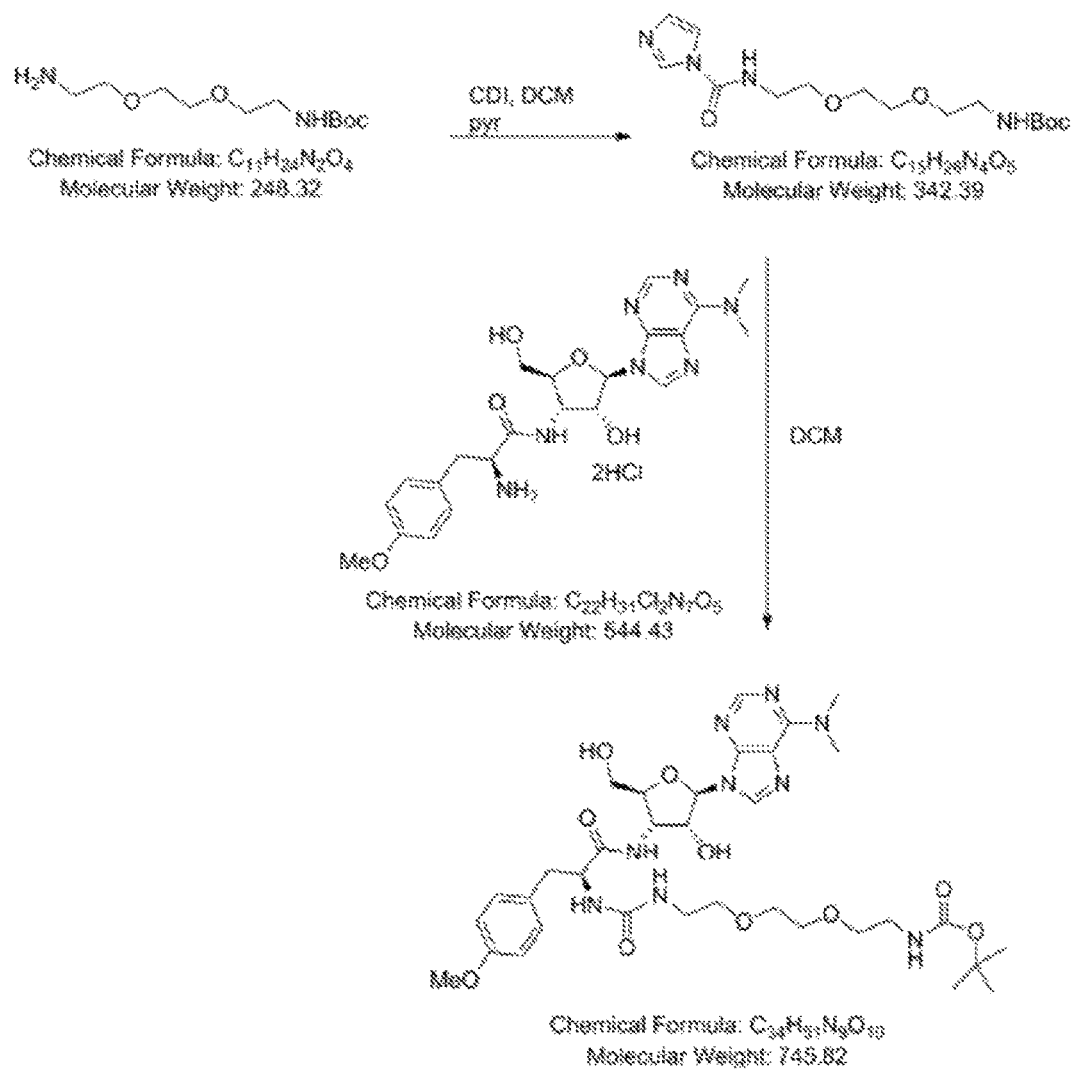

FIG. 43. Scheme D. Synthesis of $C_{34}H_{51}N_9O_{10}$. The mono-Boc protected amine react with CDI in pyridine and then with puromycin to yield the desired derivative.

Figure 44:
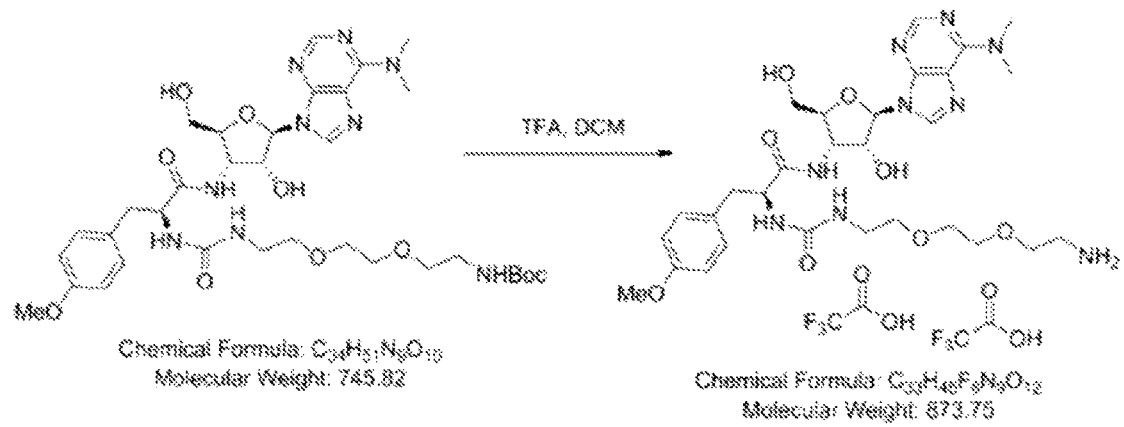

FIG. 44. Scheme B. Synthesis of $C_{33}H_{45}F_6N_9O_{12}$. The Boc amine is deprotected by pure TFA to yield the amine TFA salt as a clear colorless oil.

Figure 45:
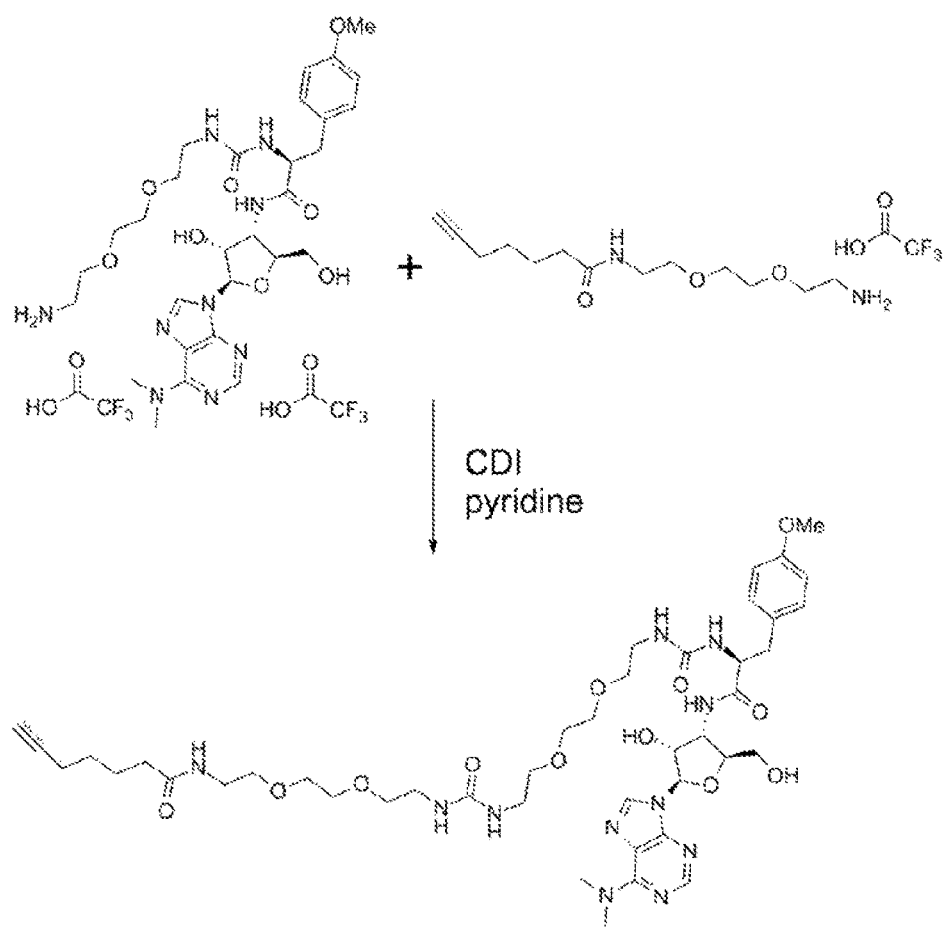

FIG. 45. Scheme F. Synthesis of $C_{43}H_{65}N_{11}O_{12}$. The amine TFA salt $C_{15}H_{25}N_2O_5$ in pyridine react in the presence of CDI with the crude puromycin amine TFA salt. The resulting product is purified by column chromatography to obtain $C_{43}H_{65}N_{11}O_{12}$ (3PP).

Figure 46:
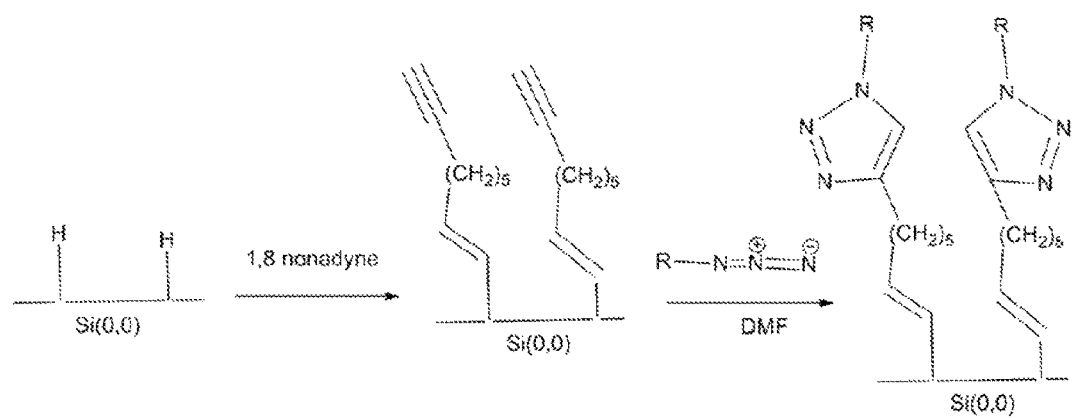

FIG. 46. Scheme VI. Functionalization of a solid surface and binding of the molecule on a functionalized (receptor like) solid surface: Route A (the alkyne on the solid surface coupling an azide-3P molecule).

Figure 47:
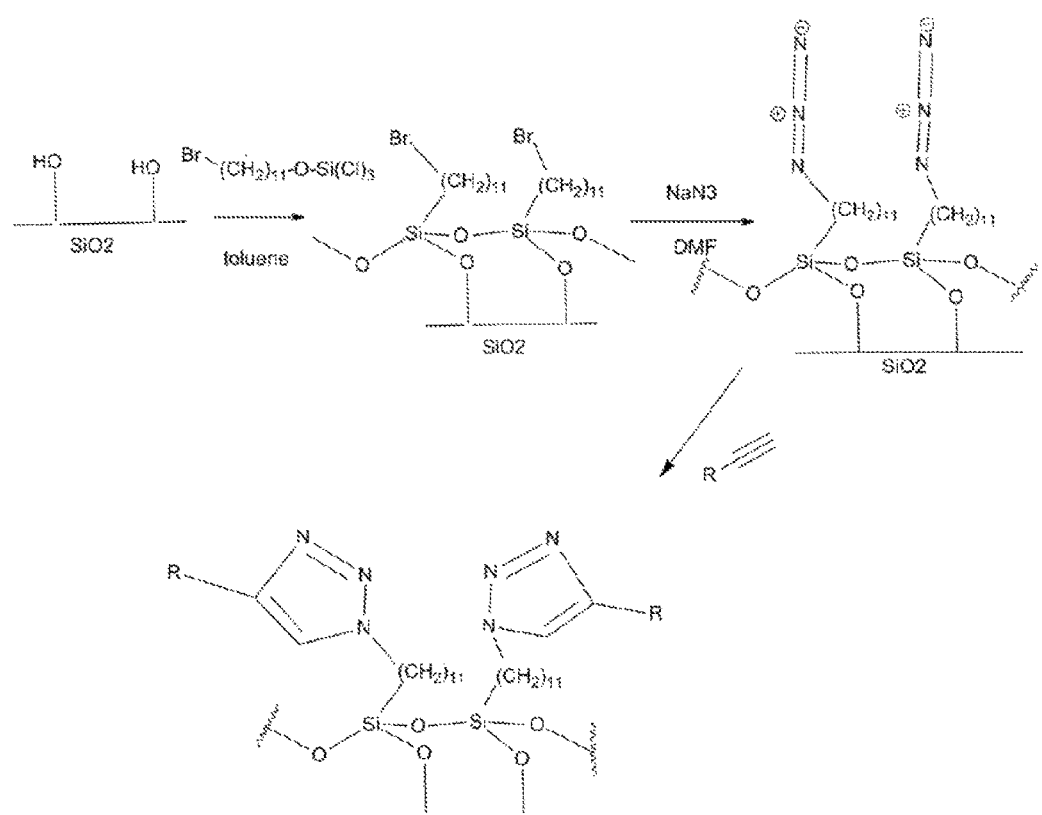

FIG. 47. Scheme VII. Functionalization of a solid surface and binding of the molecule on a functionalized (receptor like) solid surface: Route B (the azide on the solid surface coupling the alkyne-3P molecule).

DETAILED DESCRIPTION OF THE INVENTION

In the following description, numerous specific details are given to provide a thorough understanding of embodiments. The embodiments can be practiced without one or more of the specific details, or with other methods, components, materials, etc. In other instances, well-known structures, materials, or operations are not shown or described in detail to avoid obscuring aspects of the embodiments.

Reference throughout this specification to "one embodiment" or "an embodiment" means that a particular feature, structure, or characteristic described in connection with the embodiment is included in at least one embodiment. Thus, the appearances of the phrases "in one embodiment" or "in an embodiment" in various places throughout this specification are not necessarily all referring to the same embodiment. Furthermore, the particular features, structures, or characteristics may be combined in any suitable manner in one or more embodiments. The headings provided herein are for convenience only and do not interpret the scope or meaning of the embodiments.

In the instant description a new puromycin-containing molecule for the isolation of active polyribosomes and ribosomes is disclosed. The new puromycin-containing molecule allows (i) purification of ribosomes, proteins and RNAs associated to polyribosomes from cell lysates and (ii) ribosome profiling studies. We called this technique 'RiboLace'. After purification, the detection of RNAs and isolated proteins associated to polyribosomes can be performed by standard (immunoblotting or RT-qPCR) or 'omics' techniques (LC-MS/MS or RNA-Seq). RiboLace is faster (~2 hours), it requires 30×-20× less material, it is cheaper than standard approaches and it can be rapidly used to generate a qualitative or quantitative snapshot of the translatome from any cellular lysate.

With the exception of sucrose gradient fractionation, there are not currently other techniques commonly used for the versatile isolation of polyribosomes from biological samples. More importantly, there are no techniques that can selectively capture native polyribosomes in active translation without the use of antibodies.

The present description is the first example of antibody-free and tag-free isolation of native polyribosomes and ribosomes under active translation. The use of the new puromycin containing molecule is preparatory to traditional 'omics' analyses. It substitutes the traditional sucrose gradient purification and it opens up new applications in both research and diagnostics; therefore, the results witnessed in the instant description have practical as well as basic implications.

According to an embodiment, the present description concerns a molecule of general formula (I):

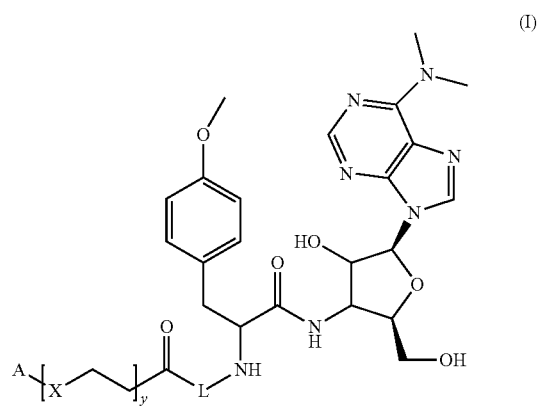

wherein

A is selected from a receptor or a ligand of a receptor-ligand system;

X is selected from an oxygen atom (O) or a carbon atom (C);

y is an integer number from 0 to 10;

L is a molecule of general formula (VI):

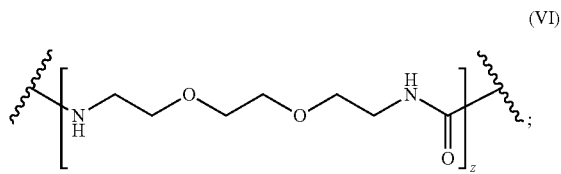

Z is an integer number comprised in the range 2 to 10; and enantiomers thereof.

The end groups NH and NH—C(O) of residue L are linked to C(O) and NH groups of formula (I), respectively, as shown in formula (Ia):

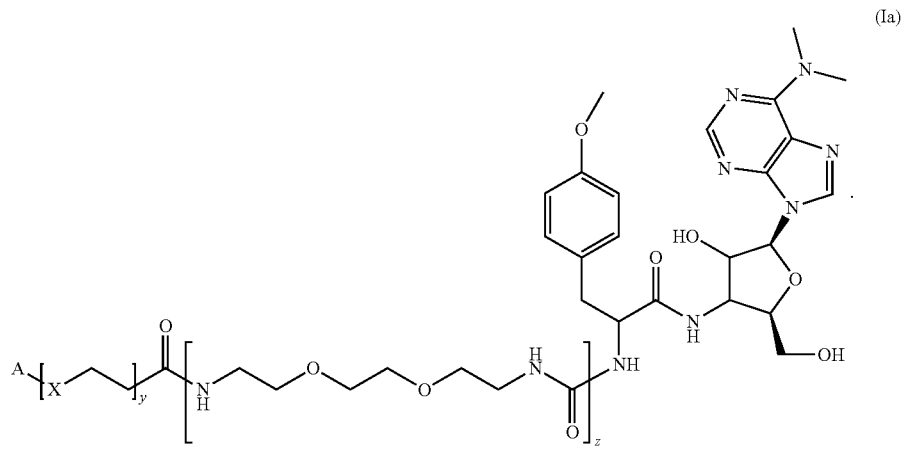

(Ia)

According to an embodiment, 'A' is a reactive group able to bind a solid phase (by means of covalent or not covalent bonds, being selected from a ligand or a receptor of a receptor-ligand system) to provide a sufficient density of molecules onto the solid phase to effectively allow binding of active ribosomes.

According to a preferred embodiment, the ligand-receptor system is selected from: biotin-avidin, biotin-streptavidin, biotin-neutravidin, alkyne residue-azide residue.

In a still preferred embodiment, 'A' is selected from the following groups:

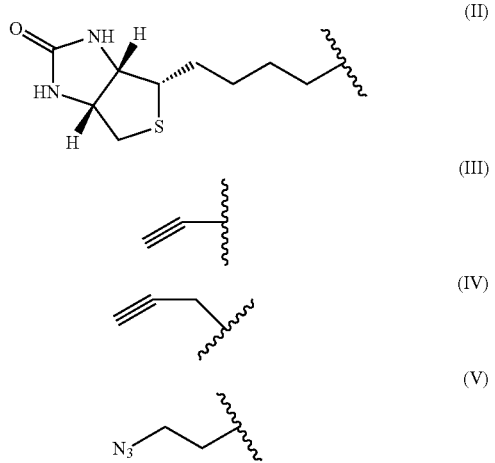

wherein formula (II) represents a molecule containing a biotin (II), formulas (III) and (IV) represent an alkyne residue, formula (V) represents an azide residue (V).

Figure 1:
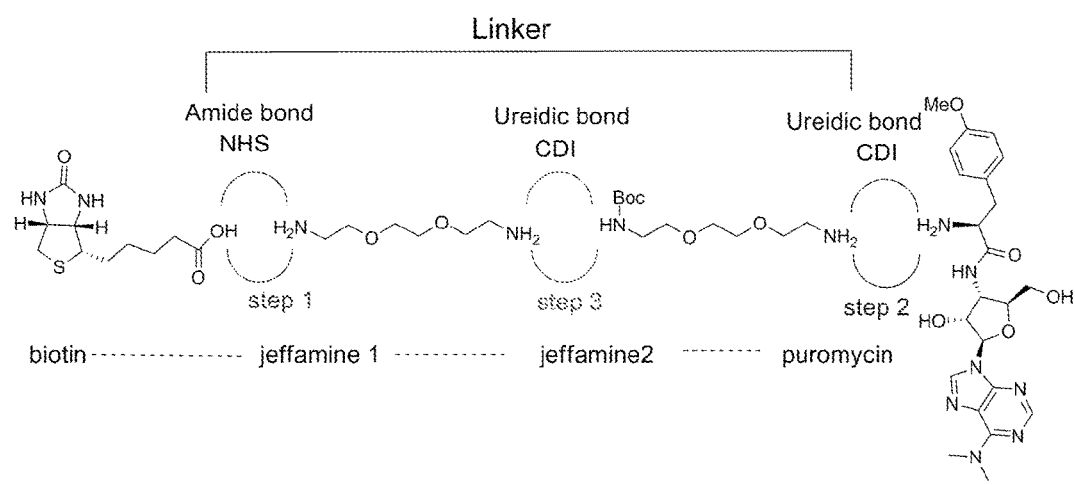
FIG. 1. Scheme of the 3P structure. Biotin is the residue binding the surface; two 2,2'-ethylenedioxy-bis-ethylamine units form the 'L' linker and puromycin is the residue binding the ribosome. NHS, N-hydroxysuccinimide; CDI, N,N'-Dicyclohexylcarbodiimide, jeffamine, 2,2'-ethylenedioxy-bis-ethylamine.

In preferred embodiments, 'L' consists of two repeated 2,2'-ethylenedioxy-bis-ethylamine units (jeffamines, see Material and Methods for details) with a carbonyl group (CO) as shown in FIG. 1.

The puromycin molecule (at the right hand side of chemical formula (I)) is the moiety active on the ribosome. Puromycin and its derivatives are known to inhibit protein synthesis and disassembling ribosomes subsequent to aminoacylation of the tRNA[46,47] through its primary amino group and to release nascent puromycilated peptide from ribosomes[45]. Here, we chemically protect the α-amino group of puromycin linking the N-BOC protected jeffamine by using the coupling agent carbonyldiimidazole (CDI), as described in Materials and Methods.

Figure 7:
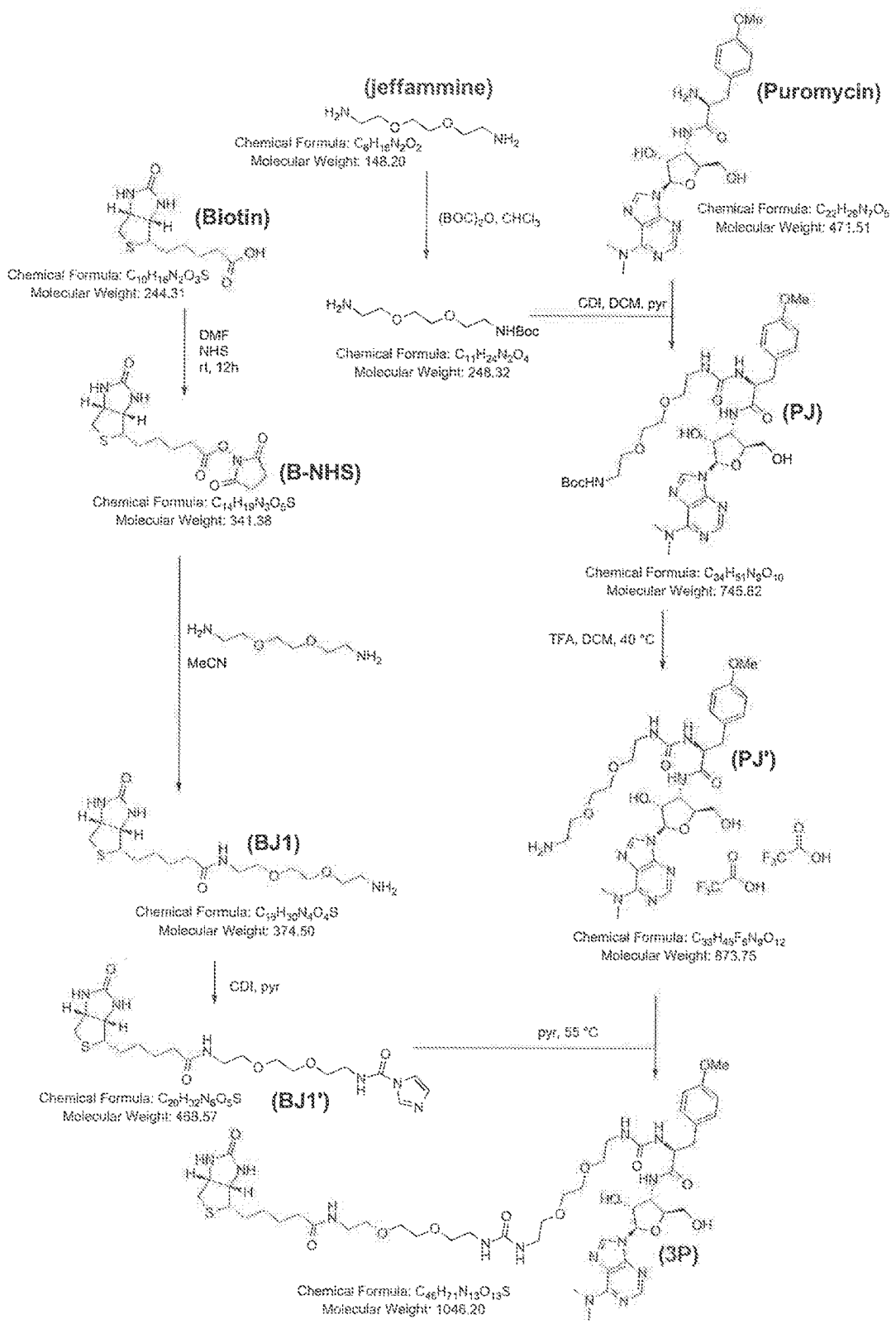
FIG. 7. Full sketch of 3P synthesis.

According to a preferred embodiment, the puromycin containing molecule of formula (I) (named 3P molecule) has been generated from the general formula (I), wherein 'A' has been identified in a biotin residue, 'y' is equal to 0 and n is equal to 2 as shown in FIG. 1. An overview of the complete synthesis is reported in FIG. 7.

The instant description discloses a protocol that integrates the new puromycin containing molecules of formula (I) with a solid phase having a high-binding capacity, optimizing the protocol to an acceptable signal-to-noise ratio for enrichment's analysis of polyribosomes engaged in active protein synthesis.

The new puromycin containing molecule of formula (I) bind a properly functionalized solid phase (i.e. coated with the other of the receptor or the ligand of the receptor-ligand system of residue 'A'), it inhibits translation in a cell-free system when free in solution, it specifically capture transcripts undergoing translation, and it can be used in complex biological samples (i.e. cellular lysate). Without wishing to be bound to any one theory in that regard, the inventors have reason to believe that the instant results suggest that the molecule of formula (I) reversibly binds a puromycin's binding site on the ribosome, most probably in the A site (FIG. 33).

Overall, the use of the new puromycin containing molecules of formula (I) combines at least three important advantages: (i) the need of a small amount of sample ($A_{260}$<45 a.u, meaning ~1/30 of a 300 μL total cell lysate from 80% confluence MCF7 cells in a 100 mm Ø Petri Dish, i.e. 0.75-1.5 $10^5$ cells); (ii) a simple, rapid (~2 hours) and cheap (~5 € per sample) procedure and (iii) a higher accuracy in defining the protein level with respect to the 'gold standard' method.

Finally, we demonstrate the flexibility of this technique, showing that it can be used not only for polysomal profiling, but also for ribosome profiling studies.

Another embodiment of the instant description also encompasses kits for polyribosome isolation/purification and/or ribosome profiling containing the new molecules of formula (I) disclosed herein.

According to an embodiment, the kit includes:

(i) a first reagent containing one or more molecules having the general formula (I). In a preferred embodiment, the molecules are in a dry solid state. Addition of aqueous sample to the first reagent containing vial results in the solubilization of the dry reagent, causing it to interact with the biological material; and (ii) a solid phase suitable for the functional binding of the active molecules of formula (I) and consequently for the separation of polyribosomes from a solution of any biological sample. The solid phase is characterized by its binding capacity, being the solid phase functionalized with the other of the receptor or the ligand of the receptor-ligand system. Preferably, the solid phase is functionalized with one of: streptavidin, neutravidin, avidin, azide residue, alkyne residue.

The binding capacity of the solid phase toward the active molecule of formula (I) has to be higher them 10 pmol/μg, preferentially higher than 200 pmol/μg. When mixing the first reagent (bound to the solid phase) with the biological sample, the latter may be concentrated (measured by absorbance units at 260 nm) from 0.002 a.u./μL to 2 a.u./μL. The measurement wavelength can be suitably selected from the range of 230 to 300 nm, preferably in the range of 240 to 250 nm. The measurement is preferably performed with an optical apparatus capable of measuring the intensity of absorbance of light.

The incubation time of the biological sample with the first reagent may be from 10 minutes to 24 hours, preferentially between 20 minute and 1.5 hours.

In a further embodiment, the kit may comprise at least one of:

(iii) a solubilization solution that can be used to solubilize the active molecule to allow a proper binding on the solid surface. This solution may have the following composition: 2 M NaCl, 1 mM EDTA, 10 mM Tris-HCl, pH 7.5 in DEPC water; with or without ethanol (ethanol/water 1:1); with or without copper (II); with or without sodium ascorbate; with or without a ligand of copper (preferably a triazolylmethylamine derived molecule, such as the Tris(3-hydroxypropyltriazolylmethyl)amine, #762342, Sigma-Aldrich).

(iv) an incubation solution that can be used for an optimized incubation of polyribosomes with the functionalized solid surface. This solution may have the following composition: 10 mM NaCl, 10 mM MgCl$_2$, 20 μg/ml cycloheximide, 10 mM Hepes, pH 7 in DEPC water. The incubation time may be from about 10 minutes to 24 hours, preferentially between 20 minute and 1 hour. The incubation temperature may be between 1 and 25° C., preferentially between 1 and 7° C.;

(v) a washing solution that can be used to wash out unspecific bounded molecules. This reagent may have the same composition of the iv reagent; with or without detergents (preferably selected from: Tween 20, Triton x-100 and 4-Nonylphenyl-polyethylene glycol, in concentrations from 0.001% to 5%, preferentially between 0.01% and 1%).

(vi) if the solid phase is not RNase-free, the kit may additionally contain an RNase eliminating solution and a resuspension solution for removing RNase from the solid surface, to be used before or after functionalization with active molecules. The RNase eliminating (A) and resuspension (B) solutions may have the following compositions: (A) 0.05 M NaCl, 0.05-1 M NaOH, in DEPC-treated water, preferably the concentration of NaOH is between 0.05 M and 0.2 M, more preferably is about 0.1 M; and (B) 0.05-1 M NaCl, in DEPC-treated water, preferably the concentration of NaCl is between 0.05 and 0.2 M, more preferably is about 0.1 M;

(vii) the kit may additionally contain equipment for preparing the sample, a timing means and a buffer for diluting/resuspending the sample;

(viii) the kit may additionally contain a negative control against which the result obtained with the active molecule (general formula I) may be compared. The negative control can be:

(1) a molecule with the general formula (VII):

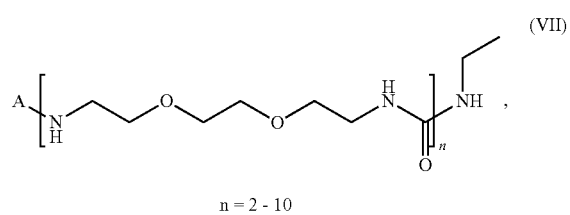

n = 2 - 10 or (2) a molecule with the general formula (VIII) with n=18-25 or a molecule with a molecular weight equal (±500 Dalton) to the molecule of general formula (I):

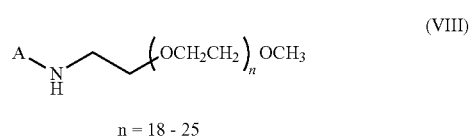

n = 18 - 25 wherein the molecules of formula (VII) or (VIII) are coated onto the solid phase.

In both cases 'A' has identical meanings as in the general formula (I).

(ix) detailed instruction for easy use of the kit.

The kit disclosed in the present description can be utilized mixing the first reagent with the solubilizing solution and the solid phase. Once the first reagent is bound to the solid phase, a proper dilution of the biological simple in the incubation solution can be prepared and mixed with the solid phase bound to the first reagent. After incubation, the solid phase is separated from the solution, washed with the washing solution and the isolated active polyribosomes can be analysed by extraction of RNAs and/or proteins.

The kit can be used with different methods:
1) for isolation of active polyribosomes for functional studies on polyribosome-associated molecules (i.e. RNAs and proteins);
2) for identification of mRNA whose translation is modulated in response to a stimulus;
3) for ribosome-profiling studies, a method used to study gene expression translation regulation.

In all methods (extensively described in the section 'results') an internal negative control may be included in order to perform an enrichment analysis.

The first method comprises; (a) contacting a lysate of a population of cells with the first reagent properly bound to the solid phase; (b) allowing the reagent to selectively bind to the ribosomes in active translation; (c) isolating polyribosomes bound to the reagent and the associated RNAs and proteins; (d) isolating RNAs or proteins for functional studies on selected targets.

The second method comprises the following steps: (a) contacting a lysate of a population of cells with the first reagent properly bound to the solid phase; (b) allowing the reagent to selectively bind to the ribosomes in active translation; (c) isolating polyribosomes bound to the reagent and the associated RNAs and proteins; (d) determining the identity and the amount of the mRNAs (e.g. by RNA-seq analysis) in the isolated material; (e) determining the identity and the amount of the mRNAs in a biological control sample; and (f) comparing the amount of mRNA of 'd' to the amount of the mRNA of 'e', thereby identifying mRNA whose translation expression is modulated in response to the stimulus.

In an alternative embodiment, the lysate is added to the solid phase, only after incubating the first reagent with the cell lysate and binding of the first reagent to active ribosomes contained in the lysate.

The third method comprises the following steps; (a) preparation of the first reagent properly bound to the solid phase; (b) contacting a lysate of a population of cells (previously digested with RNase I and then treated with an RNase inhibitor) with the first reagent bound to the solid phase; (c) allowing the first reagent to selectively bind to the active ribosomes; (d) isolating ribosomes bound to the first reagent and the associated mRNA fragments; (e) depleting ribosomal RNA and isolating mRNA fragments; (f) purification of the fragments after extraction from a denaturing SDS-PAGE gel; (g) sequencing and mapping back to the genome the fragments, in order to reveal the translation level of each gene, as well the position of ribosomes along the mRNA.

According to an embodiment, the solid phase can be selected from: agarose beads, agarose-acrylamide beads, cellulose beads, iron oxide beads, graphene beads, silica or silica mixture beads, polystyrene beads, polycarbonate beads, polypropylene beads and/or combinations thereof.

According to a preferred embodiment, the solid phase can be embedded in microwells.

According to a preferred embodiment, the solid phase is in the form of microbeads.

Here, examples of the biological sample include in vitro cell-free lysates or any lysate from bacterial, archaeal or eukaryotic cells, including human cells. All methods do not need the expression of ectopic proteins and hence allow for a new way to map the functional organisation of gene expression. Reagents, methods, and kit described will be further understood with reference to the following non-limiting examples.

Results

Synthesis of the 3P Molecule.

Puromycin analogues have been extensively used (i) to characterised the peptidyl transferase centre in co-crystal structures with the bacterial ribosome[31,36,49], (ii) to capture newly synthesised peptides[21,44] or (iii) to detect protein synthesis in cells[50].

Here, we designed a new molecule (herein referred as 3P) having the chemical structure shown in general formula (I). In this structure 'A' is a biotin chemical group, able to bind to a streptavidin-functionalized solid phase; 'y' is equal to 0; the 'L' moiety is represented by two 2,2'-ethylenedioxy-bis-ethylamine units (herein referred as jeffamine units), and puromycin is the moiety binding the ribosome (FIG. 1).

Figure 2:
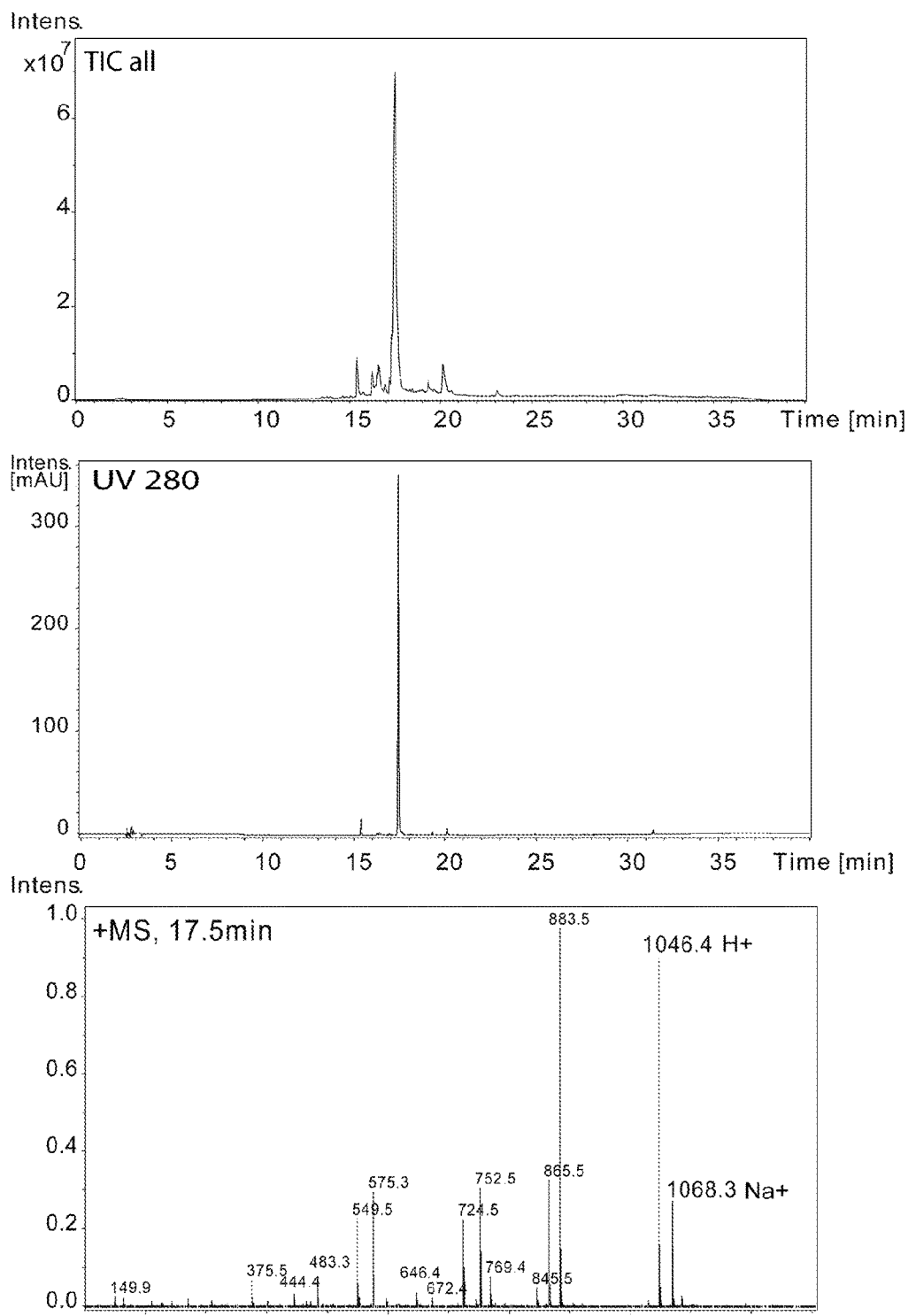
FIG. 2. LCESI-MS analysis of the 3P molecule
Top: Total ion current (TIC) chromatogram (top) and UV chromatogram at λ280 nm (middle) were obtained by using an RP18 column (Phenomenex Kinetex, #00G-4601-E0; 5 μm C18 100 Å-250×4.6 mm), eluent 98% water 2% acetonitrile for 5 min; then to 100% acetonitrile in 35 min. Peak at 17.5 min (bottom) shows ESI(+)MS (Ion Trap mass analyzer) full scan mass spectrum in agreement with the reported structure. In particular $[M+H]^+$ at m/z 1046.5 is consistent with its molecular formula $C_{47}H_{72}N_{11}O_{14}S^+$.
Figure 3:
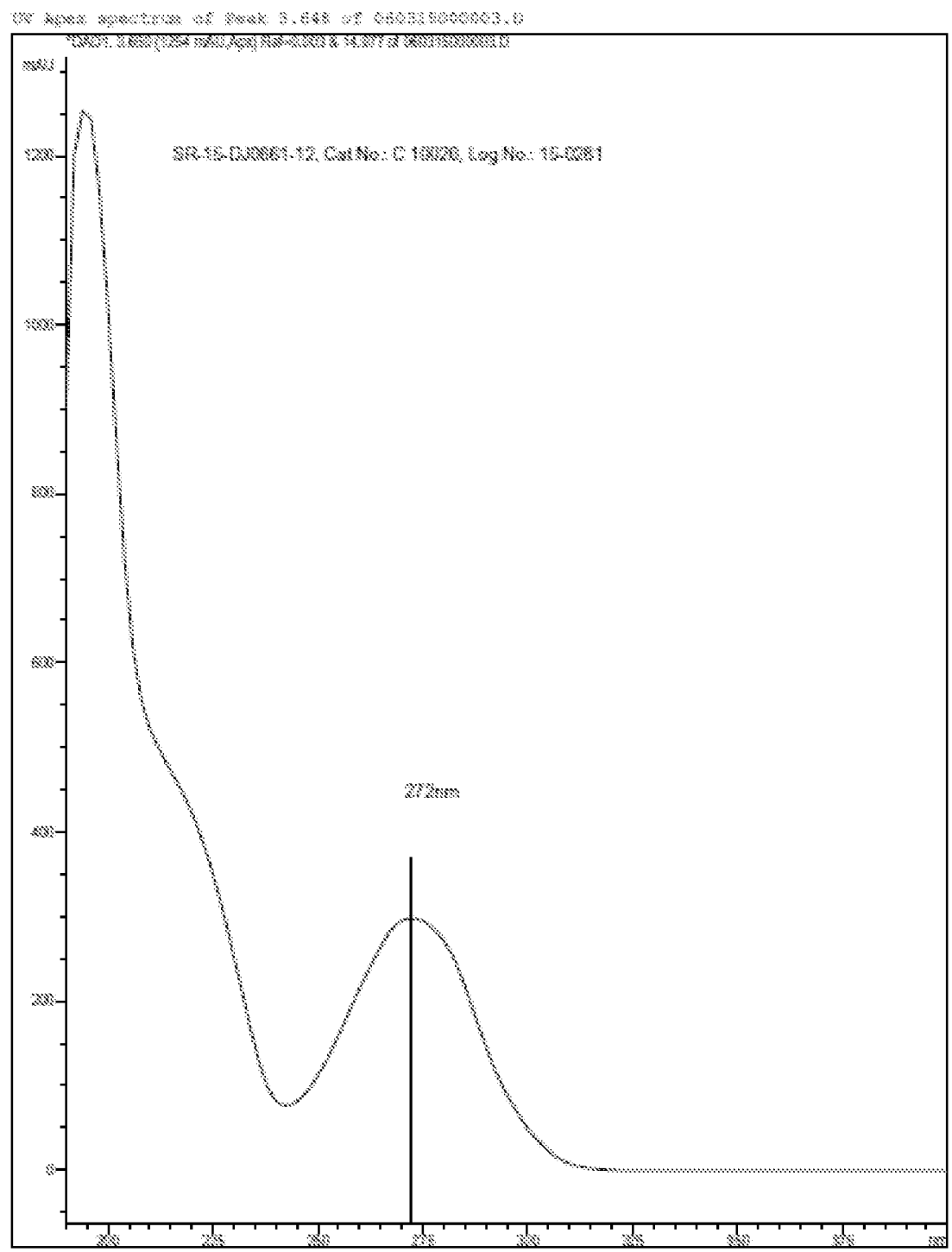
FIG. 3. UV-VIS spectra of the 3P molecule
UV spectrum of major peak (3P) in the chromatogram shown in FIG. 2 as taken on line by Photo Diode Array.
Figure 4:
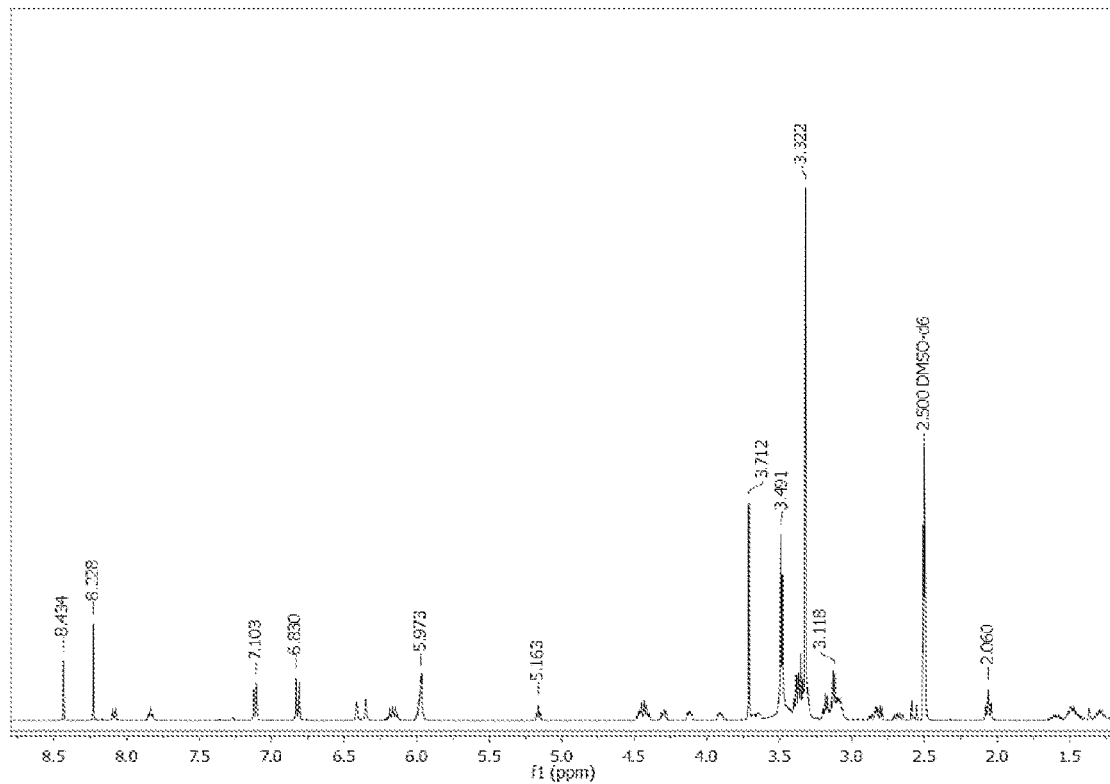
FIG. 4. $^1$H-NMR spectra of the 3P molecule
400 MHz 1H-NMR spectrum of a 5 mM solution of 3P in DMSOd6 (residual signal used as reference for ppm scale calibration $\delta_H$=2.50 ppm) as detected at 300K; relaxation delay 20 sec, pulse width 8 μsec, number of transients 128.
Figure 5:
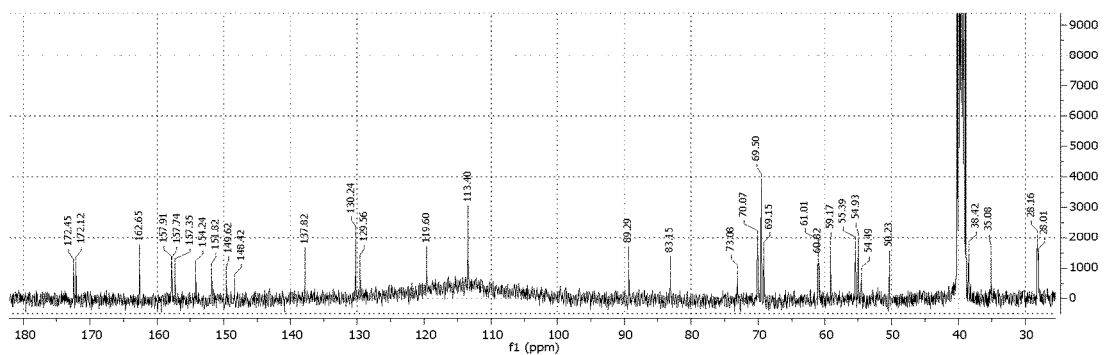
FIG. 5. $^{13}$C-NMR spectra of the 3P molecule
100 MHz 13C-(1H decoupled) NMR spectrum of a 5 mM solution of 3P in DMSOd6 (residual signal used as reference for ppm scale calibration $\delta_C$=39.5 ppm) as detected at 300K; relaxation delay 10 sec, pulse width 15 μsec, number of transients 5600.
Figure 6:
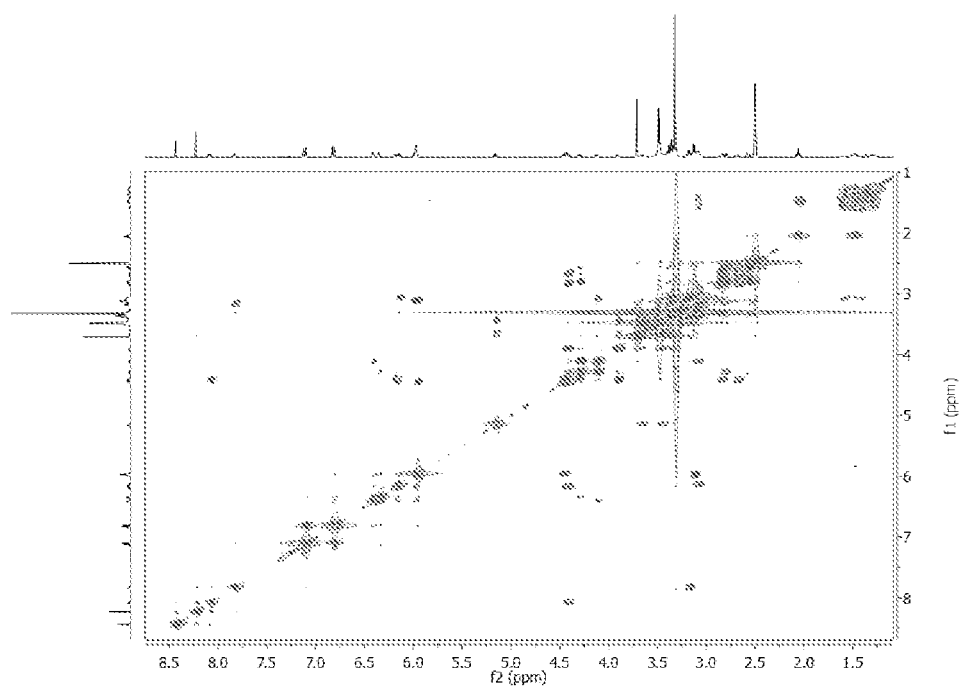
FIG. 6. COSY spectra of 3P
400 MHz 1H-1H COSY-NMR of a 5 mM solution of 3P in DMSOd6 (residual signal used as reference for ppm scale calibration $\delta_H$=2.50 ppm) as detected at 300K; relaxation delay 3 sec, 2048×512 acquisition matrix.

In order to hamper the nucleophilic attack of the primary amino group of puromycin to the ester group on the peptidyl-tRNA (in the P-site), the α-amino group of puromycin was covalently linked to one side of a N-BOC protected jeffamine by using the coupling agent carbonyldiimidazole (CDI); on the other side, biotin (activated as its N-hydroxysuccinimide ester derivative) was amidated at the carboxylic terminal group with the same jeffamine unit. Coupling of the two jeffamine units installed between biotin and puromycin moieties afforded the targeted product 3P at purity higher than 90% (FIG. 2). The $^1$H-NMR (400 MHz, DMSO-d$_6$), $^{13}$C-NMR (100 MHz, DMSO), ESI-MS and Ion Trap mass analyser are in agreement with the molecular formula ([M+H]+ at m/z 1046.5, $\lambda_{max}$ 272 nm;) as described in FIGS. 3, 4, 5 and 6. An overview of the complete synthesis is reported in FIG. 7 (see Materials and Methods for details on the synthesis). The product 3P was used as such in all the further bioassays.

3P Molecule: Binding, Activity and Protocol for Users.

Binding on a Streptavidin Coated Solid Surface

Figure 8:
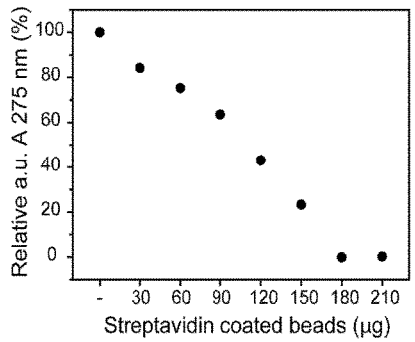
FIG. 8. 3P depletion with streptavidin coated magnetic beads. Absorbance (a.u., 275 nm) of the supernatant is measured after addition of streptavidin coated magnetic beads. Beads are pulled down with a magnetic rack. Increasing quantities of beads cause a progressive reduction of the 3P free in solution (measured with Nanodrop ND-1000 UV-VIS Spectrophotometer). Data represent the mean of triplicate experiments (n=3).

To verify the activity of the biotinylated moiety of the 3P molecule, we tested its binding activity on streptavidin-coated magnetic beads. Increasing quantities of streptavidin coated magnetic beads (Dynabeads, Life Technologies #65001) are suspended in 50 μL of a solution containing 1 mM 3P in 2 M NaCl, 1 mM EDTA, 10 mM Tris-HCl, pH 7.5 in DEPC water. Since 3P has the characteristic UV-VIS spectra of puromycin, with a specific absorbance at 272 nm, we evaluated its binding activity by monitoring the subtraction of 3P from the solution (FIG. 8) after coupling it with the surface (see Materials and Methods for the detailed procedure). We defined for 3P a binding capacity of ~250 pmol/μg. A solution of 1 mM can saturate ~200 μg of beads. This result demonstrates the functional activity of the biotin functional group and allowed us to define a 3P/beads ratio higher than 5 (3P, molexl$^{-1}$; beads, g) as working condition for beads functionalization in all further experiments.

In Vitro Activity of 3P Toward Polyribosomes and their Loaded Transcripts

Figure 9:
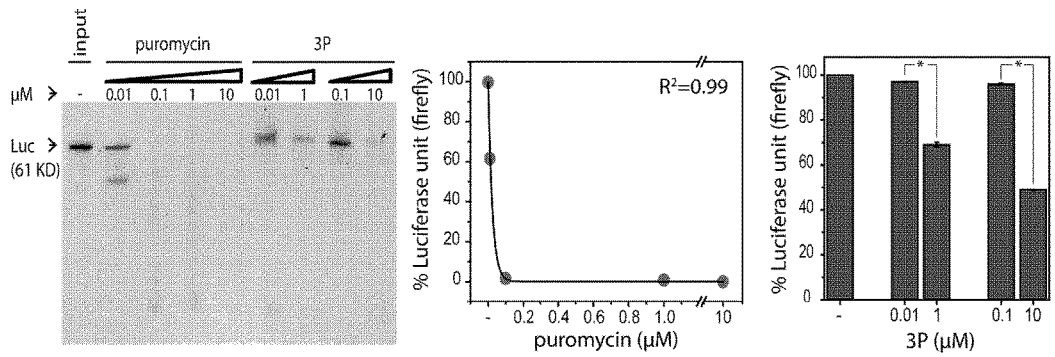
FIG. 9. Effect of 3P and puromycin on in vitro-cell free expression of the luciferase gene. Luciferase protein production in the presence of different concentrations of puromycin and 3P (left panel). The firefly luciferase is expressed in vitro (90 min) adding z-labeled biotinylated lysine-tRNAs to the reaction. After incubation with streptavidin-HRP, the protein is visualized by chemiluminescence. The scatter plot shows the inhibition of luciferase expression in the presence of different concentrations of puromycin (0 μM, 0.01 μM, 0.1 μM, 1 μM and 10 μM (central panel). Black line: best fit that describes the decay of luciferase expression as a function of puromycin concentration (y=A*exp(-x/b), were A=100 and b=0.020±0.003). The histogram shows the inhibition of luciferase expression in the presence of different concentrations of 3P (0 µM, 0.01 µM, 0.1 µM, 1 µM and 10 µM (right panel). Final volume, 50 µL; error bars represent s.d. calculated from triplicate experiments (n=3); (*)=t-test p-val<0.01.

To date, no structural data are available for puromycin binding in complex with the eukaryotic ribosome, while the bonding of a puromycin derivative in bacterial ribosome is well described[49]. Since the newly synthesised 3P molecule is functionalized with an inhibitor of protein synthesis, we tested the inhibitory effect of 3P on translation. In particular, we tested the effect of 3P on an in vitro-cell free translation system (hereinafter called "IVTT euk-mix": TNT Quick coupled Transcription/Translation System, Promega #L2881) using a firefly luciferase gene (Promega #L4741). We compared the 3P competitive activity with the inhibitory effect of puromycin. After 90 minutes of incubation, we monitored the protein production by SDS-PAGE and luminescence assay (FIG. 9). Upon puromycin titration, we observed an exponential decay of the protein synthesis, while 3P can significantly inhibit translation starting from a concentration of 1 μM (FIG. 9, 10).

To evaluate the effect of 3P on a prokaryotic in vitro system and on another protein, namely green fluorescent protein, (FIG. 10b) we expressed EGFP (Enhanced Green Fluorescent Protein) in the aforementioned IVTT euk-mix and in a prokaryotic one (hereinafter called "IVTT pro-mix": E. coli T7 S30 Extract System for Circular DNA, Promega, #L1130). The EGFP gene was cloned into a commercial vector (pBluescript II KS(+), GeneScript), used in the past for both prokaryotic and eukaryotic expression[51,52]. We also tested the effect of a 3P-alkyne variant (3PP) free in solution on EGFP expression. In 3PP, the biotin moiety is substituted with an alkyne moiety (see Scheme V).

Figure 10:
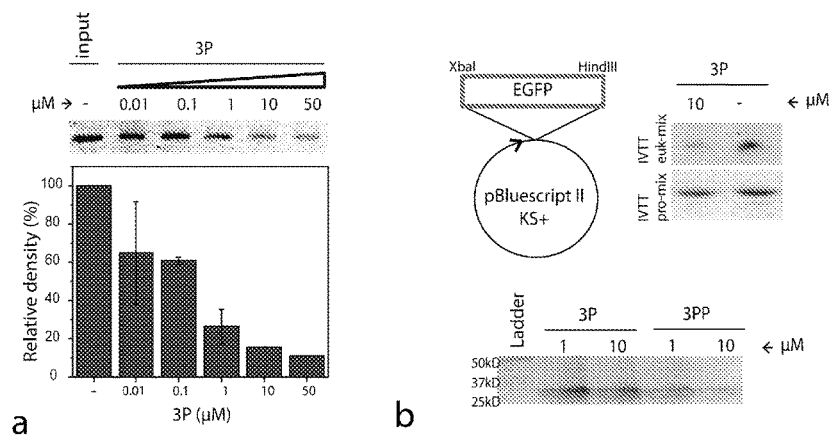
FIG. 10. Expression of the firefly luciferase and the Enhanced Green Fluorescent Protein (EGFP) in the presence of 3P. (a, top), Effect of 3P on luciferase protein expression. ε-Labeled biotinylated lysine-tRNAs is used to monitor the protein production by SDS-PAGE. (a, bottom), Histogram representing the relative quantification (density fold change) of the bands reported in the western blot (up), respect to the control (input, reaction mix without 3P). Reactions are carried out in a final volume of 50 µL of IVTT euk-mix. Error bars represent s.d. calculated from a duplicate experiment; (b, top-left), Scheme of the plasmid used for EGFP expression. Restriction sites used to clone the gene are reported. (b, top-right) The effect of 3P on EGFP expression monitored by Western Blot analysis. Reactions are performed in a final volume of 50 µL of IVTT euk-mix (up) or IVTT pro-mix (down). (b, bottom). Effect of 3P and 3PP on EGFP expression in a IVTT euk-mix.

We observed a clear depression of the protein synthesis in both prokaryotic and eukaryotic systems and the inhibitory effect of the 3P-alkyne variant is consistent with what observed for the 3P molecule (FIG. 10b).

We concluded that 3P can interfere with translation in both eukaryotic and prokaryotic cell-free systems.

Figure 11:
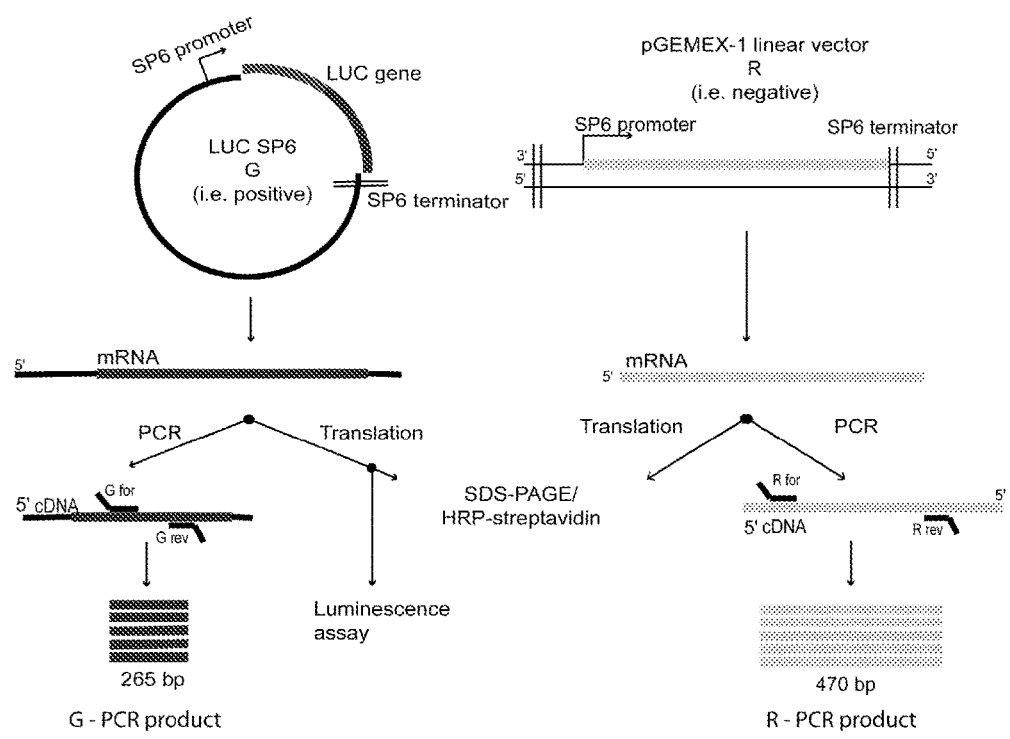
FIG. 11. In vitro transcription/translation, isolation and detection of protein synthesis: scheme of the approached used. (a) Sketch of the two plasmids used as positive (firefly luciferase, LUC SP6, G) and negative (empty pGEMEX vector, R) controls, and overview of vectors and methods used for RNA and protein visualization. PCR, luminescence assay and SDS-PAGE of biotinilated proteins measurements allowed us to detect the expression of the RNAs and the enrichment of the transcripts on differentially functionalized beads. (b) Protocol used to pull-down transcripts produced during cell-free in vitro transcription-translation. From step 1 to 6: (1), Plasmids were added to the in vitro transcription-translation reaction. (2), Beads were functionalized with 3P and mP. (3), After 40 min of incubation, the IVTT euk-mix was added to functionalized beads and incubated for 1 hour in orbital rotation at 2 rpm at 4° C. (4), Beads were washed without detaching them from the magnet to remove unspecific binding. (5/a), After Trizol extraction and isopropanol precipitation, RNA is digested with DNase I (5/b) to avoid possible DNA contaminations and used for cDNA synthesis (5/c). (6), Samples were analyzed by RT-qPCR to detect the presence of the luciferase gene and the negative control transcript.
Figure 12:
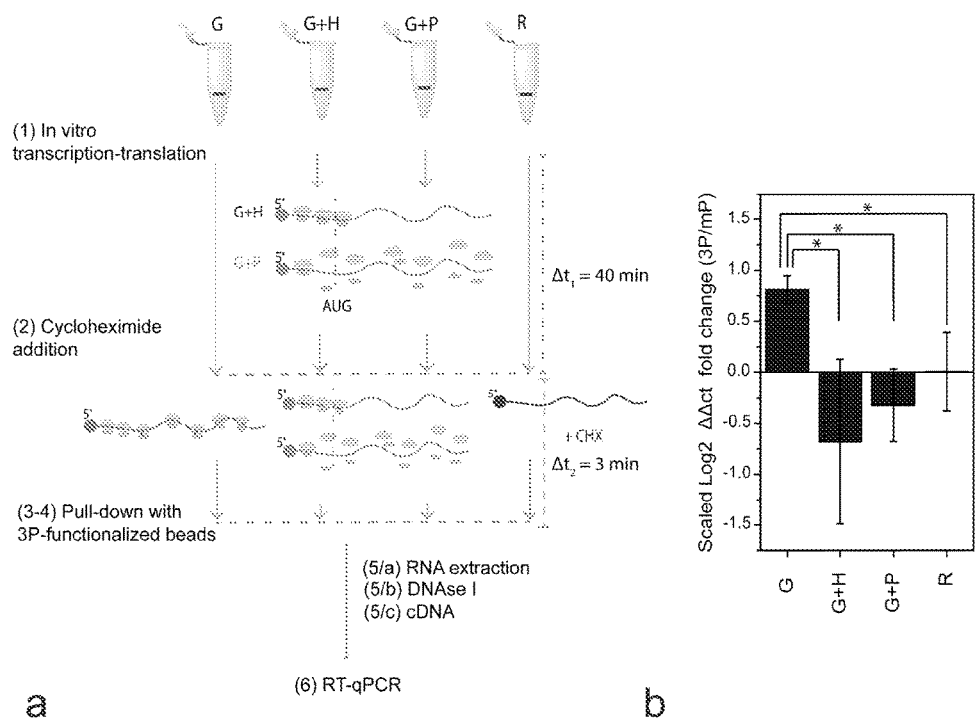
FIG. 12. Selective enrichment of mRNAs in active translation (a) Sketch of experimental protocol. From step 1 to 6: (1), plasmid encoding for firefly luciferase (G) and the negative control (R) plasmids, 0.25 µg each, are transcribed and translated in vitro according to the manufacture's instruction (TNT Quick coupled transcription/translation, Promega). Drugs are added to inhibit translation at time (t)=0. Incubation time (∆t1): 40 min at 34° C. G+H: luciferase gene with harringtonine (H, 2 µg/mL); G+P luciferase gene with puromycin (P, 5 µg/mL). (2), Samples are then incubated with cycloheximide (CHX, 10 µg/ml) for 3 min at 34° C. (3), Ribosomes in active translation are pulled down with 3P- or mP-beads. (4), Beads are separated and washed. (5/a-c), RNA is extracted, treated with DNAse I and retro-transcribed to single stranded cDNA with random hexamers. (6), Equal amount of RNAs (60 ng) from each sample is used for RT-qPCR. A detailed description of the procedure is reported in 'Materials and Methods'. (b) Scaled Log 2 fold change values relative to the total amount of transcript captured by 3P-beads compare to control beads (mP), henceforth referred as the 'enrichment'. (*)=t-test pval=0.03 (G vs G+H), pval=0.02 (G vs G+P), pval=0.04 (G vs R); n=5. Error bars represent s.d. Beads used: Dynabeads, Life Technologies, #65001.

If 3P interacts in the A site in a similar manner as puromycin does (but without covalent binding to the nascent polypeptide chain), we propose the use of 3P to fish active ribosomes out from a crude cell-free extract. To prove this, we first functionalized streptavidin coated beads (150 µg) with 3P, as described above, end-capping sterically inaccessible binding sites with a commercial biotin-methoxypolyethylene glycol conjugate (Creative Pegworks #PLS-2056; herein called mP, 1100 Da, 1 DM working concentration). As a control for unspecific binding (negative control), we functionalized a second batch of beads (150 µg) only with mP (see Materials and Methods for a detailed protocol). We used 3P- and mP-functionalized beads (called 3P-beads and mP-beads respectively) to fish translating ribosomes from an in vitro-cell free transcription/translation mixture containing a reticulocyte lysate (IVTT euk-mix). We optimised a six steps protocol structured as follows (FIGS. 11 and 12):

(1) expression (40 min, at 30° C.) of the gene encoding for the firefly luciferase (G, FIG. 12) inserted in the LUC SP6 control vector (Promega, #L4741) using the coupled transcription/translation kit (Promega #L2881);

(2) addition of cycloheximide (CHX, 10 µg/mL, Sigma #01810) to stall ribosomes during elongation (CHX is widely used to study multiple parameters of translation[20, 53]);

(3) functionalization of the magnetic beads with 3P and mP and addition of 3P-beads and mP-beads to the mixture with an incubation of 1 hour at 4° C.;

(4) separation of the unbound fraction from beads;

(5) extraction of the RNA, DNase I treatment and cDNA synthesis;

(6) RT-qPCR analysis based on the enrichment (signal-to-noise ratio; i.e. the ratio between 3P-ΔΔct of and mP-ΔΔct; housekeeping gene, 18S).

Our data showed ~2 fold enrichment of luciferase transcript (G) on 3P-beads with respect to the control (mP-beads. FIG. 12b). This result demonstrates that 3P can be used to capture transcripts undergoing translation and this data are consistent with reported RT-qPCR fold changes observed for mRNAs immunoprecipitated with specific antibody against RNA-binding proteins[54,55].

Figure 13:
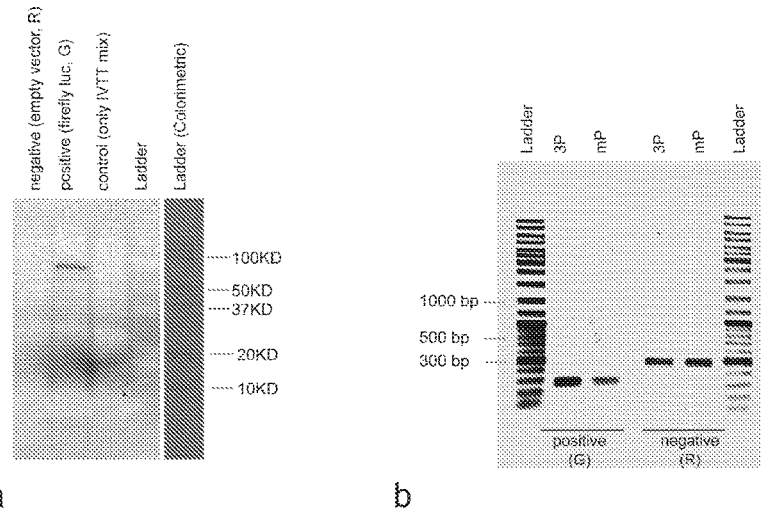
FIG. 13. Proteins and RNAs produced by the in vitro transcription/translation system. (a) Total translation of positive (G, firefly luciferase) and negative (R, empty vector) vectors after 90 min of in vitro transcription/translation (TNT Quick In Vitro transcription translation system, Promega #L2881) coupled with a non-radioactive detection system (Transcendent, Promega #L5080). Proteins were run in SDS-PAGE, after gel transfer to the membrane was visualized in chemiluminescence. (b) PCR products generated from the single stranded cDNA obtained after purification with mP or 3P functionalized beads (see Materials and Methods for a detailed protocol). Gel: TAE agarose 1%. Molecular weights 'a' and fragment lengths 'b' are reported on the ladder's side for clarity.
Figure 14:
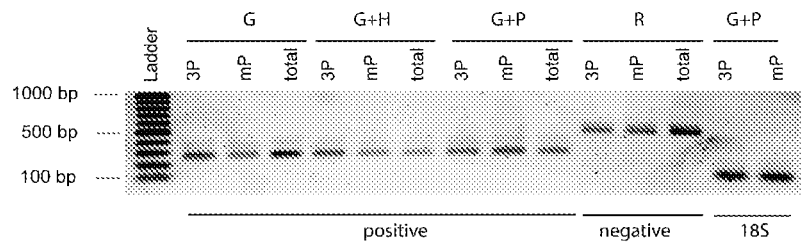
FIG. 14. Agarose gels with PCR products from RT-qPCRs. Amplicons from PCR amplification of positive (G, firefly luciferase), negative (R, empty vector) and 18S rRNAs obtained following the protocol described in FIG. 12a. G, positive control; G+H, positive control incubated with harringtonine (2 µg/mL); G+P, positive control incubated with puromycin (10 µg/mL); R, negative Ladder's fragments lengths are reported on the left. Agarose gel TAE 1%.

To further explore the efficiency of 3P-beads to isolate the translatome we performed the same experiment adding two different drugs to the reaction mixture: harringtonine (called 'G–H') or puromycin (called 'G+P'). The first drug is a potent inhibitor of translation initiation[56], while the second one disassemble ribosomes and is a direct competitor of 3P in solution. As an additional control, we performed the experiment in the presence of a not translating transcript (R, FIG. 12) generated from an empty vector (pGEMEX-1, Promega #P2211) and under the control of the same promoter of the luciferase gene (SP6 promoter). R does not have ribosome binding site and stop codon. We confirmed that G is transcribed while R is not, based on the incorporation of biotinylated lysine (FIG. 13a). We observed the enrichment of 3P-beads RNA with 'G' with respect to 'R' and to the not treated sample, and a higher absolute quantity of RNA on 3P-beads with respect to mP-beads (FIG. 13b and FIG. 14). The RT-qPCR enrichment analysis (signal-to-noise ratio 3P/mP fold changes; i.e. the ratio between 3P-ΔΔct of and mP-ΔΔct; 18S, housekeeping gene; normalized for the total amount of transcripts) demonstrates the absence of significant enrichment, with respect to the not traded sample, of the luciferase transcript for samples (FIG. 12): 'G+H' (Log 2=−0.68±0.81), 'G+P' (Log 2=−0.32±0.35) and 'R' (Log 2=0.00±0.39).

This result confirms that 3P-beads can be selectively enriched in luciferase transcript only when translation takes place. It is worth noting that the signal-to-noise ratio has to be included in the analysis for reliable results.

Figure 15:
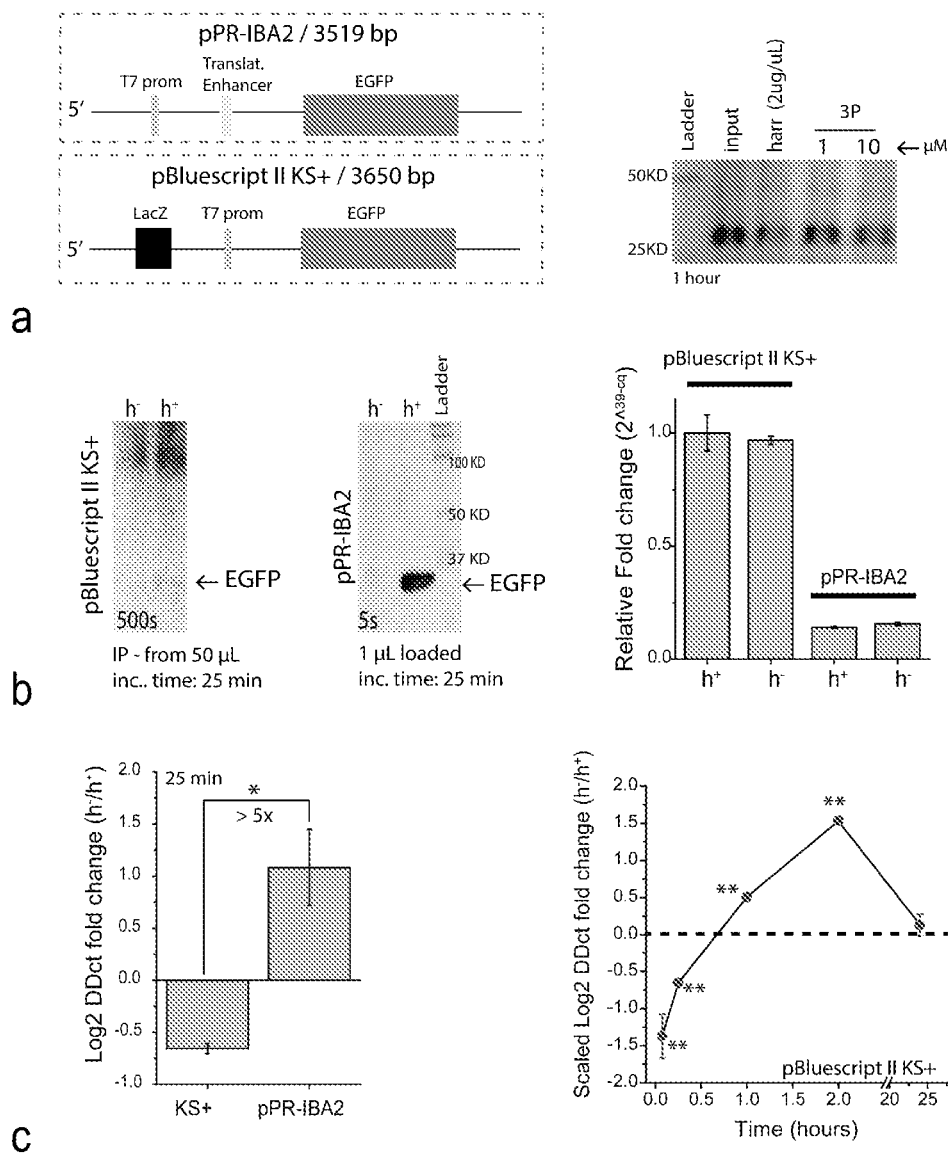
FIG. 15. Isolation of actively translated GFP transcripts after in vitro expression of EGFP protein. (a, left) The two plasmids used for EGFP expression (pBluescript II KS+, Genscript; pPR-IBA2, IBA, #2-1391-000). The scheme shows features upstream the EGFP gene (EGFP, dark gray rectangle; LacZ, β-galactosidase gene, black; Translational enhancer ribosome binding sequence, white; T7 promoters, gray). (a, right) Western Blot reporting the effect of harringtonine and 3P free in solution on protein expression (concentrations as reported in the figure, 1 hour incubation time, at 30° C., 2 µg plasmid, 50 µL IVTT euk-mix). (b, left) Western Blot showing the total immunoprecipitation (IP) of the EGFP expressed in 50 µL of reaction from the pBluescript II KS+ plasmid (2 µg of plasmid in the mix, exposure time; 500 seconds; IP performed with 20 µL Dynabeads Protein G, Invitrogen, #10003D functionalized with 2 µg of anti-GFP antibody, Life tech, #A11122). (center) EGFP expression from the pPR-IBA2 plasmid (300 ng of plasmid in the IVTT euk-mix, exposure time: 5 seconds; 1 µL of reaction mixture loaded on the gel). (right) RT-qPCR analysis of EGFP RNAs in two reaction mixtures: h⁻ and h⁺. The relative abundance is reported as 2^(39-Cq), where 39 are the number of cycles and Cq is the quantification cycle. (c, left) Fold change enrichment of actively translated EGFP RNAs on 3P-beads respect to mP-beads after 25 min of incubation with the IVTT euk-mix (2 µg of plasmid in the 59 µL mix, 30° C.). (c, right) Fold change enrichment of the EGFP RNA captured with 3P-beads at different time points of protein expression (IVTT euk-mix). EGFP from pBluescript II KS+ plasmid; reaction conditions: 2 µg of plasmid in 50 µL mix, 30° C. Beads used: Streptavidin Mag Sepharose™.

In a further experiment, to evaluate the effect of 3P on proteins expressed in vitro with different kinetics, we expressed EGFP by cloning the gene into two different vectors: pBluescript II KS+ vector and pPR-IBA2 vector (FIG. 15a).

After 1 h of incubation, pBluescriptII KS+ expresses a well detectable level of EGFP (FIG. 15a, right). Only barely levels of total EGFP can be detected after 25 min (total protein immunoprecipitation), while the same protein cloned in the pPR-IBA2 plasmid has an estimated 500-fold higher expression (FIG. 15b) with respect to the one cloned into the pBluescript II KS+ vector. After coupled transcription/translation reaction, we monitored the selective enrichment of eGFP RNA on 3P-beads in both not treated and treated with harringtonine (h+, FIGS. 15a and 15b; harringtonine from Santa Cruz, #sc-2040771). For purifying mRNAs associated to polysomes and to reduce the unspecific binding in this case we used agarose magnetic beads (Streptavidin Mag Sepharose™, GE Healthcare, #28-9857-38) instead of polystyrene beads (Dynabeads).

We confirmed the inhibitory effect of both harringtonine and 3P (free in solution) on EGFP expression (FIG. 15a). We observed a difference in protein levels between the two samples that is not due to transcriptional changes. In fact, the total eGFP RNA level is equal in both h+ (drug) and h− (no drug), and it is lower in the sample where the protein is expressed from the pPR-IBA2 vector (FIG. 15b). Therefore, changes in protein level are based on a different efficiency in translation. We observed that the enrichment of the eGFP RNA after 25 min of incubation on 3P-beads (compared to the harringtonine treated sample) is ~5× higher in the sample were the EGFP is highly expressed (FIG. 15c), demonstrating a result coherent with the change in protein expression. Then, we studied the time course of mRNA recruitment on polysomes (8, 25, 60, 120 min and 24 hours of incubation of the IVTT euk-mix with the pBluescriptII KS+ plasmid) isolating the RNA using the 3P-beads (FIG. 15c). While no enrichment has been observed at 8, 25 min and 24 hours, RT-qPCR analysis showed an enrichment of the eGFP RNA after 60 and 120 min. This result demonstrates the efficiency of 3P to capture actively translated RNAs and suggests a temporal resolution of our technique. At 25 min no RNA enrichment was observed due to the high background of transcripts in the mixture (~0.2 µg/µL).

Overall we can conclude that RiboLace (which comprises new molecules, protocols and methods) can be used to selectively enrich samples with transcripts undergoing translation in vitro.

RiboLace Efficiency on Purified Polysomal Fractions

To better investigate RNA translation, we sought to quantify the total rRNAs extracted with 3P-beads respect to the total rRNAs, in each fraction of a polysome profile obtained from a breast cancer cell line.

Figure 16:
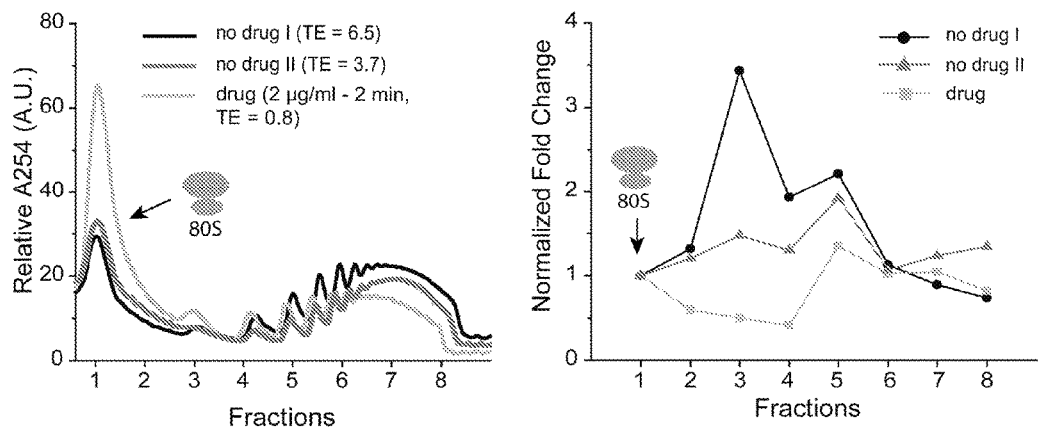
FIG. 16. RiboLace on purified sucrose fractions. (Left) Polysome profiles obtained from not treated cells (no drug I and no drug II, where I and II are two independent biological replicates) or treated with harringtonine (drug) as reported in the legend. TE=global translational efficiency[45]. Sucrose gradient polysomal profiles obtained from lysates of MCF7 cells. (Right) rRNA enrichment calculated as the ratio between rRNAs extracted with 3P-beads over total rRNAs in each fraction, normalized for the 80S (fraction 1). Values have been obtained from a densitometry analysis of both 18S and 28S bands in a 1% TBE Agarose gel. Beads used: Streptavidin Mag Sepharose™.

After sedimentation in a sucrose gradient, using exponentially growing MCF7 cell lysates, we evaluated the enrichment of both total rRNA and 3P-rRNAs (rRNAs extracted from 3P functionalized agarose beads) from each fraction of the profile. We tested two different biological conditions: non-treated cells and cells treated with harringtonine (h+), 2 µg/mL, for 2 min both followed by incubation with cycloheximide (10 µg/mL, 3 min). The advantage of using only biological controls (i.e. absence of mP-beads) resides in a faster, less expensive and easier procedure. The relative abundance, normalised for the 80S fold change, shows an enrichment at the level of light polyribosomes (from fraction 8 to 10), while this effect is lost in heavy polyribosomes (FIG. 16).

The two not-treated samples show differences in the global translational efficiency[45] (TE). This most probably reflects the metabolic state of the cells. In both samples, we observed a consistent enrichment of rRNAs in lighter fractions and a more pronounced effect in the sample with higher TE.

Where active ribosomes are distributed along the profile is currently not known. Some studies have reported that the translational activity per ribosome increases with the number of ribosomes bound per mRNA[57,58], but this finding has not been widely reproduced.

Our data suggests that active ribosomes may concentrate in these lighter fractions.

Activity on Polyribosomes from a Cell Lysate of a Human Cell Line

On the basis of our findings, we speculated that the technique could also work to capture active ribosomes from a more complex cytoplasmic cellular lysate than in vitro translation systems and purified polysomal fractions.

By using a breast cancer cell line we first checked if proteins that are structural components of the ribosome (i.e. RPL26 and RPS6) or if translation initiation factors known to be associated with polyribosomes (i.e. eIF4B and eIF4A1) are indeed enriched in 3P-beads respect to mP-beads. For this reason, we optimised the protocol as follows (FIG. 17):

(1) Beads (200 μg) were functionalized with 3P (3P-beads) and mP (mP-beads);

(2) 3P-beads and mP-beads were directly added to a cell lysate (A260=0.3-1.7 a.u./μL) and the suspension incubated for 1 hour at 4° C.;

(3) Beads were then pulled down by magnet separation and washed two times (without detaching them from the magnet) with 10 mM NaCl, 10 mM $MgCl_2$, 10 mM Hepes, 20 μg/mL cycloheximide (CHX), pH 7 in DEPC water;

(4) Protein and/or RNA were extracted for detection (see Materials and Methods for a detailed protocol).

Figures 18, 19:
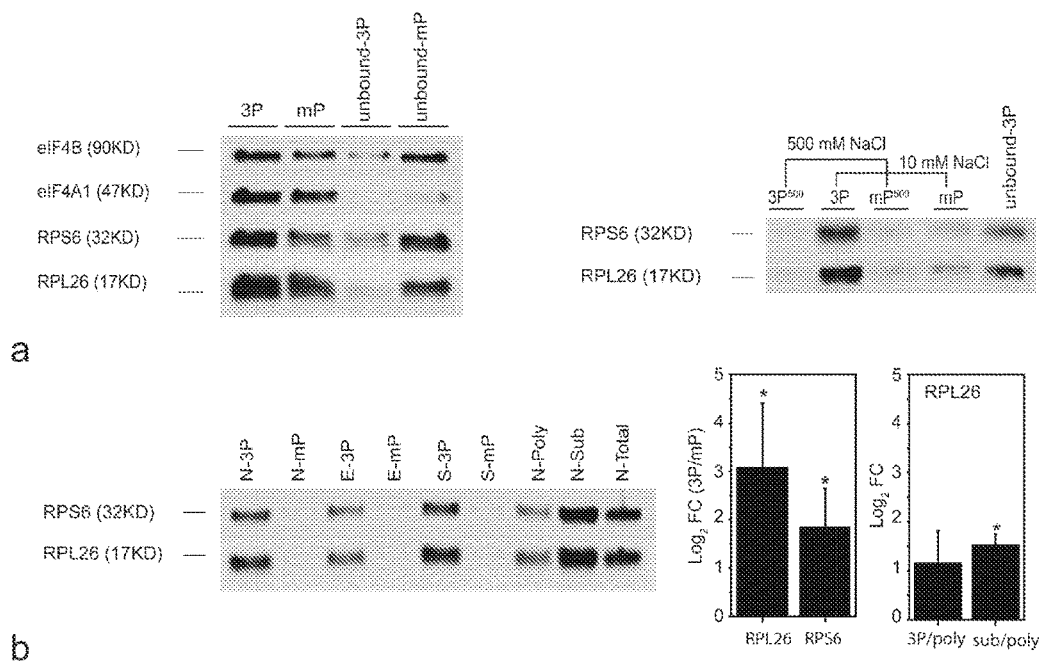
FIG. 18. Protein enrichment on functionalized beads. (a, left) Western blot of ribosomal proteins (RPL26, RPS6) and proteins associated with translation initiation (eIF4B, eIF4A1). The pull down with 3P-beads (3P) and control beads (mP) is reported together with the relative protein content in the unbound fractions (unbound, 1/10 of the total unbound protein content has been loaded in each well). Cell lysate is obtained from MCF7 cell line as described in 'Material and Methods'. (a, right) Effect of salt concentration on the capture of ribosomal proteins. An increase of NaCl concentration form 10 mM to 500 mM hampers the capture of ribosomal proteins by the 3P-beads. Cell lysate from NSC-34 cell line. (b, left) Effect of different stimuli on the capture efficiency. Western blot of RPS6 and RPL26 after pull down with 3P- and mP-beads from non-treated cells (N), cells treated with EGF (1 μg/mL, 4 hours) after 12 hours serum-starvation (E) and cells in serum-starvation for 12 hours (S). The last three lines on the right show the total protein extracted from the total fractions (N-Total), polyribosomal fractions (N-poly) and sub-polyribosomal fractions (N-sub; right panel) after sucrose gradient ultracentrifugation. (b, right) On the left, relative quantifications representing the density fold change ratio (3P/mP, Log 2 scaled). Data are normalized for the total protein content. On the right, the RPL26 fold change ratio (Log 2 scaled) for 3P-beads and total sub-polysomal protein content respect to the polysomal protein content. (*), t-test p-val=0.02 (RPL26); t-test p-val=0.01 (RPS6); t-test p-val=0.01 (sub/poly); n=3. Volume loaded for each sample: 10 μL.
FIG. 19. Separation of proteins associated or not associated to polysomes by 3P-beads or mP-beads. Proteins not associated with polyribosomes as ACTB and GAPDH were not detected after protein extraction from beads.

We observed a significant enrichment of ~8-fold for RPL26 and ~4-fold for RPS6 with respect to the control beads (FIG. 18). Factors involved in unwinding the secondary structures of RNA during translation initiation are also enriched in the 3P-beads sample (FIG. 18a), while proteins that are not involved in ribosome activity (i.e. Actin B and GAPDH) are not present on beads (both 3P- and mP-beads, FIG. 19). We tested two different cell lines, confirming the enrichment on lysates from both breast cancer cell (MCF7, ATCC #HTB-22) and from a motor neuron-like cell (NSC-34, CEDALANE #CLU140, FIG. 18). Interestingly, an increase in ionic strength from 10 mM NaCl to 500 mM NaCl ends up in a loss of purification activity (FIG. 18a). The analysis of cellular lysates from cells in different biological conditions (EGF-treatment and serum-starvation on MCF7) corroborates the result (FIG. 18b). This may be caused by a dissociation of ribosome subunits. Finally, we observed a significant enrichment of both RPL26 and RPS6 on 3P-beads respect to mP-beads (FIG. 18b). But we did not observe a significant difference between the two proteins (FIG. 18b), suggesting that 3P can efficiently capture the 60S subunit (of which RPL26 is a component) bound to the 40S (of which the RPS6 is a component).

Figure 20:
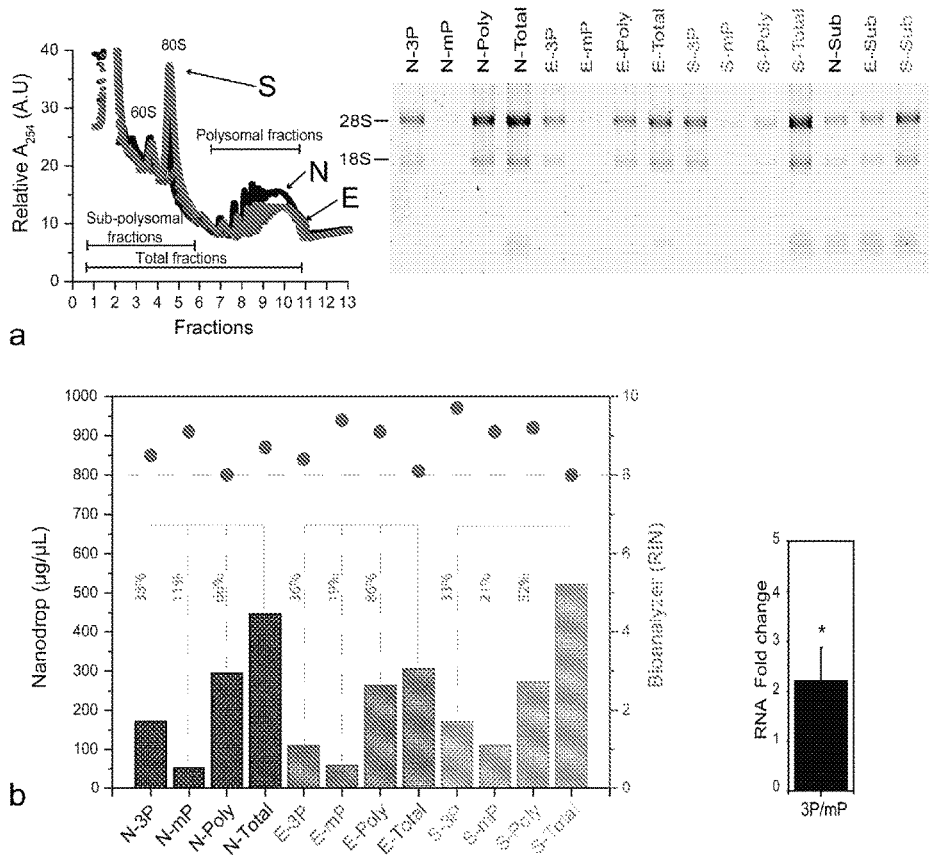
FIG. 20. RNA enrichment on functionalised beads. (a, left) Total RNA from non-treated cells (N), cells treated with EGF (1 μg/mL, 4 hours) after 12 hours serum-starvation (E) and cells in serum-starvation for 12 hours (S), were recovered by sucrose gradient fractionation, acid-phenol extraction and isopropanol precipitation. (a, right) Total RNAs extracted from 3P- and mP-beads, polyribosomal (poly), sub-polyribosomal (sub) fractions and total RNA were run on a MOPS-formaldaide agarose gel (1% agarose). Lanes: (N), RNAs extracted from non-treated cells; (E), EGF treated cells; (S) RNA extracted from serum-starved cells. Bands corresponding to the 28S and 18S rRNAs are indicated. Lysate from MCF7 cells. (b, left) Nanodrop quantification (y-left) and RIN (y-right) of the RNA reported in 'a'. The yield percentage for each sample relative to the total RNA for each condition is reported in light gray. RIN values≥8 (broken gray line) indicate good quality of the RNA samples. (b, right) Relative fold change of total RNA extracted from the 3P-beads respect to the total RNAs extracted with mP-beads (n=6, t-test p-val=0.04, n=3; lysates from MCF7 non-treated cells).

To further characterise the activity of our molecule, we focused our analysis on the two main ribosomal RNAs (rRNA 18S and tRNA 28S). 3P-beads are enriched in both 18S and 28S rRNAs: 3P can capture 2 times more rRNAs with respect to mP (FIG. 20a). This result is in agreement with our afore-described in vitro experiments. Furthermore, the protocol ensures a good quality of the recovered RNAs (Rna Integrity Number, RIN≥8; FIG. 20b). Overall, we conclude that RiboLace is quantitatively efficient in binding polyribosome-associated proteins and RNAs.

Ribolace on Cell Lysates with Only Biological Controls

Figure 17:
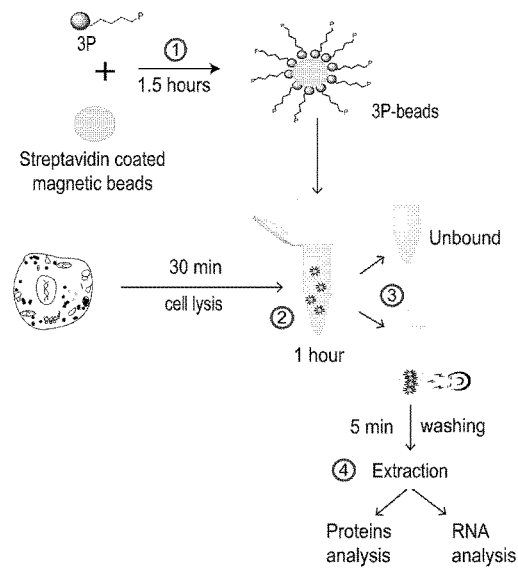
FIG. 17. Optimized protocol to capture ribosomes in active translation from cell lysates. Magnetic beads coated with streptavidin are functionalized with the 3P molecule (step 1). 3P-beads are then added to the crude MCF7 lysate (step 2) (usually 5-20 μL, corresponding to ~0.4-1.5×10$^5$ cells). Proteins and RNA can be recovered after beads pull down, separation of the supernatant and washing (step 3 and 4). Beads are not detached from the magnet during the washing step (see 'Materials and Methods' for the detailed procedure).

To test the if control beads are required, we applied the protocol previously used and described in FIG. 17, but without control beads. We extended our analysis to a cellular lysate from a MCF7 cell line in exponential grow (called, $h^-$/FBS$^+$), under serum starvation (0.5% FBS) for 18 hours (called, FBS$^-$), or treated with harringtonine ($h^+$) for 2 min (2 μg/mL).

Figure 21:
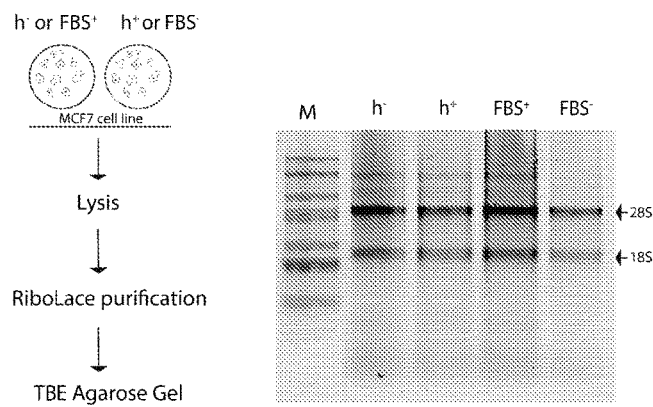
FIG. 21. RNA extracted with RiboLace from cell lysates treated or not treated with harringtonine. (left) MCF7 cell lysates were incubated with 3P functionalized Streptavidin beads (#28-9857-99, GE Lifesciences). The total RNA on 3P-beads was extracted with Trizol and loaded on agarose gel. (right) RNA extracted after RiboLace purification and loaded on a 1% agarose gel stained with SYBR® Gold (#811494, Thermo Scientific). M, 0.5-10 kb RNA ladder, #15623200, Life Technologies; h$^+$, cells treated with harringtonine (2 μg/mL, 2 hours); h$^-$, cells not treated with harringtonine, or alternatively, FBS$^+$ cells in exponential growth; FBS$^-$, cells under serum-starvation (0.5% FBS for 18 hours). TBE Agarose gel.

We observed a ~3-fold enrichment of rRNAs on 3P-beads in FBS$^+$ respect to FBS$^-$. The h+ sample (FIG. 21) shows ~20% more rRNAs respect to the control ($h^-$).

The small differences observed (respect to our results on purified sucrose fractions) are most probably due (i) to the higher chemical complexity of the lysate, (ii) to the average of translational signals detected from the lysate and (iii) to the presence of surfactants in the lysate that can hamper 3P binding, (iv) to the absence of control beads for a better data analysis.

This experiment confirms the activity of 3P to select RNAs only in those samples where translation is not depressed and confirms the preference of using control beads to obtain better results.

NGS Analysis: A Comparison Between the 'Gold Standard' and the RiboLace Technique To gain more insight into the quality and quantity of RNAs captured by RiboLace and to systematically monitor the ability to capture ribosomes involved in active translation (i.e. active polyribosomes) we compared our technology with the standard sucrose gradient fractionation by means of RNA-sequencing (RNA-seq) analysis. We performed the experiment in three different biological conditions (FIG. 22):

(1, N) cells in exponential grow in DMEM with red phenol (Lonza #BE12-614F) supplemented with 10% FBS (Life technologies #10270-098), 2 mM L-glutamine (Life technologies #25030-149), 100 units/ml penicillin and 100 mg/ml of streptomycin (Life Technologies #15140-122);

(2, E), cells under Epithelial Growth Factor stimulation (EGF, 1 μg/μL, RD System #236E4) for 4 hours after 12 hours of serum-starvation (DMEM-red phenol supplemented with 0.5% FBS, 2 mM L-glutamine, 100 units/ml penicillin and 100 mg/ml of streptomycin);

(3, S) cells in serum-starvation for 12 hours.

Figure 22:
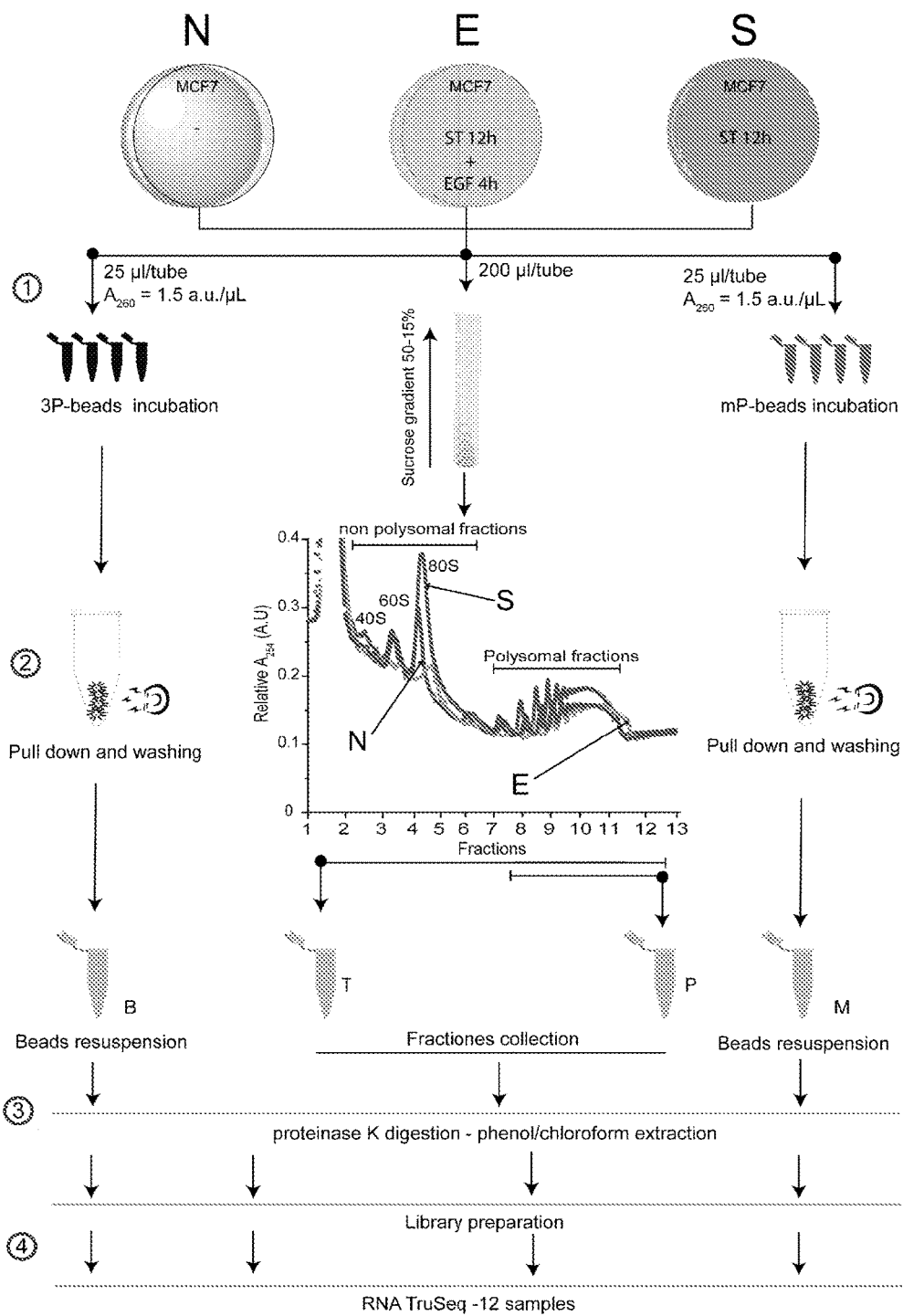
FIG. 22. Protocol used for the RNA-seq analysis. MCF7 cell lysates from each different condition (not treated cells (N); EGF-treated cells (E); serum-starved cells (S) were processed as follow (Step 1-4): (1), the lysate is added to the sucrose gradient or to functionalized beads. (2), Polyribosomes are separated with beads. Polyribosomal fractions and total cytoplasmatic RNA are extracted in parallel. Polyribosomal, P; Total, T. (3), After proteinase K (Life technologies #EO0491) digestion, RNA is extracted from 3P-beads (B) and mP beads (M), and from sucrose gradient fractions (1 mL each) to obtain both polyribosomal and total RNA from the same profile. RNAs is extracted by acid-phenol extraction. (4), Libraries are prepared using the Illumina TruSeq library preparation kit and the sequencing performed with Illumina HiSeq 2000.
Figure 23:
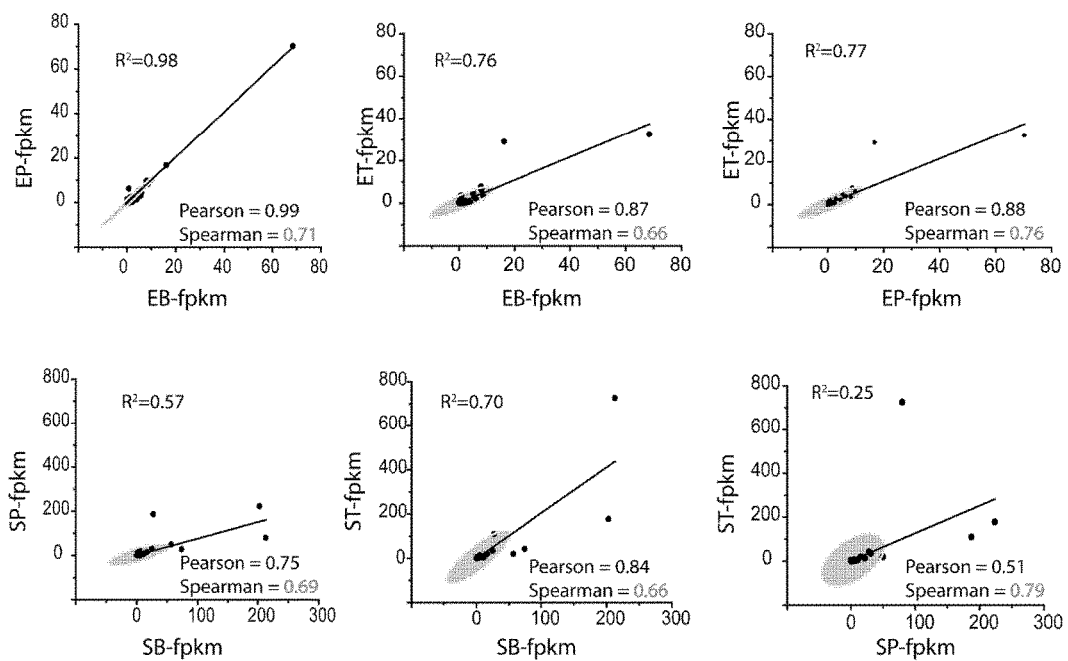
FIG. 23. Correlations of EGF-treated and serum-starved sample. Scatter plot of EGF treated (up) and serum-starved (bottom) reads (FPKM). Only genes with 3P-FPKM higher than mP-FPKM number are included in the analysis. EP, polysomal RNA from EGF-treated cells; ET, total RNA from EGF-treated cells; EB, 3P-beads RNA from EGF-treated cells; SP, polysomal RNA from serum-starved cells; ST, total RNA from serum-starved cells; SB, 3P-beads RNA from serum-starved cells; Pearson and Sperman's correlation (pval<0.05) are reported for each graph. Ellipse represents the 95% confidence level. R$^2$, Adjusted coefficient of determination.
Figure 24:
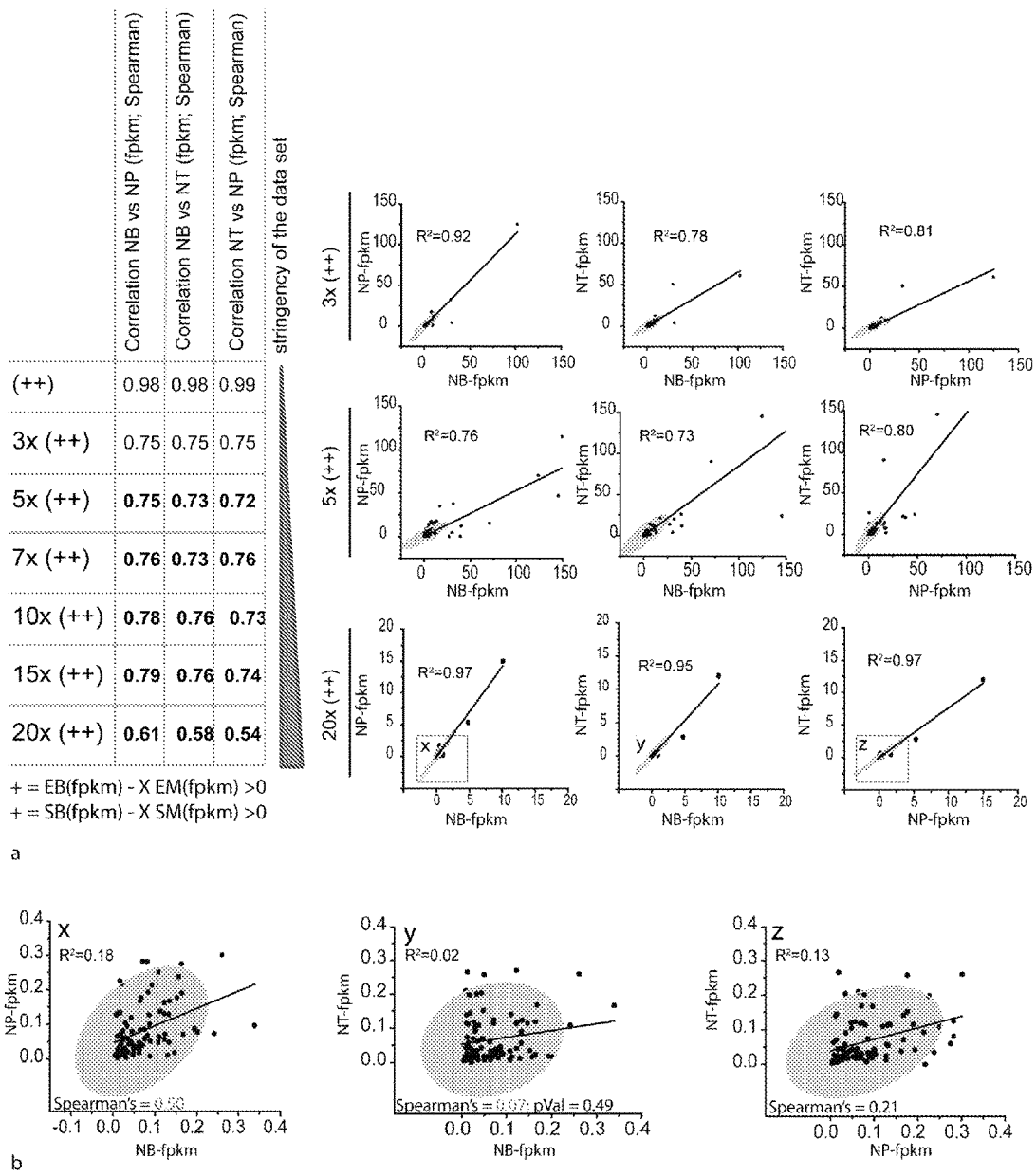
FIG. 24. Correlations of control samples. (a, left). The table reports different Spearman's correlations at increasing stringency (from 1× to 20×, i.e. 20 times more beads-FPKM respect to the control) of the data sets (a, right) Scatter plots for the 3×, 5× and 20× data set respectively. (b) zoom out (x, y, z boxes) on the 20× data set. NP, polysomal RNA from not-treated cells; NT, total RNA from not-treated cells; NB, 3P-beads RNA from not-treated cells; Pearson and Sperman's correlation (pval<0.05 if not specified) are reported for each graph. Ellipse represents the 95% confidence level. Only genes with 3P-FPKM number higher than mP-FPKM number are included in the analysis. R$^2$, Adjusted coefficient of determination.

EGF has an important function in the regulation of cell growth, proliferation, and differentiation by binding to its receptor (EGFR) and its effects have been studied at both transcriptional and post-transcriptional levels[16]. Before lysis, cells were treated with CHX for 5 min (10 μg/mL) to trap elongating ribosomes onto mRNAs. Polyribosomes were then extracted using 3P functionalized beads (called 'B'), mP control beads (called 'M') and with the standard sucrose gradient fractionation method (called 'P'). The total cytoplasmic RNA (called 'T') was also extracted from a collection of all fractions of the profile (FIG. 22). Starting from 1 μg of high-quality RNAs (RIN≤8), results from sequencing of poly-A enriched RNAs (i.e. mRNAs) are obtained using the Illumina HiSeq 2000 platform (see Material and Methods for the detailed protocol). RNA-seq allows quantitative measurement of the expression levels of genes, measured in fragments per kilobase of exon per million mapped reads (FPKM)[59]. To normalize for unspecific binding, i.e. to take into account the impact of the background, we first defined differentially expressed genes (DEGs) upon EGF treatment, and then we analysed the transcripts where the number of 3P-FPKM was higher than the mP-FPKM number. We observed a positive correlation between FPKM of polysomal transcripts isolated from sucrose gradient (EP) and transcripts isolated from 3P-beads (EB) (Spearman's Correlation=0.71). The correlation is lower between total-FPKM (ET) and 3P-FPKM (Spearman's Correlation=0.66 for both EGF-treated and serum-starved cells). The correlation between sucrose gradient polyribosomes-FPKM (EP) and total-FPKM (ET) is 0.76 (FIG. 23). The same pattern is observed for the serum-starvation condition (Spearman's Correlation=0.69 between SB and SP, FIG. 23). In not treated cells the correlations between 3P-FPKM (NB) and both sucrose gradient polyribosome-FPKM (NP) and total-FPKM (NT) was higher (FIG. 24, Spearman's Correlation ~0.98 between SB, ST and SP). Selected genes with 3P-FPKM 20-times higher than mP-FPKM (FIG. 24a) showed a Spearman's correlation of 0.61 between sucrose-gradient polyribosome-FPKM (NP) and 3P-FPKM (NB), 0.58 between total-FPKM (NT) and 3P-FPKM (NB), and 0.54 between sucrose-gradient polyribosome-FPKM (NP) and total-FPKM (NT; FIG. 24). All these information brought to the conclusion that there is a statistically significant relationship between the translatome from 3P-beads and sucrose-gradient polyribosomal mRNAs.

Figure 25:
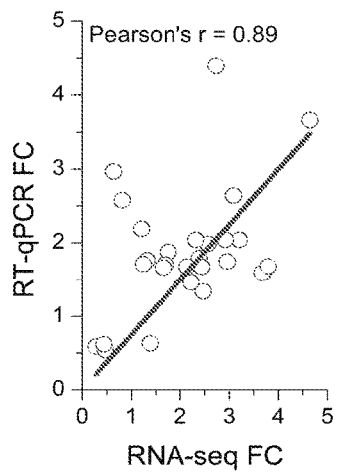
FIG. 25. Concordance of RNA-seq data with RT-qPCR data. Correlation of RNA-seq (x axis) with RT-qPCR data (y axis) using the pearson fold change measure for eight genes (PALLD, PLK3, IL27RA, NCS1, VEGFA, DUSP5, PDCD4, PAPSS2) and four different RNA purifications: 3P, mP, sucrose-gradient and total RNA.
Figure 26:
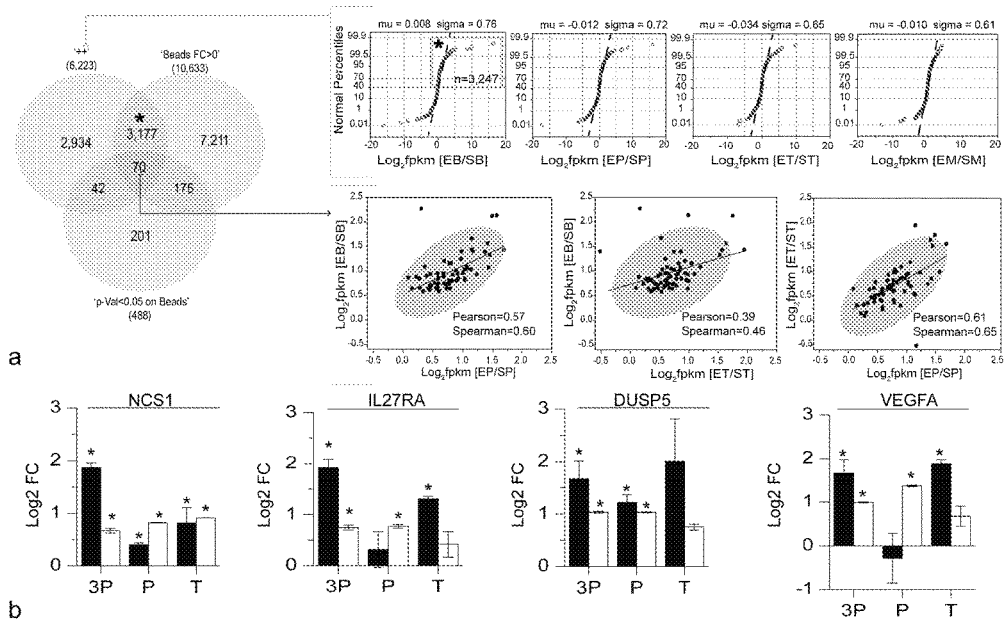
FIG. 26. Analysis and validation of NGS data by RT-qPCR: correlation of DEGs and RT-qPCR. (a—left) Venn diagram (left) with intersection of three data sets: "++" genes with 3P-fpkm>mP-fpkm on both EGF-treated and serum-starved cells; 'Beads FC>0', genes with positive fold change (FC) on 3P-beads; 'pval<0.05', genes with p-value<0.05. The number of genes for each category is reported in brackets. (a—right, up) Probability scatter plots describing the normal distribution of the fold changes for the '++' data-set Log 2 scaled (n=6,223 genes). From left to right: fold changes obtained for 3P-RNA, polyribosomal sucrose-gradient; total RNA and mP-RNA. Normal distribution parameters: mu, mean of the normal distribution; sigma=standard deviation of normal distribution; broken line; theoretical distribution. DEGs with positive fold changes on 3P-beads are 3,247 (light gray box). (a—right, bottom) Common genes (n=70) that emerge from the intersection of the three data-sets are compared. Scatter plots from left to right: EP/SP (polyribosomal sucrose-gradient RNA) compared to EB/SB (PNA from 3P-beads); ET/ST (total RNA) compared to EB/SB; and EP/SP compared to ET/ST. EP, polyribosomal RNA from EGF-treated cells; ET, total RNA from EGF-treated cells; EB, 3P-beads RNA from EGF-treated cells; SP, polyribosomal RNA from serum-starved cells; ST, total RNA from serum-starved cells; SB, 3P-beads from RNA serum-starved cells. Ellipse represents a confidence level of 95%. (b) Histograms representing RNA-seq and RT-qPCR fold changes (FC) for four selected genes (NCS1, IL27RA, DUSP5, VEGFA), out of the eight genes validated (see FIG. 26). Histograms; Black bars, RT-qPCR fold changes; white bars, RNA-seq fold changes; t-test (*)=p-val<0.05.

Eight differentially expressed genes (PALLD, PLK3, IL27RA, NCS1, VEGFA, DUSP5, PDCD4, PAPSS2) were selected for validation by RT-qPCR (FIGS. 25 and 26). We observed a good agreement between RT-qPCR and RNA-seq FC values (Pearson's r=0.89, FIG. 25 and FIG. 26b).

Figure 27:
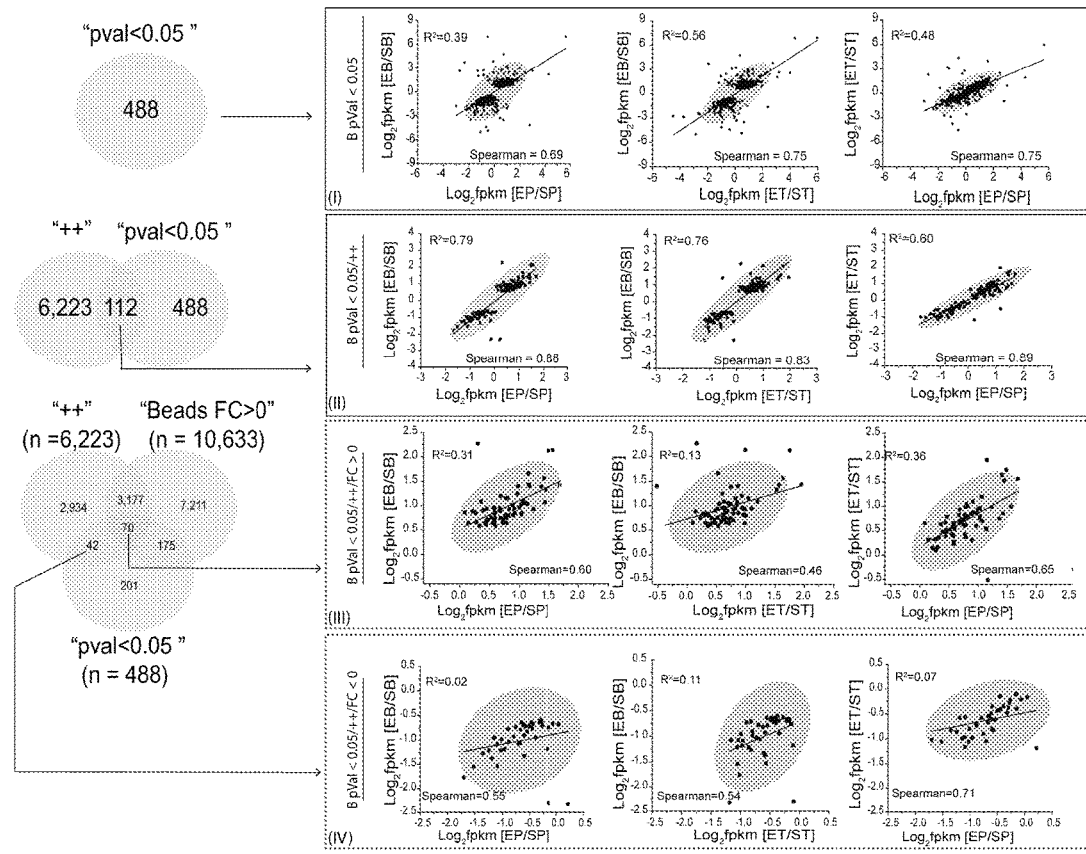
FIG. 27. Correlations of sub-sets of RNA-seq data. On the left of each box a Venn diagram shows the sub-groups of the plotted fold change (Log 2 scaled) data sets. "++" genes with 3P-FPKM>mP-FPKM of EGF-treated and serum-starved cells; 'Beads FC (Log 2)>0', genes with positive fold changes on 3P-beads; 'pval<0.05', genes from 3P-beads with p-value<0.05.

Since up-regulated genes should be preferentially captured and detected (as suggested by our in vitro experiments) we decided to focus our analysis on those up-regulated genes, therefore we selected a subset of DEGs with the following features (FIG. 26): (i) DEGs with positive fold changes of 3P-FPKM (i.e. up-regulated) upon EGF stimulation (EB/SB) (labeled 'Beads FC>0'), (ii) genes with 3P-FPKM pval<0.05 (labeled 'pval<0.05') and (iii) genes with 3P-FPKM higher than mP-FPKM (labeled '++' dataset). First, we observed a normal distribution among '++' DEGs in all samples. From the intersection of the three data sets we identified 70 DEGs with a correlation in fold changes between 3P- and sucrose gradient polyribosomes-significantly higher (Spearman=0.60) than between 3P- and total-fold changes (Spearman=0.46; FIG. 25a). Four of them where validated by RT-qPCR (FIG. 26b). On the contrary, '++' genes with p-val<0.05, but with negative fold changes (n=42) do not show any difference in the correlation values (Spearman=0.55 for EB/SB vs EP/SP; Spearman=0.54 for EB/SB vs ET/ST; FIG. 27). Finally, we noticed that the sub-set of 70 DEGs identified by datasets intersection, showed an enrichment of transcripts that are known to be up-regulated at the transcriptional level after EGF stimulation in MCF7 cells line[60,61]. Among them, we mention PALLD, PLK3, VEGFA, DUSP5 and MAP3K14.

All these results confirm the overall better correlation of 3P-RNAs with polyribosomal-RNAs with respect to total-RNAs.

The Enrichment (Signal-to-Noise Ratio 3P/mP) Follows the Protein Variance

Studies on yeast, mouse and human cell lines reported a low correlation between the total transcriptome and the proteome[62-64], suggesting that the total RNA (transcriptome) is not always reflecting the protein variance. To demonstrate that RNA extracted with 3P-beads is a better solution to predict protein level with respect to standard techniques, we performed a comparative enrichment analysis (Log 2fpkm (EB/EM)–Log 2fpkm(SB/SM)), as we did for the in vitro-cell free assays. The signal-to-noise ratio shows a correlation of 0.20 (for all DEGs with pval<0.05, n=437) between 3P/mP and polysomal DEGs, while the correlation between 3P/mP and total DEGs is 0.15 (Spearman, FIG. 28a and FIG. 29). These data confirmed our results and are comparable to reported correlation between total mRNAs and protein in human cell lines[64,65].

To further understand if RiboLace is more accurate to capture the pool of transcripts undergoing translation, in comparison to both sucrose gradient and total RNAs, we monitored the protein level of four genes (PALLD, PLK3, hb-EGF and CYP27A1) after EGF stimulation. We compared the total protein content with the relative RNA abundance. The total amount of PALLD and PLK3, evaluated by immunoblotting and normalised for three different housekeeping (ACTB, GAPDH and RPL26), does not change upon EGF treatment (n=3, FIG. 28b). The only sample for which the fold change does not significantly show variation on both RT-qPCR and RNA-seq values is the 3P/mP enrichment. For two additional proteins (hb-EGF and CYP27A1) the protein levels increase with coherent fold changes to 3P/mP values (FIG. 30). These results show that our technique is better than the current standard in predicting the cellular protein content, coherently with all the results obtained with the in vitro-cell free system.

Overall, our findings demonstrated that:

(i) the fraction of ribosomes captured by 3P-beads hold transcripts that correlate better with polyribosomal-mRNAs from sucrose-gradient than with total mRNAs, (ii) RiboLace can selectively capture polyribosomes in active translation describing better the protein abundance.

An Additional Application for 3P: Ribosome-Profiling.

High-resolution sequencing of ribosome protected fragments (ribosome-profiling)[18,53,56] is recently the most used technique to study translation at single nucleotide resolution. The treatment of the cell lysate with endoribonucleases convert polyribosomes to monomeric ribosomes, each trapping a short mRNA protected fragment. Ribosome-protected fragments can be purified, sequenced, and mapped back to the genome revealing the overall translation level of each gene, as well as the position of ribosomes along the mRNA. The length distribution of protected mRNA fragments shows an average of 29-29 nt (*S. cerevisiae*) or 30-31 nt (mammalian cells). However, fragments of ~16 nt, ~21 nt and 40-65 nt were also obtained. Although these fragments could be by-products of endoribonuclease digestion, some studies associated them to conformational changes of ribosomes during elongation[56,66,67].

Here, the rationale of our approach is to combine our purification strategy with the ribosome profiling technique. For this reason, we modified our protocol in order to include an endonuclease digestion, a selection of active monomeric ribosomes, and a final visualisation of fragments on a gel for further extraction and NGS analysis. Briefly, we optimised the protocol as follows (see FIG. 31):

(1) A cell lysate (A260=~0.6 a.u./μL, from MCF7 cell line) was freshly prepared after treatment with CHX for 5 min;

(2) Beads (200 μg) were functionalized with 3P (3P-beads) and mP (mP-beads);

(3) The cell lysate was digested with RNase I (0.01-0.02 a.u for unitary sample absorbance at A260) for 45 min at room temperature.

(4) The endonuclease was inhibited by addition of RNase Inhibitor (Life Technologies #AM2696) for 10 min on ice.

(5) 3P-beads were directly added to the digested cell lysate and the suspension incubated for 1 hour at 4° C.;

(6) Beads were pulled down by magnet separation and washed with 10 mM NaCl, 10 mM $MgCl_2$, 10 mM Hepes, 20 µg/mL CHX, pH 7 in DEPC water and proteins digested with proteinase K;

(7) RNA was extracted with Trizol (Sigma, #T9424). If it is required, after this step the RNA can be treated with commercial rRNAs removal kits (e.g. Ribo-Zero rRNA Removal Kit, Illumina, #MRZH11124);

(8) RNA is then run on a 15% PAGE TBE-urea gel for further analysis.

Additionally, 3P-beads were used to isolate ribosomes from MCF7 cell lysates treated ($h^+$) or not treated ($h^-$) with harringtonine (2 min, 2 µg/mL). The RNA was extracted and run on a TBE-urea gel (FIG. 32a) and fragment quantification was then performed (Agilent 2100 bioanalyzer, Small RNA chips, #5067-1548).

Our results showed that 3P-beads can purify more fragments in the condition where translation is not suppressed with respect to the not-treated sample (FIG. 32a). Some of these fragments have lengths in agreement with previously published works[18]. In particular, our fragment enrichment analysis, revealed a 7 fold increase of fragments of ~30 nt in the not treated sample. These fragments can be sequenced (Ribo-seq analysis) to identify the positioning of ribosomes along mRNAs. We also observed more fragments of ~22 nt and ~60 nt in the not-treated sample.

Finally, we performed the same experiment on a mouse brain lysate (FIG. 32b). The experiment has been performed with 30× less material respect to the standard published procedure[18,68]. We clearly observe the presence of ~30 nt fragments on a TBE-urea gel.

Overall these results confirm the possible application of RiboLace for ribosome profiling studies and confirm that the molecule of formula (I) can capture active and native ribosomes (FIG. 33).

Materials and Methods
Primers Fox In Vitro Transcription/Translation, Syber RT-qPCR

```
Primer pairs used in RT-qPCR for the amplification
of the positive control (Luciferase SP6 control
DNA #L4741):
FOR:
                                        SEQ ID No.: 1
CGGCGCCATTCTATCCTCT -

REV:
                                        SEQ ID No.: 2
CCGATAAATAACGCGCCCAA -

Primer pairs used in RT-qPCR for the amplification
of the negative control (pGEMEX-1 vector #P2211):
FOR:
                                        SEQ ID No.: 3
GCAGTACCTAAGCCCTCGAT -

REV:
                                        SEQ ID No.: 4
GGTGGACAGCAAATGGGTAC -

Primer pairs used in RT-qPCR for the amplification
of the 18S rRNA (housekeeping gene):
FOR:
                                        SEQ ID No.: 5
GGATCCATTGGAGGGCAAGT -

REV:
                                        SEQ ID No.: 6
ACGAGCTTTTTAACTGCAGCAA -

Primer pairs used in RT-qPCR for the amplification
of the eGFP gene:
FOR:
                                        SEQ ID No.: 7
AAGCAGCACGACTTCTTCAA -

REV:
                                        SEQ ID No.: 8
ACGTTGTGGCTGTTGTAGTT -
```

TaqMan Assay

For each gene analyzed by TaqMan assay, the gene name, aliases, chromosome location and TaqMan ID is reported in Table 1. All TaqMan probes were from Life Technologies.

TABLE 1

| gene name | aliases | chromosome location | TaqMan probes ID |
|---|---|---|---|
| VEGFA | MVCD1, RP1-261G23.1, VEGF, VPF | Chr.6: 43737946-43754224 | Hs00900055_m1 |
| PLK3 | CNK, FNK, PRK, RP11-269F19.6 | Chr.1: 45266036-45271667 | Hs00177725_m1 |
| DUSP5 | DUSP, HVH3 | Chr.10: 112257625-112271302 | Hs00244839_m1 |
| PALLD | PALLD | Chr.4: 169418217-169849608 | Hs00363100_m1 |
| IL27RA | CRL1, IL-27RA, IL27R, TCCR, UNQ296/ PRO336, WSX1, zcytor1 | Chr.19: 14142262-14164026 | Hs00945029_m1 |
| VEGFA | MVCD1, RP1-261G23.1, VEGF, VPF | Chr.6: 43737946-43754224 | Hs00900055_m1 |
| PDCD4 | H731, RP11-348N5.4 | Chr.10: 112631553-112659764 | Hs00205438 |
| PAPSS2 | ATPSK2, BCYM4, RP11-77F13.2, SK2 | Chr.10: 89419476-89507462 | Hs00989928_m1 |
| 18S | Eukaryotic 18S rRNA | | Hs99999901_s1 |

Chemical Synthesis of the 3P Molecule (Steps 1-4)

1. Synthesis of Biotinyl-N-hydroxysuccinimide (Scheme I; FIG. 34)

D-Biotin (0.49 g, 2.0 mmol, Sigma #B4501) was added to N-hydroxysuccinimide (0.3 g, 2.7 mmol. Pierce #HC102040) into 20 mL DMF (Sigma #227056), heated to 50° C. until most of the material dissolved. A solution of N,N'-Dicyclohexylcarbodiimide (0.45 g, 2.1 mmol, Sigma #D80002) in 5 mL DMF was added dropwise to the aforementioned solution. The resulting solution was stirred overnight at room temperature during which time a white precipitate was formed. The reaction mixture was filtered through celite, and the filtrate was triturated with diethyl ether (Sigma #309966). The white precipitate was vacuum filtered and then washed with diethyl ether to give a white powder. The yield was 0.52 g (~70% final efficiency).

2. Synthesis of Biotin-Jeff Amine Intermediate (Scheme II; FIG. 35)

2,2'-(Ethylenedioxy)bis(ethylamine) (Sigma 385506, henceforth referred to as jeffamine) (0.9 mL, 5.8 mmol) was dissolved in 500 mL acetonitrile (MeCN, Sigma #34888). Biotinyl-N-hydroxysuccinimide (B-NHS, 0.3 g, 0.88 mmol) was dissolved in MeCN (100 mL), this solution was added into a dropping funnel. The B-NHS solution was then added dropwise to the jeffamine solution and stirred overnight, at 0-5° C. under $N_2$. The reaction was filtered, the solid washed with MeCN (2×10 mL) and then with diethyl ether (2×10 mL). Finally pulled dry under $N_2$ to yield a white hygroscopic solid. TLC (10% MeOH/DCM+5 dps $NH_4OH$) does not show apparent starting material after reaction. The solid was dissolved in MeOH (30 mL) at 40° C., dry, loaded on silica and eluted with 10% MeOH/DCM+1% $Et_3N$. Fractions 25-45 were collected and evaporated to a yellow solid/gel. Final yield: 0.257 g (~80% final efficiency). This product is henceforth referred to as BJ1.

Then, Bj1 (0.017 g, 0.043 mmol) was dissolved in dry pyridine (5 mL, Sigma #270970). CDI (Sigma #21860) was dissolved in the same volume of pyridine (0.074 g, 0.45 mmol) and added to the Bj1. The resulting solution was stirred for 2.5 hours at 20° C., when TLC revealed complete reaction (10% MeOH/DCM with 1% $Et_3N$, Sigma #T0886, $R_f$=0.3). The solvent was evaporated, the crude product was reconstituted in a minimum amount of DCM (Sigma #32222) and then ether was added in excess. The precipitate was collected and used in the next step without further purification. This product is henceforth referred to as BJ1'.

3. Synthesis of Puromycin-Jeffamine Intermediate (Scheme III; FIG. 36)

A solution of BOC anhydride (Sigma, #361941) in chloroform (138 mL) was added to a solution of the jeffamine in chloroform (229 mL) maintaining at 0-5° C. The addition was completed in 30 min. The reaction was slowly warmed and stirred at 18-20° C. o/n. The day after the reaction was dissolved in DCM (400 mL) and washed with brine, dried ($MgSO_4$) and evaporated at 40° C. to a clear oil (~93% final efficiency)

Puromycin (0.28 g, 0.613 mmol, Sigma #P8833) was dissolved in pyridine (1 mL) and CDI (dissolved in DCM) was added to the solution (0.103 g, 0.635 mmol).

This solution was added dropwise to a solution of BOC protected jeffamine (jeffamine 0.18 mL, 1.2 mmol) in DCM (250 mL), the reaction solution was stirred overnight at 0-5° C. TLC (10% MeOH/DCM) shows a major product ($R_f$=0.5) as well as little starting material.

The product was partitioned between DCM (250 mL) and water (100 mL), washed with water (2×100 mL) and evaporated at 40° C. to yield sticky oil. The product was triturated in ethyl acetate (EtOAc, 40 mL) at 40° C. for 3 hours to give a gel suspension. The suspension was cooled 35 to 0-5° C., filtered, washed with EtOAc, dried in vacuum at 40° C. to yield a white solid.

Alternatively, the separation can be performed through silica column (10% MeOH in DCM, 1% $Et_3N$). This product is henceforth referred to as PJ1.

Trifluoroacetic acid (TFA, Sigma #302031) was added dropwise to a stirred suspension of PJ1 in DCM (40 mL) at 25° C. After 2 hours, the solution was cooled at 15-17° C. and stirred overnight. The day after the solution was diluted with chloroform (300 mL) and evaporated at 40° C. in vacuum. This was repeated 3 times to give yellow oil. This product is henceforth referred to as PJ1'.

4. Final Synthesis of 3P (Scheme IV; FIG. 37)

BJ1' (0.140 mmol) and PJ1' (0.084 g, 0.133 mmol) were dissolved in 6 mL pyridine and stirred overnight at 55° C. under nitrogen (N2). After that: (i) the solvent was evaporated at 60° under vacuum; (ii) residual pyridine was azeotroped with EtOAc (2×25 mL); (iii) oily material partitioned between EtOAc (3×25 mL) and water (50 mL); (iv) water washed with DCM (2×25 mL). The aqueous phase was then extracted with 1-Butanol (25 ml).

1-Butanol was evaporated at 40° C. in vacuum to obtain an oil (TLC, 10% MeOH/DCM, shows a major product with $R_f$=0.5 under UV light). This final oily product was purified by silica column chromatography and fractions collected (dry loaded in MeOH and eluted in 0.5% NH4OH/10% MeOH/DCM) The desired product is present in fractions 25-50, yielding 0.006 g yellow wax after evaporation. The product was finally purified by preparative HPLC (mobile phase 98% water:2% acetonitrile for 5 min, then to 100% acetonitrile in 35 min at a flow rate of 1 mL/min, UV detector at λ 280 nm). This product is henceforth referred to as 3P.

NMR and LCMS Data of Product 3P $^1$H NMR (400 MHz, DMSO-$d_6$) δ=8.43 (s, 1H, Pur.), 8.23 (s, 1H, Pur.), 8.085 (d, J=7.7, 1H), 7.836 (t, J=5.6, 1H), 7.11 (d, J=8.6, 2H, Pur.), 6.83 (d, J=8.6, 2H, Pur.), 6.414 (s, 1H), 6.352 (s, 1H), 6.167 (m, 2H), 5.973 (s, 4H), 5.163 (s, 1H), 4.433 (m, 3H), 4.297 (m, 1H), 4.119 (m, 1H), 3.909 (dt, J=6.9, 3.8, 1H), 3.649 (m, 1H), 3.491 (s, 11H), 3.356 (m, 7H), 3.118 (s, 9H), 2.820 (m, 2H), 2.687 (m, 1H), 2.060 (s, 2H), 1.484 (d, J=8.1, 3H), 1.297 (m, 2H).

$^{13}$C NMR (100 MHz, DMSO) δ 172.59, 163.04, 158.17, 154.72, 152.27, 150.07, 138.27, 130.03, 120.07, 89.79, 78.06, 70.23, 69.39, 61.54, 59.70, 55.91, 40.31, 39.72, 38.97, 28.90, 25.84.

Purity (>90%) established by HPLC-MS. Stationary phase RP18 (Phenomenex Kinetex #00G-4601-E0 C18 5 μm 250×4.6 mm); mobile phase 98% water: 2% acetonitrile for 5 min, then to 100% acetonitrile in 35 min, UV detector at λ 280 nm. Compound 3P shows a retention time of 17.5 min. MS with positive ion-mode ESI detection and Ion Trap mass analyzer gives a full scan mass spectrum of this peak in agreement with the reported structure. In particular [M+H]$^+$ at m/z 1046.5 consistent with its molecular formula $C_{47}H_{72}N_{11}O_{14}S^+$.

Beads Functionalization

Dynabeads® MyOne™ Streptavidin C1 (10 mg/mL, Life Technology #65001) were placed in a 1.5 mL eppendorf tube fixed on a magnetic stand for 1 min to remove the supernatant and washed for 3 min using 30 μL of 0.05 M NaCl, 0.1 M NaOH, in DEPC-treated water. This solution was separated from the magnetic beads by placing the tube on the magnet for 1 min. Beads were then washed with a solution of 0.1 M NaCl in DEPC-treated water for 2 times (3 min each, 1 min on the magnet). Finally, beads were immersed in a Binding Buffer (2 M NaCl, 1 mM EDTA, 10 mM Tris-HCl, pH 7.5 in DEPC water) for 3 min (1 min magnet separation).

3P in Binding Buffer (1 mM, 50 μL) was then added to the beads followed by and incubation for 1 hour at 1000 rpm at room temperature (RT) in a thermomixer. Beads where then end-capped with mP (1 mM) for 30 min at 1000 rpm at RT. Lastly, beads were washed 3 times (3 min magnet separation) with 200 μL of W-buffer (10 mM NaCl, 10 mM $MgCl_2$, 20 μg/ml cycloheximide, 10 mM Hepes, pH 7 in DEPC water); the tube was then placed on the magnet for 3 min, the supernatant discarded and the "pellet" of functionalized beads used to fish out ribosomes in active translation. In the negative control, beads were functionalized only with mP using the same conditions as previously described (1 mM in 50 μL, 90 min, at 1000 rpm, at RT).

Depletion of 3 Pa with Streptavidin Coated Heads.

Different quantity of magnetic beads are separated from their suspension solution using a magnet. 50 µL of a solution composed of 2 M NaCl, 1 mM 3P, 1 mM EDTA, 10 mM Tris-HCl, pH 7.5 in DEPC water, is added to the 'dry' beads, and the suspension incubated for 5 min at room temperature. After pull down on a magnetic rack, the absorbance of the supernatant was measured at 272 nm.

In Vitro-Cell Free Selection of Translated and/or Transcribed Sequences

In vitro translation of the full-length Luciferase (SP6 Control DNA, Promega #L474A) and the transcription of the negative control sequence (pGEMEX-1 vector, Promega #P22211) as positive and negative control respectively, were obtained using the TnT SP6 Quick Coupled Transcription/Translation System (Promega, #L2881) according with the manufacturer's instruction. Briefly, 0.25 µg plasmids were independently added to 50 µL of IVTT euk-mix reaction, composed of 40 µL TNT quick master mix, 1 µL methionine in DEPC water. After 40 min of incubation at 1000 rpm at 34° C., reactions were incubated for 3 min with cycloheximide (10 µg/ml), then diluted with 400 µL of W-buffer (10 mM NaCl, 10 mM $MgCl_2$, 20 µg/ml cycloheximide, 10 mM Hepes, pH 7 in DEPC water), to a total volume of 450 µL. The solution was dividend in to 3 vials, each of them with 150 µL of reaction. The first, was used for the extraction of the total RNA (Trizol), the second was added to 3P-beads and the third to mP-beads.

In parallel, beads functionalization was performed as described previously ('Beads functionalization' paragraph), starting from 15 µL of beads' The IVTT euk-mix solution was added to the pellet of functionalized beads and the suspension incubated for 1 h in orbital rotation at 2 rpm (StarLab Rotator Rixer) at 10° C. The tube was then kept on ice on a magnetic stand for 5 min to pellet the beads-bounded-ribosomes. The supernatant was separated, an aliquote kept as control (unbound fraction) and beads washed two times with 500 µL of W-buffer. Finally, beads were resuspend in 100 µL of 100 mM NaCl, 10 mM $MgCl_2$, Trizma HCL, pH 7.5 in DEPC water. Total RNA was extracted from the beads-bounded-ribosomes by Tizol and isopropanol precipitation. Total RNA was resuspended in 30 µL of RNase-free water. From this solution, 600 ng of RNA was treated with 2 µL (1 U/µL) of DNAse I (Thermo Scientific, L.T. #EN0521), in a final volume of 10 µL. The digested sample was used for cDNA synthesis (RevertAid RT Reverse Transcription Kit, Thermo Scientific, L.T. #K1622) according with the manufacturer's instruction The luciferase translation efficiency was monitored by means of luminescence signal using the Bright-Glo™ Luciferase Assay System (Promega, E2610) and the Infinite 200 PRO reader (Tecan), according to the manufacturer's instruction. In parallel, the total pool of synthesized proteins were labeled with ε-labeled biotinylated lysine-tRNA complex using Transcend™ Non-Radioactive Translation Detection Systems and the effective translation verified by SDS-PAGE according to the manufacturer's instructions (Promega #L5080).

The in vitro translation of the full-length EGFP cloned into the pBluescript II KS+ and pPR-IBA2 plasmids were performed in the same fashion as the luciferase gene, but adding 2 µg and 0.3 µg respectively of DNAs to the IVTT euk-mix.

MOPS-Formaldaide Gel.

An equal volume of RNA sample (2.5 µL) were brought to 20 µL adding 2 µL of 10×MOPS buffer (200 mM MOPS, 50 mM sodium Acetate, 10 mM EDTA, pH 7 with NaOH), 2 µL of formaldehyde, 9 µL of deionized formamide and 3.5 µL of RNAse-free water. Samples were heated for 10 min at 70° C. and chilled on ice before loading on MOPS-formaldaide agarose gel (1% agarose, IBI Scientific #10D2002).

Cell Culture and Treatments

Breast cancer cell line MCF7 (ATCC #ATCC® HTB-22™) and the hybrid neuroblastoma-spinal cord (NSC34—CEDARLANE #CLU140) cell line were seeded on adherent plates and maintained at 37° C., 1-5% $CO_2$ in DMEM with red phenol supplemented with 10% Fetal Bovine Serum (FBS), 2 mM L-glutamine, 100 units/ml penicillin and 100 mg/ml of streptomycin. Cells were grown until 80% of confluence before lysis. For EGF treatment, after seeding MCF7 cells were maintained in culture until 80% of confluence before replacing the media with DMEM-red phenol supplemented with 0.5% FBS, 2 mM L-glutamine, 100 units/ml penicillin and 100 mg/ml of streptomycin (starvation condition). Cells were kept in starvation for 12 hours at 37° C., 1-5% $CO_2$ before adding EGF (1 µg/µL) for 4 hours.

Isolation of Active Ribosomes from a Cell Lysate with Functionalized Beads

MCF7 cells were seeded at $1.5 \times 10^6$ cells/dish and let them to grow until 80% of confluence. Cells were then treated with 10 µg/mL of cycloheximide for 5 min at 37° C. before lysis in order to inhibit translation elongation. Cells were then washed at 4° C. with PBS complemented with cycloheximide 10 µg/ml and scraped on the plate with 300 µl of lysis buffer (10 mM NaCl, 10 mM $MgCl_2$, 10 mM Tris-HCl, pH 7.5, 1% Triton X-100, 1% sodium deoxycholate, 0.2 U/ml DNAseI, RNase inhibitor, 1 mM dithiothreitol and 10 µg/ml cycloheximide) for each dish. Nuclei and cellular debris were removed by centrifugation for 5 min at 12,000 g at 4° C. (the lysate could be aliquated and stored at −80° C. for not more than a month avoiding more than one freeze and thaw). The absorbance at 260 nm was measured by Nanodrop ND-1000 UV-VIS Spectrophotometer and the lysate diluted to 0.3-1.7 a.u. $A_{260}$/µL with W-buffer (10 mM NaCl, 10 mM $MgCl_2$, 20 µg/ml cycloheximide, 10 mM Hepes, pH 7 in DEPC water). The solution obtained was added directly to the functionalized beads and the suspension incubated on a wheel for 1 hour in orbital rotation at 2 rpm (StarLab Rotator) at 4° C. The tube was then kept on ice on a magnetic stand for 5 min to pellet the beads-bounded-ribosomes. The supernatant was discarded (unbound fraction) and beads washed two times with 500 µL of W-buffer. Finally, beads were resuspended in 50 µL of 100 mM NaCl, 10 mM $MgCl_2$, 30 mM Trizma HCL, pH 7.5 in DEPC water (Resuspension Buffer).

RNA Extraction

Total RNA was extracted from 25 µL of resuspended beads-bounded-ribosomes by adding TRIZOL reagent (Sigma #T94424) according to the manufacturer's protocol. After isopropanol precipitation the pellet was resuspended in 30 µL of RNase free water, quantified by Nanodrop ND-1000 UV-VIS Spectrophotometer and then stored at −80° C.

For RNA-seq experiments the RNA was extracted with standard phenol:chloroform (Sigma #P1944) extraction. For polyribosomal and total RNA extraction, the corresponding fractions were collected and treated with 200 µg/mL proteinase K (Life technologies #EO0491), 1% SDS in DEPC water and RNAse Inhibitor (0.4 a.u./µL) for 1.5 h at 37° C. After phenol:chloroform extraction and isopropanol precipitation, beads-derived, polyribosomal and subpolyribosomal RNA samples were quantified by Nanodrop ND-1000 UV-VIS Spectrophotometer, aliquoted and stored at −80° C.

RNA quality was confirmed with Agilent 2100 Bioanalyzer with RNA 6000 picokit (Agilent #5067-1513) following the manufacture's guidelines.

Western Blot Analysis

According with the type of experiment cell lysates were (i) prepared in polyribosomal lysis buffer (10 mM NaCl, 10 mM $MgCl_2$, 10 mM Tris-HCl, pH 7.5, 1% Triton X-100, 1% sodium deoxycholate, 0.2 U/ml DNAseI, RNase inhibitor, 1 mM dithiothreitol and 10 µg/ml cycloheximide) and processed with functionalized beads or (iii) prepared by radioimmunoprecipitation assay (RIPA) buffer (150 mM NaCl, 0.1% SDS, 0.5% sodium deoxycholate, 1% Triton X 100, 50 mM Tris, pH 7.5 added of pepstatin A, Sigma, #P5818; protease, Sigma, #P8340 and phosphatase inhibitors, Sigma, #P0044; according to the manufacture's protocol). Proteins were quantified by Bradford (Sigma #B6916), separated by SDS-polyacrylamide gel electrophoresis and transferred onto PVDF membranes. Briefly, 5 µL of 6× Leammli loading buffer (0.6 M dithiothreitol, 12% SDS, 60% glycerol, 0.06% bromophenol blue, 0.375 M Tris pH 6.8 with NaOH,) was added to 5 µg of total proteins or to 25 µL of resuspended beads. Samples were heated at 95° C. for 5 min and after a brief centrifugation run in a SDS-PAGE in 25 mM Tris, 192 mM glycine (Biorad, #4569033). Blotting was performed on PVDF membranes (IMMOBILON-P, Millipore #IPVH20200) in 25 mM Tris, 192 mM glycine, 20% v/v methanol, pH 8.3 at constant 280 mA for 2.5 hours. The membranes were blocked in 5% BSA (Sigma #05470) in TBS-Tween (0.1% Tween) for 1 hour, incubated in primary antibody o.n. at 4° C., then washed in TBS-Tween (0.1%, TEST) three times, 10 min each. After incubation with secondary antibodies conjugated to horseradish peroxidase, blots were washed three times in TBS-Tween (5 min each) and processed by ECL Plus detection kit as instructed by the supplier (GE Healthcare, Amersham ECL Prime #RPN2232).

Primary antibody recognizing SPS6 (#2217) was from Cell Signaling (used at 1:1,000 dilution), primary antibodies recognizing RPL26 (#ab59567), eIF4B (ab68474), eIF4A1 (ab31217), hb-EGF (#ab185555), CYP27A1 were from Abcam (used at 1:50 dilution), antibodies recognizing PLK3 (#PA5-15290) and PALLD (#MA5-1641) were from Thermo Scientific (used at 1:1,000 dilution), primary antibody recognizing EGFP (used at 1:1,000 dilution) was from Roche (#13537400). HRP-conjugated secondary antibodies were from Santa Cruz biotechnology (used at 1:10,000 dilution, #sc-2004, #sc-2005), while Streptavidin-HRP (Trascendent kit, #L5080, used at 1:1,000 dilution) was from Promega. The chemiluminescence was acquired by Chem-Doc-It (Bio-Rad) and analyzed with ImageJ software (v 1.45s). All experiments were run in biological triplicates. Methanol/chloroform protein extraction and precipitation before western blot does not improve the accuracy of the result. Precision Plus Protein Standard Kaleidoscope standard (Biorad #161-0375) was used as ladder protein marker.

The EGFP immunoprecipitation was performed with 20 µL of Dynabeads Protein G (Life technologies, #100030) functionalized with anti-EGFP antibody (used at 1:100 dilution, #A11122) and incubated with 50 µL of IVTT-euk mix diluted to 250 µL in TBS buffer (pH 7.5) on an end-over-end rotator for 1-2 hours at room temperature.

Polyoma Profiling

MCF7 cells were seeded at $1.5 \times 10^6$ cells/dish. After treatment (EGF for 4 hours) cells were incubated for 5 minutes with cycloheximide 10 µg/ml at 37° C. to trap the ribosomes on the mRNAs. Cells were washed with PBS complemented with cycloheximide (10 µg/ml) and scraped directly on the plate with 300 µL of lysis buffer (10 mM NaCl, 10 mM $MgCl_2$, 10 mM Tris-HCl, pH 7.5, 1% Triton X-100, 1% sodium deoxycholate, 0.2 U/ml, DNAse I, RNase inhibitor, 1 mM dithiothreitol and 10 µg/ml cycloheximide. Nuclei and cellular debris were removed by centrifugation for 5 min at 12,000 g at 4° C. The supernatant was directly transferred onto a 15-50% linear sucrose gradient containing 100 mM NaCl, 10 mM $MgCl_2$, 30 mM Tris-HCl, pH 7.5 and centrifuged in a Sorvall uitracentrifuge on a swinging rotor for 100 min at 180,000 g at 4° C. The fraction corresponding to the 40S, 60S and 80S peaks and those corresponding to polysomes were collected monitoring the absorbance at 254 nm. Each fraction was flash frozen in liquid nitrogen and stored at −80° C. for RNA or protein extraction.

RNA-Seq

RNA was extracted (from beads and sucrose gradient fractions) by acidic-phenol chloroform separation (Sigma). The quality of the RNA samples was assessed using Agilent Bioanalyzer 2100 and Nanodrop ND-1000 Spectrophotometer (Thermo Scientific). Whole transcriptome library preparation was performed starting from 1 µg of total RNA with RIN≥8. Following enrichment of poly-A containing mRNA molecules using poly-dT oligo-attached magnetic beads, all recovered RNA was processed using the Illumina TruSeq RNA Sample Preparation Kit (Illumina #FC-122-1001 #FC-122-1002) and the protocol v2 Rev. C. Completed libraries were evaluated by DNA quantification and Bioanalyzer analysis (mean fragment length=274 bp), and then submitted for sequencing. RNA-seq was constructed with barcodes to allow multiplexing of 12 samples per lane. Sequencing was carried out on Illumina HiSeq 2000 using the protocol HCS 1.5.15.1 in single reads.

NGS Data Analysis

Samples were sequenced with Illumina HiSeq 2000. Raw sequencing reads (100 nt in length) were mapped to human genome and transcriptome (version GRCh37) with TopHat (available on the web at ccb.jhu.edu/software/tophat/index-.shtml) using default parameters.

Cuffdiff in the Cufflinks package (available on the web at cole-trapnell-lab.github.io/cufflinks/) was used to calculate FPKM values from aligned reads, based on Ensembl gene annotation (Ensembl release 74) and to perform tests on differential expression.

DEGs Validation

RT was performed using random hexamers, single strand reverse transcriptase (RevertAid RT Reverse Transcription Kit, Life Technologies #K1622) and real-time quantitative PCR (qPCRs) was performed using TaqMan gene-specific primers. TaqMan qPCRs were performed in a 96-well plate in a final volume of 20 µL with 10 µL of 2× TaqMan Universal Master Mix II (Life Technology #44400387), 1 µL 20× TaqMan Assay, 1 µl cDNA (1:4 dilution) and RNase-free water. Experiments were run in triplicate. Error bars represent ±s.d. calculated from triplicate experiments.

RT-qPCR on RNAs Extracted from the In Vitro-Cell Free System.

Trizol (Sigma) was used to extract total RNA from functionalized beads and from the total IVTT euk-mix reaction. For each sample, 600 ng of RNA was digested with DNAse I. 60 ng of digested RNA sample were used for single strand cDNA synthesis using RevertAid RT Reverse Transcription Kit according to manufacturer's instruction. RT was performed using random hexamers. RT-qPCR for the quantification of transcript abundance was designed using KAPA SYBT FAST qPCR kit (KAPA Biosystem #KK4651) according to the manufacturer's instructions.

Briefly, reactions were carried out in a final volume of 20 µL, using 1 µL cDNA and the follow cycling condition: 3 min-95° C. activation; 2 sec-95° C. denaturation, 20 sec-57° C. annealing and extension; 25 cycles; 65° C. to 95° C. melting ramp. Data were processed with Bio-Rad CFX-Manager 1.6 software. Relative quantification of target genes was determined calculating the delta cross-threshold (ΔCt) respect to the 18S housekeeping gene and the relative ΔΔCt calculated respect to the total RNA sample, according to the Pfaffl method.

The normalized fold change ratio reported in FIG. 15*c* was determined as the ratio between the ΔΔCt of treated and not treated sample. The delta cross-threshold (ΔCt) was determined respect to the total RNA and the relative ΔΔCt calculated respect to the control (mP-beads ΔCt).

Preparation of the Mouse Brain Lysates

Mouse brain lysate were prepared as described previously in Lunelli L., et al. (2016)[68].

Other Chemical Modifications on the General Formula (I).

In preferred embodiments, 'A' can be an alkyne residue, an azide residue or a biotin residue. The chemistry to couple 'A' with 'L' in the general formula (I) is based on the chemical reaction between the N-hydroxysuccinimidyl ester and a primary amino group of a jeffamine unit, as previously described for the biotin-NHS coupling to the jeffamine. We used the same chemistry to couple the azide and alkyne chemical groups.

Synthesis of the Alkyne-3P Molecule, Called 3PP (Scheme V-Va; FIGS. 33 and 39, Respectively)

The molecules bearing the alkyne residue are selected from commercially available precursors (e.g. alkyne-N-hydroxysuccinimidyl ester, #764221, Sigma; Alkyne-PEG5-N-hydroxysuccinimidyl ester, #764191, Sigma). Jeffamine (7 mmol) was dissolved in 500 mL acetonitrile (MeCN, Sigma #34888). 3 mmol of alkyne-N-hydroxysuccinimidyl ester (alkyne-NHS) was dissolved in DMF (10 mL). This solution was added into a dropping funnel. The alkyne-NHS solution was then added dropwise to the jeffamine solution and stirred overnight, at 0-5° C. under N2. After evaporation the product was resuspended in MeCN and purified by preparative HPLC. The synthesis of the full length molecule was effected by adding this compound to the jeffamine-linked puromycin that has been reacted with CDI. The later compound is prepared in step 3 of the paragraph 'chemical synthesis of the 3P molecule' (material and methods). The latter procedure contains the purification procedure for this material as well.

An additional synthetic route of 3PP is described in Scheme Va (FIG. 39).

Synthesis of 1 (Scheme a; FIG. 40).

2-[2-(2-aminoethoxy)ethoxy]ethanamine (10 molar equivalents in 440 mL of chloroform) was treated with Boc anhydride in Chloroform solution keeping the temperature at 4° C.; after 30 min it was slowly warmed and stirred at 15-18° C. The organic solution was washed with sat. bicarbonate and after with sat. brine, and finally dried on MgSO$_4$. The evaporation in vacuo (iv) at 40° C. yields the desired mono-Boc protected amine (1, 6.86 g, 80.4%) as a clear oil. $^1$H-NMR spectrum in CDCl$_3$ is in accordance with the structure of compound 1.

Synthesis of 2 (Scheme B; FIG. 41)

The amine (1) (2 g, MeCN solution) was coupled to 1 molar equivalent of hept-6-ynoic acid using EDCI.HCl by stirring over weekend at 18° C. The raw material was in vacuo evaporated at 40° C., dissolved in EtOAc, washed in sequence with water, HCl 0.5 mM, water and sat. NaHCO$_3$. The organic part was dried on MgSO$_4$ to yield the desired amide (2, 2.38 g, 82.9%) as a clear colorless oil. $^1$H-NMR spectrum in CDCl$_3$ is in accordance with the structure of compound 2.

Synthesis of 3 (Scheme C; FIG. 42)

To a stirred solution at 25° C. of Boc amine (2) (2.38 g in 48 mL of dichloromethane) was added dropwise pure trifluoroacetic acid (10 molar equivalents, TFA) and kept for 42 h; the temperature was raised to 45° C. and kept until complete disappearance of 2. After standard work-up the amine TFA salt (3, 100%) was obtained as a clear colourless oil. The final mass exceeded 100% yield. $^1$H-NMR spectrum in CDCl$_3$ is in accordance with the structure of compound 3.

Synthesis of 4 (Scheme D; FIG. 43)

0.837 g of CDI in pyridine (21 mL) were added dropwise to 1 molar equivalent of the amine (1) (1.28 g, 73 mL of dichloromethane) by keeping the temperature below 5° C. The solution was warmed to reflux for 2 h with 1 molar equivalent of puromycin 2HCl (2.997 g) to yield the desired urea (4, 2.64 g, 68.6%) as an off-white sticky solid. $^1$H-NMR spectrum in DMSOd6 is in accordance with the structure of compound 4.

Synthesis of 5 (Scheme K; FIG. 44)

The Boc amine (4) (2.64 g in 53 mL of dichloromethane) was deprotected by 10 molar equivalents of pure TFA (2.66 mL) to yield the amine TFA salt (5, ~60%) as a clear colourless oil. The final mass exceeded 100% mass yield due to presence of TFA (Scheme X). The deprotection was accompanied by cleavage of the purine moiety so the reaction was stopped at 57% desired product, 26% SM (by LCMS). Attempts to free base and purify (5) lead to decomposition.

Synthesis of 6 (Scheme F; FIG. 45)

CDI was stirred in pyridine (10 ml) at 0-5° C. under N$_2$. The amine TFA salt (3) in pyridine was charged over 10 mins and the mixture was allowed to warm to RT until LCMS indicated complete formation of the imidazole intermediate. A solution of the crude puromycin amine TFA salt in pyridine (5) was charged over 1'. The resulting mixture was warmed to RT and the reaction monitored by LCMS for ~24 h until the formation of desired product (57% conversion) had appeared to have stalled. The mixture was worked up and purified by column chromatography on silica eluting with 2-20% MeOH/DCM until the desired product eluted. The evaporated product was triturated in MeCN to yield 3PP (101 mg) as a beige solid and, after further purification of the mixed fractions and mother liquors, a 2nd crop (27.4 mg). Both crops satisfied quality controls (>92% by LC_MS analysis).

NMR and LCMS Data of Product 3PP $^1$H NMR (400 MHz, DMSO-d$_6$) δ=8.43 (s, 1H), 8.23 (s, 1H), 8.09 (d, J=7.7, 1H, CONH), 7.836 (t, J=5.6, 1H, CONH), 7.11 (d, J=8.6, 2H), 6.83 (d, J=8.6, 2H), 6.16 (m, 2H), 5.97 (m, 3H), 5.16 (t, J=5.3 Hz, 1H), 4.43 (m, 2H), 3.92 (m, 1H), 3.72 (s, 3H), 3.65-3.03 (series of m), 2.86 (dd, J=5.5, 14.4, 1H), 2.73 (t, J=2.7, 1H, —OCH), 2.70 (dd, J=8.5, 14.4, 1H), 2.14 (dt, J=2.7, 7.0, 2H, CH$_2$—C≡), 2.07 (t, J=7.3 Hz, 2H, NHCO—CH$_2$—C—C—C—C≡), 1.54 (m, 2H, —CH$_2$—C—C—C≡), 1.40 (m, 2H, —CH$_2$—C—C≡).

Purity (>90%) established by HPLC-MS. In particular the [M−H]$^-$ at m/z 927.5 observed in ESI(−) negative ion mode is consistent with its molecular formula C$_{43}$H$_{65}$N$_{11}$O$_{12}$ as well as the [M+Na]$^+$ at m/z 951.4 observed in ESI(+) positive ion mode is consistent with its molecular formula C$_{43}$H$_{66}$N$_{11}$NaO$_{12}$$^+$ Synthesis of the Azide-3P Molecule.

The molecules bearing the azide residue are selected from commercially available precursors (e.g. azide-N-hydroxysuccinimidyl ester, #88902, Life Technologies). Jeffamine (7 mmol) was dissolved in 500 mL acetonitrile (MeCN, Sigma #34888). 3 mmol of the azide-N-hydroxysuccinimidyl ester (azide-NHS) was dissolved in DMF (10 mL). This solution was added into a dropping funnel. The azide-NHS solution were then added dropwise to the jeffamine solution and stirred overnight, at 0-5° C. under $N_2$. The product is then purified by preparative HPLC. The synthesis of the full length molecule can then proceed from step 3 of the paragraph 'chemical synthesis of the 3P molecule' (material and methods).

Functionalization of a Solid Surface and Binding of the Molecule on a Functionalized (Receptor Like) Solid Surface (Scheme VI and VII; FIGS. 46 and 47, Respectively).

Since the azide and the alkyne functional group are exchangeable on the 'A' moiety of general formula (I), here we describe two different routes for surface functionalization:

Route A (the alkyne on the solid surface coupling an azide-3P molecule;

Route B (the azide on the solid surface coupling the alkyne-3P molecule)

Route A

Silicon wafers are cleaned for 30 min in hot Piranha solution (100° C., 1 vol 30% by mass aqueous hydrogen peroxide to 3 vol sulfuric acid), before being transferred to an aqueous fluoride solution (2.5% hydrofluoric acid, 1.5 min). Subsequently, the samples are transferred, taking extra care to exclude air completely from a Schlenk flask, to a degassed sample of 1,8-nonadiyne (Sigma, #161306). The sample is kept under a stream of argon while the reaction vessel was immersed in a oil bath set to 170° C. for 3 h. The flask is then opened to the atmosphere, and the functionalized surface sample rinsed consecutively with copious amounts chloroform, ethyl acetate, and then ethanol before being either analyzed or further reacted with substituted azide species.

In a typical click procedure, to a reaction vial containing the alkyne-functionalized silicon surface is added the (i) 10 mM azide (R—N3, where R is the azide 3P-molecule), ethanol/water 1:1, (ii) copper(II) sulfate pentahydrate (1 mol % relative to the azide), and (iii) sodium ascorbate (25 mol % relative to the azide). Reactions are carried out at room temperature, without excluding air from the reaction environment, and stopped after 17 to 18 h. The prepared surface-bound [1,2,3]-triazole samples are rinsed consecutively with copious amounts of ethyl acetate, ethanol, and water and then analyzed.

Alternatively, commercially available solid surfaces functionalized with the alkyne residues are used to covalently couple the azide functionalized molecule with general formula (I). Alkyne agarose beads (#CLK-1032-2, Jena Bioscience) or alkyne magnetic beads (CLK-1035-1, Jena Bioscience) are efficient matrix to covalently attach the molecule.

Route B.

Silicon wafers are sonicated and exposed to a UV/ozone atmosphere in a commercial cleaning chamber for 20 min. Monolayers are adsorbed by immersing the wafers in a 1 mmol solution of 11-bromoundecyltrichlorosilane (alternatively (3-Bromopropyl)trichlorosilane can be used; Sigma, #437808) in toluene for 45 min. After removal from the adsorbate solution, the wafers are sonicated in toluene, gently scrubbed with a toluene soaked tissue to remove physisorbed multilayers, and rinsed with toluene, acetone, and ethanol. Finally, they are sonicated in ethanol and blow-dried in high-purity nitrogen. The exchange of the bromine against the azide group is carried out by immersing the wafers in a saturated solution of sodium azide in DMF for 48 h at room temperature, followed by thorough rinsing with distilled water, ethanol, acetone, and toluene.

Cycloaddition reactions with the azide-functionalized wafers are carried out in a manner similar to that for the powdered substrates by immersing the wafers for 24 h in 1 mL of the appropriate terminal alkyne (R—CCH, where R is the alkyne 3P-molecule).

Alternatively, alkyne functionalized molecule of general formula (I) can covalently be coupled with commercially available magnetic beads functionalized with the azide residues (#CLK-1036-1, Jena Bioscience).

REFERENCES

1. Rich, A. Polyribosomes. *Sci. Am.* 209, 44-53 (1963).
2. Warner J R, Knopf P M, R. A multiple ribosomal structure in protein synthesis. *Proc Natl Acad Sci USA*. January 1963; 49(1) 122-129. 49, 122-129 (1963).
3. Myasnikov, A. G. et al. The molecular structure of the left-handed supra-molecular helix of eukaryotic polyribosomes. *Nat. Common.* 5, 5294 (2014).
4. Mrazek, J. et al. Polyribosomes Are Molecular 3D Nanoprinters That Orchestrate the Assembly of Vault Particles. *ACS Nano* 6, 21-34 (2014).
5. Viero, G. et al. Three distinct ribosome assemblies modulated by translation are the building blocks of polysomes. *J. Cell Biol.* 208, 531-596 (2015).
6. Kopeina, G. S. et al. Step-wise formation of eukaryotic double-row polyribosomes and circular translation of polysomal mRNA. *Nucleic Acids Res.* 36, 2476-88 (2008).
7. Brandt, F., Carlson, L.-A., Marti, F. U., Baumeister, W. & Grünewald, K. The three-dimensional organization of polyribosomes in intact human cells. *Mol. Cell* 39, 560-9 (2010).
8. Ortiz, J. O. et al. Structure of hibernating ribosomes studied by cryoelectron tomography in vitro and in situ. *J. Cell Biol.* 190, 613-621 (2010).
9. Brandt, F. et al. The Native 3D Organization of Bacterial Polysomes. *Cell* 136, 261-271 (2009).
10. Ruggero, D. Translational control in cancer etiology. *Cold Spring Harb. Perspect. Biol.* 5, (2013).
11. Bhat, M. et al. Targeting the translation machinery in cancer. *Nat. Rev. Drug Discov.* 14, 261-278 (2015).
12. Branco-Price, C., Kawaguchi, R., Ferreira, R. B. S Bailey-Serres, J. Genome-wide analysis of transcript abundance and translation in *Arabidopsis* seedlings subjected to oxygen deprivation. *Ann. Bot.* 96, 647-60 (2005).
13. Larsson, O. et al. Distinct perturbation of the translatome by the antidiabetic drug metformin. *Proc. Natl. Acad. Sci.* 109, 8977-8982 (2012).
14. Yángüez, E., Castro-Sanz, A. B., Fernández-Bautista, N., Oliveros, J. C. & Castellano, M. M. Analysis of genome-wide changes in the translatome of *Arabidopsis* seedlings subjected to heat stress. *PLoS One* 8, e71425 (2013).
15. Arava, Y. et al. Genome-wide analysis of mRNA translation profiles in *Saccharomyces cerevisiae*. *Proc. Natl. Acad. Sci. U.S.A* 100, 3869-94 (2003).
16. Tebaldi, T. et al. Widespread uncoupling between transcriptome and translatome variations after a stimulus in mammalian cells. *BMC Genomics* 13, 220 (2012).

17. Heiman, M. et al. A translational profiling approach for the molecular characterization of CNS cell types. *Cell* 135, 738-48 (2008).
18. Ingolia, N. T., Ghaemmaghami, S., Newman, J. R. S. & Weissman, J. S. Genome-wide analysis in vivo of translation with nucleotide resolution using ribosome profiling. *Science* 324, 218-23 (2009).
19. Gao, X. et al. Quantitative profiling of initiating ribosomes in vivo. *Nat. Methods* (2014).
20. Lee, S. et al. PNAS Plus: Global mapping of translation initiation sites in mammalian cells at single-nucleotide resolution. *Proc. Natl. Acad. Sci.* 109, E2424-E2432 (2012).
21. Aviner, R., Geiger, T. & Elroy-Stein, O. Genome-wide identification and quantification of protein synthesis in cultured cells and whole tissues by puromycin-associated nascent chain proteomics (PUNCH-P). *Nat. Protoc.* 9, 751-60 (2014).
22. Schwanhäusser, B. et al. Global quantification of mammalian gene expression control. *Nature* 473, 337-342 (2011).
23. Juntawong, P., Girke, T., Bazin, J. & Bailey-Serres, J. Translational dynamics revealed by genome-wide profiling of ribosome footprints in *Arabidopsis*. *Proc. Natl. Acad. Sci. U.S.A.* 111, E203-12 (2014).
24. Warner, J. R., Knopf, P. M. & Rich, A. A multiple ribosomal structure in protein synthesis. *Proc. Natl. Acad. Sci. (U.S.A.)* 49, 122-129 (1963).
25. Arava, Y. et al. Genome-wide analysis of mRNA translation profiles in *Saccharomyces cerevisiae*. *Proc. Natl. Acad. Sci. U.S.A* 100, 3689-3394 (2003).
26. Lackner, D. H. et al. A Network of Multiple Regulatory Layers Shapes Gene Expression in Fission Yeast. *Mol. Cell* 26, 145-155 (2007).
27. Thermann, R. & Hentze, M. W. *Drosophila* miR2 induces pseudo-polysomes and inhibits translation initiation. *Nature* 447, 675-878 (2007).
28. Graber, T. E. et al. Reactivation of stalled polyribosomes in synaptic plasticity. *Proc. Natl. Acad. Sci. U.S.A.* 110, 16205-10 (2013).
29. Anger, A. M. et al. Structures of the human and *Drosophila* 80S ribosome. *Nature* 497, 80-5 (2013).
30. Hansen, J. L., Moore, P. B. & Steitz, T. a. Structures of five antibiotics bound at the peptidyl transferase center of the large ribosomal subunit. *J. Mol. Biol.* 330, 1061-1075 (2003).
31. Nissen, P., Hansen, J., Ban, N., Moore, P. B. & Steitz, T. A. The structural basis of ribosome activity in peptide bond synthesis. *Science* 289, 920-930 (2000).
32. Rabl, J., Leibundgut, M., Ataide, S. F., Haag, A. & Ban, N. Crystal structure of the eukaryotic 40S ribosomal subunit in complex with initiation factor 1. *Science* 331, 730-736 (2011).
33. Klinge, S., Voigts-Hoffmann, F., Leibundgut, M. & Ban, N. Atomic structures of the eukaryotic ribosome. *Trends Biochem. Sci.* 37, 189-198 (2012).
34. Yarmolinsky, M. B. & Haba, G. L. Inhibition by puromycin of amino acid incorporation into protein. *Proc. Natl. Acad. Sci. U.S.A* 45, 1721-1729 (1959).
35. Wilson, D. N. Ribosome-targeting antibiotics and mechanisms of bacterial resistance. *Nat. Rev. Microbiol.* 12, 35-48 (2014).
36. Welch, M., Chastang, J. & Yarus, M. An Inhibitor of Ribosomal Peptidyl Transferase Using the Transition-State Analogy. *Biochemistry* 34, 385-390 (1995).
37. Pestka, S., Rosenfeld, H., Harris, R. & Hintikka, H. Studies on transfer ribonucleic acid-ribosome complexes. XXI. Effect of antibiotics on peptidyl-puromycin synthesis by mammalian polyribosomes. *J. Biol. Chem.* 247, 6895-6900 (1972).
38. Odom, O. W., Picking, W. D. & Hardesty, B. Movement of tRNA but not the nascent peptide during peptide bond formation on ribosomes. *Biochemistry* 29, 10734-10744 (1990).
39. Kukhanova, M. et al. The donor site of the peptidyltransferase center of ribosomes. *FEBS Lett.* 102, 198-203 (1979).
40. Schmeing, T. M. et al. A pre-translocational intermediate in protein synthesis observed in crystals of enzymatically active SOS subunits. *Nat Struct Biol* 9, 225-230 (2002).
41. Gambetti, P., Hirt, L., Stieber, A. & Shafer, B. Distribution of puromycin peptides in mouse entorhinal cortex. *Exp. Neurol.* 34, 223-228 (1972).
42. Schmidt, E. K., Clavarino, G., Ceppi, M. & Pierre, P. SUnSET, a nonradioactive method to monitor protein synthesis. *Nat. Methods* 6, 275-277 (2009).
43. Biyani, M., Husimi, Y. & Nemoto, N. Solid-phase translation and RNA-protein fusion: A novel approach for folding quality control and direct immobilization of proteins using anchored mRNA. *Nucleic Acids Res.* 34, (2006).
44. Roberts, R. W. & Szostak, J. W. RNA-peptide fusions for the in vitro selection of peptides and proteins. *Proc. Natl. Acad. Sci. U.S.A.* 94, 12297-12302 (1997).
45. Bernabò, P. et al. Studying translational control in non-model stressed organisms by polysomal profiling. *J. Insect Physiol.* 76, 30-35 (2015).
46. Nathans, d. & Neidle, A. Structural Requirements for Puromycin Inhibition of Protein Synthesis. *Nature* 197, 1076-1077 (1963).
47. Yarmolinsky, M. B. & Haba, G. L. Inhibition By Puromycin of Amino Acid Incorporation Into Protein. *Proc. Natl. Acad. Sci. U.S.A.* 45, 1721-1729 (1959).
48. ALLEN, D. W. & ZAMECNIK, P. C. The effect of puromycin on rabbit reticulocyte ribosomes. *Biochim. Biophys. Acta* 55, 865-874 (1962).
49. Ban, N., Nissen, P., Hansen, J., Moore, P. B. & Steitz, T. a. The complete atomic structure of the large ribosomal subunit at 2. 4 *A Resolut. Sci.* 289, 905±920 (2000).
50. Starck, S. R., Green, H. M., Alberola-Ila, J. & Roberts, R. W. A general approach to detect protein expression in vivo using fluorescent puromycin conjugates. *Chem. Biol.* 11, 999-1008 (2004).
51. Afshar-Kharghan, V., Li, C. Q., Khoshnevis-Asl, M. & Lopez, J. A. Kozak sequence polymorphism of the glycoprotein (GP) Ibalpha gene is a major determinant of the plasma membrane levels of the platelet GP Ib-IX-V complex. *Blood* 94, 186-191 (1999).
52. Higashi, K. et al. Enhancement of 4-1 frameshift by polyamines during translation of polypeptide release factor 2 in *Escherichia coli*. *J. Biol. Chem.* 281, 9527-9537 (2006).
53. Ingolia, N. T. Ribosome profiling: new views of translation, from single codons to genome scale. *Nat. Rev. Genet.* 15, 205-13 (2014).
54. Mura, M. et al. LARP1 post-transcriptionally regulates mTOR and contributes to cancer progression. *Oncogene* 1-12 (2014).
55. Yoon, J.-H. et al. Scaffold function of long non-coding RNA hotair in protein ubiquitination. *Nat. Commun.* 4, 2939 (2013).

56. Ingolia, N. T., Lareau, L. F. & Weissman, J. S. Ribosome profiling of mouse embryonic stem cells reveals the complexity and dynamics of mammalian proteomes. *Cell* 147, 789-802 (2011).
57. N. Oll, H., Staehelin, t. & Wettstein F. O. Ribosomal Aggregates Engaged in Protein Synthesis: Ergosome Breakdown and Messenger Ribonucleic Acid Transport. *Nature* 198, 632-636 (1963).
58. Wettstein, F. O., Staehelin, t. & Noll, H. Ribosomal Aggregate Engaged in Protein Synthesis: Characterization of the Ergosome. *Nature* 197, 430-435 (1963).
59. Mortazavi, A., Williams, B. A., McCue, K., Schaeffer, L. & Wold, B. Mapping and quantifying mammalian transcriptomes by RNA-Seq. *Nat. Methods* 5, 621-628 (2008).
60. Nagashima, T. et al. Quantitative transcriptional control of ErbB receptor signaling undergoes graded to biphasic response for cell differentiation. *J. Biol. Chem.* 282, 4045-4056 (2007).
61. Nagashima, T. et al. Feedforward regulation of mRNA stability by prolonged extracellular signal-regulated kinase activity. *FEBS J.* 282, 613-629 (2015).
62. Foss, E. J. et al. Genetic variation shapes protein networks mainly through non-transcriptional mechanisms. *PLoS Biol.* 9, (2011).
63. Ghazalpour, A. et al. Comparative analysis of proteome and transcriptome variation in mouse. *PLoS Genet.* 7, (2011).
64. Zhang, B. et al. Proteogenomic characterization of human colon and rectal cancer. *Nature* 1-21 (2014). doi:10.1038/nature13438
65. Gry, M. et al. Correlations between RNA and protein expression profiles in 23 human cell lines. *BMC Genomics* 10, 365 (2009).
66. Guydosh, N. R. & Green, R. Dom34 rescues ribosomes in 3' untranslated regions. *Cell* 156, 950-962 (2014).
67. Lareau, L. F., Hite, D. H., Hogan, G. J. & Brown, P. O. Distinct stages of the translation elongation cycle revealed by sequencing ribosome-protected mRNA fragments. *Elife* 2014, 1-16 (2014).
68. Lunelli, L. et al. Peering at Brain Polysomes with Atomic Force Microscopy. *J. Vis. Exp.* (2016).

The invention claimed is:

1. A molecule of general formula (I):

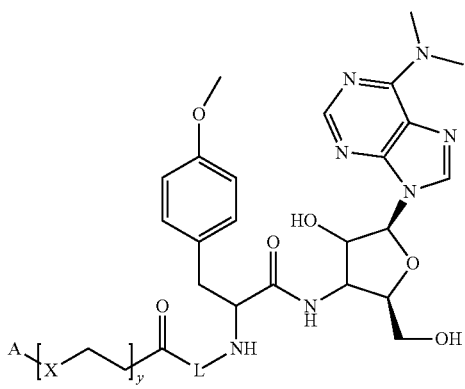

wherein
- A is selected from a receptor or a ligand of a receptor-ligand system;
- X is selected from an oxygen atom (O) or a carbon atom (C);
- y is an integer number from 0 to 10;

L is a molecule of general formula (VI):

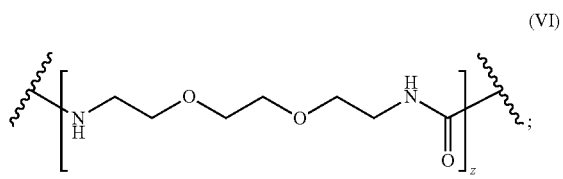

Z is an integer number comprised in the range 2 to 10; and enantiomers thereof; and wherein the ligand-receptor system is selected from the group consisting of: biotin-avidin, biotin-streptavidin, biotin-neutravidin, and alkyne residue-azide residue.

2. The molecule according to claim 1, wherein A is selected from the group consisting of:

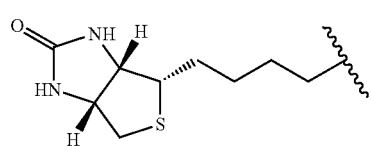

-continued

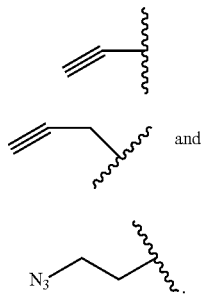

(III)

(IV) and (V)

3. The molecule according to claim 1, wherein y is equal to 0.

4. The molecule according to claim 1, wherein z is equal to 2.

5. A method for isolating at least one active ribosome from a biological sample comprising contacting a molecule according to claim 1 with the biological sample and isolating the at least one active ribosome.

6. The method according to claim 5, wherein the biological sample is a cell or tissue lysate.

7. The method according to claim 6, wherein the cell is bacterial, archaea or eukaryotic cells.

8. The method according to claim 5, wherein the at least one active ribosome is associated to an RNA, a mRNA, or a protein.

9. A method for ribosome profiling comprising treating a biological sample with an endoribonuclease, contacting the biological sample with a molecule according to claim 1, purifying at least one ribosome-protected fragment, sequencing the at least one ribosome-protected fragment, and mapping the sequence to a genome.

10. A kit for isolating at least one active ribosome from a biological sample, wherein the kit comprises:
   i) a first reagent comprising at least one molecule according to claim 1; and
   ii) a solid phase, wherein the solid phase is functionalized with die other of the receptor or the ligand of the receptor-ligand system, so that the solid phase binds to the first reagent.

11. The kit according to claim 10, wherein the first reagent is in a liquid or solid state.

12. The kit according to claim 10, wherein the kit further comprises at least one of:
   a) a solubilization solution for solubilizing the first reagent, when the first reagent is in the solid state;
   b) an incubation solution for incubating the first reagent with the biological sample;
   c) a washing solution for washing the solid phase after contacting with the biological sample;
   d) an RNase eliminating and resuspension solution for removing RNase from die solid phase;
   e) a negative control; and
   f) instructions for use.

13. The kit according to claim 10, wherein the solid phase is functionalized with streptavidin, neutravidin, avidin, azide residue, or alkyne residue.

* * * * *

UNITED STATES PATENT AND TRADEMARK OFFICE
CERTIFICATE OF CORRECTION

PATENT NO. : 10,183,955 B2  
APPLICATION NO. : 15/744976  
DATED : January 22, 2019  
INVENTOR(S) : Massimiliano Clamer et al.

Page 1 of 1

It is certified that error appears in the above-identified patent and that said Letters Patent is hereby corrected as shown below:

In the Claims

Column 44, Line 10, Claim 10, the word "die" should read --the--.

Column 44, Line 24, Claim 12, the word "die" should read --the--.

Signed and Sealed this
Thirtieth Day of July, 2019

Andrei Iancu
*Director of the United States Patent and Trademark Office*

SEQUENCE LISTING

<160> NUMBER OF SEQ ID NOS: 8

<210> SEQ ID NO 1
<211> LENGTH: 19
<212> TYPE: DNA
<213> ORGANISM: artificial
<220> FEATURE:
<223> OTHER INFORMATION: positive control primer - forward

<400> SEQUENCE: 1
cggcgccatt ctatcctct                                               19

<210> SEQ ID NO 2
<211> LENGTH: 20
<212> TYPE: DNA
<213> ORGANISM: artificial
<220> FEATURE:
<223> OTHER INFORMATION: positive control primer reverse

<400> SEQUENCE: 2
ccgataaata acgcgcccaa                                              20

<210> SEQ ID NO 3
<211> LENGTH: 20
<212> TYPE: DNA
<213> ORGANISM: artificial
<220> FEATURE:
<223> OTHER INFORMATION: negative control primer forward

<400> SEQUENCE: 3
gcagtaccta agccctcgat                                              20

<210> SEQ ID NO 4
<211> LENGTH: 20
<212> TYPE: DNA
<213> ORGANISM: artificial
<220> FEATURE:
<223> OTHER INFORMATION: negative control primer - reverse

<400> SEQUENCE: 4
ggtggacagc aaatgggtac                                              20

<210> SEQ ID NO 5

```
<211> LENGTH: 20
<212> TYPE: DNA
<213> ORGANISM: artificial
<220> FEATURE:
<223> OTHER INFORMATION: 18S rRNA forward primer

<400> SEQUENCE: 5
ggatccattg gagggcaagt                                               20

<210> SEQ ID NO 6
<211> LENGTH: 22
<212> TYPE: DNA
<213> ORGANISM: artificial
<220> FEATURE:
<223> OTHER INFORMATION: 18S rRNA reverse primer

<400> SEQUENCE: 6
acgagctttt taactgcagc aa                                            22

<210> SEQ ID NO 7
<211> LENGTH: 20
<212> TYPE: DNA
<213> ORGANISM: artificial
<220> FEATURE:
<223> OTHER INFORMATION: EGFP gene forward primer

<400> SEQUENCE: 7
aagcagcacg acttcttcaa                                               20

<210> SEQ ID NO 8
<211> LENGTH: 20
<212> TYPE: DNA
<213> ORGANISM: artificial
<220> FEATURE:
<223> OTHER INFORMATION: EGFP gene reverse primer

<400> SEQUENCE: 8
acgttgtggc tgttgtagtt                                               20
```